(12) United States Patent
Akthakul et al.

(10) Patent No.: US 11,660,313 B2
(45) Date of Patent: *May 30, 2023

(54) COMPOSITIONS AND METHODS FOR APPLICATION OVER SKIN

(71) Applicant: Shiseido Company, Limited, Tokyo (JP)

(72) Inventors: Ariya Akthakul, Boston, MA (US); Nithin Ramadurai, Wakefield, MA (US); Amir Nashat, Boston, MA (US); Daniela Beccati, Watertown, MA (US); Melaney Bouthillette, Newton, MA (US)

(73) Assignee: Shiseido Company, Limited, Tokyo (JP)

( * ) Notice: Subject to any disclaimer, the term of this patent is extended or adjusted under 35 U.S.C. 154(b) by 208 days.

This patent is subject to a terminal disclaimer.

(21) Appl. No.: 17/139,268

(22) Filed: Dec. 31, 2020

(65) Prior Publication Data

US 2021/0213046 A1 Jul. 15, 2021

Related U.S. Application Data

(63) Continuation of application No. 15/774,350, filed as application No. PCT/US2016/061150 on Nov. 9, 2016, now Pat. No. 11,160,827.

(60) Provisional application No. 62/252,903, filed on Nov. 9, 2015.

(51) Int. Cl.
| | | |
|---|---|---|
| A61K 31/80 | (2006.01) | |
| A61K 9/00 | (2006.01) | |
| A61K 9/70 | (2006.01) | |
| A61L 26/00 | (2006.01) | |
| C08G 77/12 | (2006.01) | |
| C08G 77/20 | (2006.01) | |
| A61K 8/895 | (2006.01) | |
| A61K 45/06 | (2006.01) | |
| A61K 47/02 | (2006.01) | |
| A61K 47/34 | (2017.01) | |
| A61K 31/573 | (2006.01) | |
| A61K 31/58 | (2006.01) | |

(52) U.S. Cl.
CPC ........... *A61K 31/80* (2013.01); *A61K 9/0014* (2013.01); *A61K 9/7015* (2013.01); *A61K 31/573* (2013.01); *A61K 31/58* (2013.01); *A61L 26/0019* (2013.01); *A61L 26/0061* (2013.01)

(58) Field of Classification Search
CPC .. A61K 31/80; A61K 2300/00; A61K 9/7015; A61K 2800/81; A61K 2800/95; A61K 31/573; A61K 31/58; A61K 45/06; A61K 47/02; A61K 47/34; A61K 8/895; A61K 9/0014; A61L 26/0019; A61L 26/0061; A61L 26/0052; A61L 26/0076; A61P 17/02; A61P 17/00; A61Q 17/00; A61Q 17/04; A61Q 19/00; C08L 83/04; C08L 83/00; C08K 5/56; C08G 77/12; C08G 77/20; C08G 77/04; C08F 8/00
See application file for complete search history.

(56) References Cited

U.S. PATENT DOCUMENTS

| | | | |
|---|---|---|---|
| 3,261,802 | A | 7/1966 | Bobear et al. |
| 3,419,006 | A | 12/1968 | King et al. |
| 3,882,083 | A | 5/1975 | Berger et al. |
| 3,884,866 | A | 5/1975 | Jeram et al. |
| 4,025,485 | A | 5/1977 | Kodama et al. |
| 4,683,278 | A | 7/1987 | Suzuki |
| 4,908,140 | A | 3/1990 | Bausch et al. |
| 5,173,291 | A | 12/1992 | Brink |
| 5,190,827 | A | 3/1993 | Lin et al. |
| 5,219,560 | A | 6/1993 | Suzuki et al. |
| 5,525,344 | A | 6/1996 | Wivell |
| 5,534,609 | A | 7/1996 | Lewis et al. |

(Continued)

FOREIGN PATENT DOCUMENTS

| | | | | |
|---|---|---|---|---|
| CN | 103920179 A | * | 7/2014 | ............ A61L 15/18 |
| CN | 103920179 A | | 7/2014 | |

(Continued)

OTHER PUBLICATIONS

Extended European Search Report dated Aug. 27, 2019 for European App. No. 16864921.8.

(Continued)

*Primary Examiner* — Jeffrey T. Palenik
(74) *Attorney, Agent, or Firm* — Jones Day

(57) ABSTRACT

Disclosed herein are compositions that can form a covering, layer, film, device, and/or prosthetic skin that can be comfortably worn to provide skin barrier function, skin hydration and therapeutic and aesthetic benefits. The present invention provides novel compositions that have low tackiness and form quickly, resulting in a wearable, comfortable (maintains temperature and humidity), breathable, thin, optically invisible, cosmetically elegant, flexible, stretchable, elastic and body-movement conforming, yet long-lasting covering, layer, film, device, and/or prosthetic skin on the skin or any other body surface. The present invention provides novel compositions that can form a covering, layer, film, device, and/or prosthetic skin that works for extended periods in excess of about 24 hours, while retaining function during and after exercising, showering and swimming (in sea-water, fresh water and chlorinated water), steam room (heat at high humidity), and sauna (heat at low humidity).

9 Claims, 30 Drawing Sheets

(56) References Cited

U.S. PATENT DOCUMENTS

| | | |
|---|---|---|
| 5,616,632 A | 4/1997 | Fujiki et al. |
| 5,800,816 A | 9/1998 | Brieva et al. |
| 5,919,437 A | 7/1999 | Lee et al. |
| 5,919,468 A | 7/1999 | Bara |
| 5,922,470 A | 7/1999 | Bracken et al. |
| 6,066,326 A | 5/2000 | Afriat et al. |
| 6,313,190 B1 | 11/2001 | Bublewitz et al. |
| 6,342,237 B1 | 1/2002 | Bara |
| 6,355,724 B1 | 3/2002 | LeGrow et al. |
| 6,391,944 B2 | 5/2002 | Canpont et al. |
| 6,423,322 B1 | 7/2002 | Fry |
| 6,471,985 B2 | 10/2002 | Guyuron et al. |
| 6,512,072 B1 | 1/2003 | Gantner et al. |
| 6,544,532 B1 | 4/2003 | Jager-Lezer et al. |
| 6,545,076 B2 | 4/2003 | Kaiya et al. |
| 6,573,299 B1 | 6/2003 | Petrus |
| 6,613,185 B1 | 9/2003 | Valade et al. |
| 6,682,749 B1 | 1/2004 | Potechin et al. |
| 6,762,242 B1 | 7/2004 | Torto et al. |
| 6,998,427 B2 | 2/2006 | Del Torto et al. |
| 7,078,026 B2 | 7/2006 | Ferrari et al. |
| 7,083,800 B1 | 8/2006 | Terren et al. |
| 7,148,306 B2 | 12/2006 | Frank et al. |
| 7,270,828 B2 | 9/2007 | Masuda et al. |
| 7,273,658 B2 | 9/2007 | Benayoun et al. |
| 7,335,708 B2 | 2/2008 | Bublewitz et al. |
| 7,425,292 B2 | 9/2008 | Yang et al. |
| 7,452,957 B2 | 11/2008 | Sayre |
| 7,482,419 B2 | 1/2009 | Caprasse et al. |
| 7,572,514 B2 | 8/2009 | Howe et al. |
| 7,750,106 B2 | 7/2010 | Zheng et al. |
| 8,034,323 B2 | 10/2011 | Zheng et al. |
| 8,133,478 B2 | 3/2012 | Maitra et al. |
| 8,263,055 B2 | 9/2012 | Do |
| 8,569,792 B2 | 10/2013 | Mitani et al. |
| 8,611,746 B2 | 12/2013 | Pincemin et al. |
| 8,658,755 B2 | 2/2014 | Saito |
| 8,691,202 B2 | 4/2014 | Yu et al. |
| 8,920,783 B2 | 12/2014 | Lin |
| 9,044,288 B2 | 6/2015 | Angeletakis |
| 9,096,721 B2 | 8/2015 | Garaud et al. |
| 9,114,096 B2 | 8/2015 | Yu et al. |
| 9,186,315 B2 | 11/2015 | Singer |
| 9,308,221 B2 | 4/2016 | Yu et al. |
| 9,333,223 B2 | 5/2016 | Yu et al. |
| 9,511,034 B1 | 12/2016 | Garrett |
| 9,724,363 B2 | 8/2017 | Yu et al. |
| 9,937,200 B2 | 4/2018 | Yu et al. |
| 10,022,396 B2 | 7/2018 | Yu et al. |
| 10,918,661 B2 | 2/2021 | Yu et al. |
| 10,973,848 B2 | 4/2021 | Yu et al. |
| 11,160,827 B2 | 11/2021 | Akthakul et al. |
| 2002/0022040 A1 | 2/2002 | Robinson et al. |
| 2002/0122771 A1 | 9/2002 | Holland et al. |
| 2003/0180281 A1 | 9/2003 | Bott et al. |
| 2004/0258628 A1 | 12/2004 | Riedel et al. |
| 2005/0148727 A1 | 7/2005 | Ajbani et al. |
| 2005/0158260 A1 | 7/2005 | Ferrari et al. |
| 2005/0175562 A1 | 8/2005 | Hadasch et al. |
| 2005/0261632 A1 | 11/2005 | Xu |
| 2006/0029623 A1 | 2/2006 | Astruc et al. |
| 2007/0142575 A1 | 6/2007 | Zheng et al. |
| 2007/0142599 A1 | 6/2007 | Zheng et al. |
| 2007/0212314 A1 | 9/2007 | Murphy et al. |
| 2007/0244230 A1 | 10/2007 | Sixt et al. |
| 2007/0292463 A1 | 12/2007 | Spector |
| 2008/0102050 A1 | 5/2008 | Li et al. |
| 2008/0159970 A1 | 7/2008 | Willemin |
| 2008/0279797 A1 | 11/2008 | Maitra et al. |
| 2008/0281055 A1 | 11/2008 | Schlitzer et al. |
| 2009/0035246 A1 | 2/2009 | Do |
| 2009/0214455 A1 | 8/2009 | Blin et al. |
| 2009/0317343 A1 | 12/2009 | Lin et al. |
| 2010/0112019 A1 | 5/2010 | Thevenet |
| 2010/0152135 A1 | 6/2010 | Blin |
| 2010/0178266 A1 | 7/2010 | Huggins et al. |
| 2010/0179105 A1 | 7/2010 | Blin et al. |
| 2011/0040242 A1 | 2/2011 | Fallon et al. |
| 2011/0166275 A1 | 7/2011 | Zhang |
| 2011/0170864 A1 | 7/2011 | Tani et al. |
| 2012/0237461 A1 | 9/2012 | Yu et al. |
| 2012/0251600 A1 | 10/2012 | Yu et al. |
| 2013/0052356 A1 | 2/2013 | Li |
| 2013/0078209 A1 | 3/2013 | Yut et al. |
| 2013/0178571 A1 | 7/2013 | Ogawa et al. |
| 2014/0004065 A1 | 1/2014 | Souda et al. |
| 2014/0004073 A1 | 1/2014 | Yu et al. |
| 2014/0010769 A1 | 1/2014 | Lomakin et al. |
| 2014/0044670 A1 | 2/2014 | Yu et al. |
| 2014/0322519 A1 | 10/2014 | Ahn et al. |
| 2015/0190516 A1 | 7/2015 | Cauvin et al. |
| 2015/0274971 A1 | 10/2015 | Endo et al. |
| 2015/0284590 A1 | 10/2015 | Endo et al. |
| 2016/0143840 A1 | 5/2016 | Yu et al. |
| 2016/0250250 A1 | 9/2016 | Yu et al. |
| 2016/0317574 A1 | 11/2016 | Yu et al. |
| 2017/0189317 A1 | 7/2017 | Bernard et al. |
| 2017/0360824 A1 | 12/2017 | Yu et al. |
| 2017/0368094 A9 | 12/2017 | Yu et al. |
| 2018/0256636 A1 | 9/2018 | Yu et al. |
| 2018/0296591 A1 | 10/2018 | Yu et al. |
| 2020/0009184 A1 | 1/2020 | Akthakul et al. |
| 2021/0213047 A1 | 7/2021 | Akthakul et al. |
| 2021/0252041 A1 | 8/2021 | Akthakul et al. |
| 2021/0338562 A1 | 11/2021 | Akthakul et al. |
| 2022/0062327 A1 | 3/2022 | Yu et al. |
| 2022/0176013 A1 | 6/2022 | Akthakul et al. |

FOREIGN PATENT DOCUMENTS

| | | |
|---|---|---|
| EP | 0445982 A2 | 9/1991 |
| EP | 0851000 A2 | 7/1998 |
| EP | 0865787 A1 | 9/1998 |
| EP | 2090294 A1 | 8/2009 |
| FR | 2894817 A1 | 6/2007 |
| FR | 2910291 A1 | 6/2008 |
| FR | 2954143 A1 | 6/2011 |
| FR | 2956319 B1 | 8/2011 |
| JP | 2009/520002 A | 5/2009 |
| JP | 2009/530480 A | 8/2009 |
| WO | WO-2000/074738 A1 | 12/2000 |
| WO | WO-2007/071886 A2 | 6/2007 |
| WO | WO-2007/102859 A2 | 9/2007 |
| WO | WO-2007/117284 A2 | 10/2007 |
| WO | WO-2008/075282 A2 | 6/2008 |
| WO | WO-2009/042732 A1 | 4/2009 |
| WO | WO-2009/090074 A1 | 7/2009 |
| WO | WO-2009/090242 A1 | 7/2009 |
| WO | WO-2011/001217 A1 | 1/2011 |
| WO | WO-2012/030984 A1 | 3/2012 |
| WO | WO-2012/030993 A2 | 3/2012 |
| WO | WO-2013/044098 A1 | 3/2013 |
| WO | WO-2013/070302 A1 | 5/2013 |
| WO | WO-2013/076450 A1 | 5/2013 |
| WO | WO-2013/158844 A2 | 10/2013 |
| WO | WO-2015/068859 A1 | 5/2015 |
| WO | WO 2017/083398 | 5/2017 |
| WO | WO-2017/117438 A1 | 7/2017 |
| WO | WO-2020/067582 | 4/2020 |
| WO | WO-2020/212828 | 10/2020 |

OTHER PUBLICATIONS

Japanese Office Action dated Apr. 5, 2022 Application No. JP 2021-118522.
Zou et al., 2016, "Mechanisms of the Antimicrobial Activities of Graphene Materials," Journal of the American Chemical Society, 138:2064-2077.
Brook et al. (2007). "Pretreatment of Liquid Silicone Rubbers to Remove Volatile Siloxanes," *Ind. Eng. Chem. Res.* 46:8796-8805.
Correct Combo, [retrieved on Dec. 10, 2014 from on-line website http://www.drugs.com/otc/122754/correct-combo.html].

(56) References Cited

OTHER PUBLICATIONS

European Search Report, Application No. EP11822576, dated Mar. 16, 2015.
Fumed Silica: retrieved form internet: http://www.powerchemcorp.com/library/public/fumed_silica/SiSiB_Fumed_Silica.pdf. Retrieved on Sep. 4, 2016.
Hwang, S.M. et al. (2001). "Basis of Occlusive Therapy in Psoriasis: Correcting Defects in Permeability Barrier and Calcium Gradient," *International Journal of Dermatology* 40:223-231.
International Search Report and Written Opinion dated Dec. 3, 2012 for International App. No. PCT/US2012/056667.
International Preliminary Report on Patentability dated Mar. 25, 2014 for PCT Application No. PCT/US2012/05667.
International Search Report and Written Opinion dated Jan. 25, 2017 for International Application No. PCT/US16/61150.
Japanese Office Action, Application No. JP 2013-527273, dated Jun. 23, 2015.
Klykken, P. et al. (2004). "Silicone Film-Forming Technologies for Health Care Applications," *Dow Corning*; 8pp.
Leow, Y-H et al. (1997, e-pub. Jul. 12, 2009). "Effect of Occlusion on Skin," Journal of Dermatological Treatment 8(2):139-142.
Liquid Silicone Rubber: Global Product Selection Guide: retrieved from internet: https://www.dowcorning.com/content/publishedlit/95-1226-lsr-selection-guide.pdf. Retrieved on Sep. 4, 2016.
Ostergaard, Dow corning SA, Next Generation Rheology Control rings New Formulation Options for Personal Care, pp. 1-6:2008.
Quartz Powder: retrieved from internet: http://www.cosmeticanalysis.com/cosmetic-ingredients/quartz-powder.html. Retrieved on Apr. 25, 2017.
Silc Pig: retrieved from internet: https://www.smooth-on.com/product-line/silc-pig/. Retrieved on Sep. 4, 2016.
Silicones Plus product list, [retrieved on Dec. 10, 2014 from on-line website http://siliconesplus.com/storage/Silicones%20Pius%20Brochme_1.pdf].
TraumaSkin FX™ Platinum Silicone Sculpting/Casting Medium: retrieved from internet: http://web.archive.org/web/20100407000529/http://www.paintandpowderstore.com/products.php?cat=47. Retrieved on Apr. 25, 2017.
Yu, B. et al. (May 9, 2016). "An Elastic Second Skin," *Nature Materials* pp. 1-10.
Zhai, H. et al. (2001). "Effects of Skin Occlusion on Percutaneous Absorption: An Overview," *Skin Pharmacol Appl Skin Physiol* 14(1):1-10.
Zhai, H. et al. (2002). "Occlusion vs. Skin Barrier Function," *Skin Research and Technology* 8:1-6.
Zuo et al., 2015, "Sunlight-induced cross-linked luminescent films based on polysiloxanes and D-Limonene via Thiol-ene "click" chemistry", Advanced Functional Materials, 25(18):2754-2762.
Ritzhaupt-Kleissl et al., 2006, "Material Properties of Polymer Nanoparticle Composites for Micro Optical Applications," NSTI-Nanotech, 2:852-855.

\* cited by examiner

Coverage for hyperpigmentation
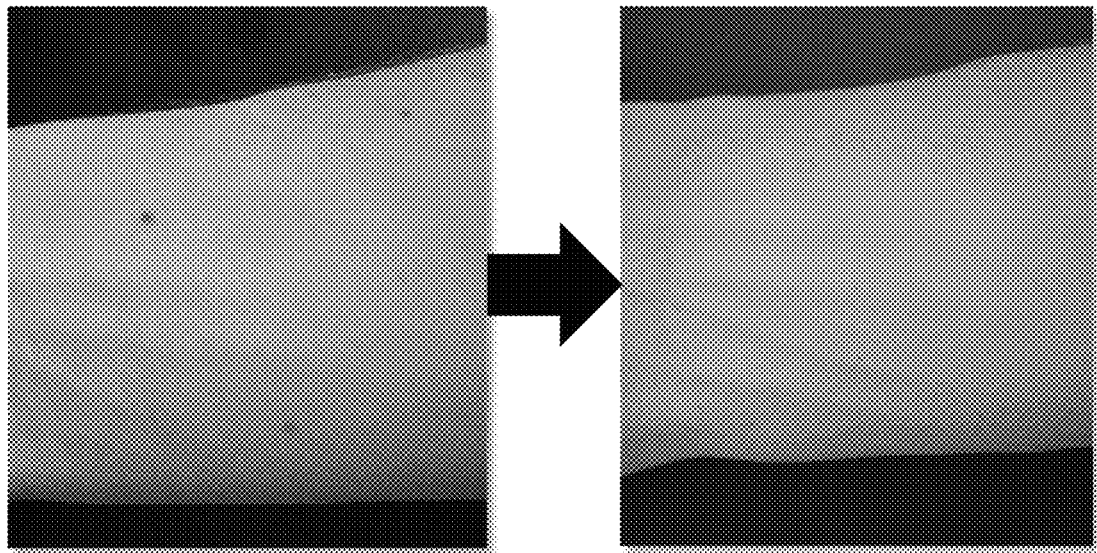
Coverage for tattoo
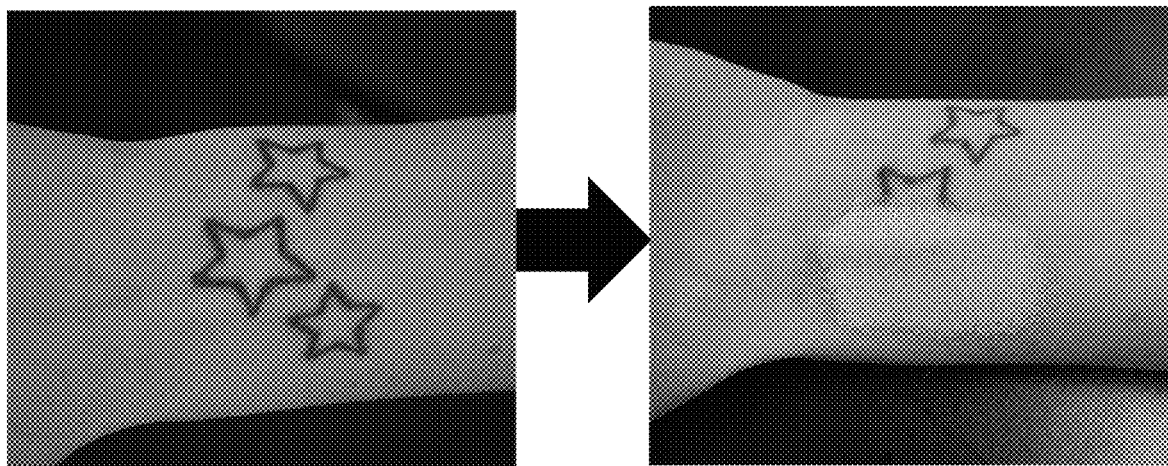
FIG. 9

PSORIASIS AREA AND SEVERITY INDEX ( PASI )

Patient's Name: _____  File #: _____

| Upon Arrival | ERYTHEMA (0-4) | DESQUAMATION (0-4) | INFILTRATION (0-4) | INVOLVEMENT* (in %) |
|---|---|---|---|---|
| Head | | | | |
| Trunk | | | | |
| Upper Limbs | | | | |
| Lower Limbs | | | | |

| Before Departure | ERYTHEMA (0-4) | DESQUAMATION (0-4) | INFILTRATION (0-4) | INVOLVEMENT* (in %) |
|---|---|---|---|---|
| Head | | | | |
| Trunk | | | | |
| Upper Limbs | | | | |
| Lower Limbs | | | | |

| ERYTHEMA | DESQUAMATION | INFILTRATION |
|---|---|---|
| 0 – No | 0 – No | 0 – No |
| 1 – Slight | 1 – Small and Few | 1 – Slight |
| 2 – Moderate | 2 – Small | 2 – Moderate |
| 3 – Severe | 3 – Many | 3 – Deep |
| 4 – Very Severe | 4 – Big and Many | 4 – Very Deep |

*For each part of the body, in percentage of this part.

FIG. 17

COMPOSITIONS AND METHODS FOR APPLICATION OVER SKIN

CROSS REFERENCES TO RELATED APPLICATIONS

The present application is a continuation of U.S. application Ser. No. 15/774,350, filed May 8, 2018, currently allowed, which is a U.S. national stage application of International Patent Application No. PCT/US2016/061150, filed Nov. 9, 2016, which claims priority to U.S. Provisional Patent Application No. 62/252,903, filed on Nov. 9, 2015, each of which is incorporated herein by reference in its entirety.

BACKGROUND OF THE INVENTION

Skin function, e.g., skin barrier function, is critical to protecting the body from physical injury and environmental factors, regulating skin hydration, regulating body temperature, providing protection from pathogenic invasions, and appearance. When skin is damaged, its ability to serve as an effective barrier is compromised, thus enabling external irritants and potentially pathogenic organisms to enter a subject. In addition, damaged skin can allow for increased transepidermal water loss when moisture present in the body is allowed to travel directly to the surface of the skin where it evaporates, leading to decreased skin hydration (e.g., dry, irritated skin), and loss of skin elasticity.

Skin hydration has been shown to significantly improve skin properties and quality of life for individuals with many conditions of compromised skin barrier function such as dermatitis and psoriasis (see, e.g., Guidelines of care for the management of atopic dermatitis, J. Am. Acad. Dermatol., 2014 71(1): 116-32; Guidelines of care for the management of psoriasis and psoriatic arthritis, J. Am. Acad. Dermatol. 2009, 60(4):643-59). However, individuals with such conditions still mainly rely on the use of occlusive dressings (see, e.g., Hwang et al., *Internat. J. Dermatol.* 2001, 40(3): 223-231), often in combination with topical ointments and/or moisturizers. For example, emollient based moisturizers increase hydration of the keratin in the stratum corneum and help to reduce scaling, therefore, are often considered an adjuvant therapy and an essential part of the management of such conditions. Occlusive dressings, topical ointments and moisturizers are a valuable first-line treatment, as skin hydration provides transient relief from irritation caused by transepidermal water loss. Skin hydration further leads to improved barrier function, as stratum corneum hydration makes the epidermis more resistant to external stressors and reduces the induction of other undesirable conditions such as the Koebner phenomena triggered by excoriation or maceration and infectious foci due to *Streptococcus pyogenes*. However, current occlusive dressings are often designed to exclude both oxygen and water, and thereby cutting off skin's oxygen access while providing skin hydration.

Occlusive dressings, topical ointments and/or moisturizers are often cumbersome, making routine activity for the individual difficult and resulting in poor patient compliance using such dressings, ointments and/or moisturizers. In addition, occlusive dressings, topical ointments and/or moisturizers often require multiple applications per day to be effective because they are readily worn off. Moreover, emollient base moisturizers can cause side effects, such as irritant dermatitis, allergic contact dermatitis, allergy to formula constituents, stinging, cosmetic acne, and other undesired effects. Therefore, it is desirable to find alternative methods of treating conditions of compromised skin barrier function that are both effective and without undesirable side effects.

The design and adoption of a wearable, skin-conforming material poses several fundamental challenges. First, the material must be safely worn on skin without causing skin irritations and/or sensitizations. Second, the materials must adhere to skin, while providing a breathable, but protective, interface to the environment. Third, the material must possess mechanical properties that accommodate normal skin's mechanical responses to motion while reinforcing inherent skin tension and elastic recoil. Fourth, the material should preferably mimic, or at least not significantly interfere with, the appearance of normal, healthy skin for a wide range of individual skin types. Examples of appearances of normal, healthy skin, such as lack of scaling, redness, and unevenness such as bumps and/or large pores, are described in Igarashi et al, The Appearance of Human Skin: A Survey, *Foundations and Trends® in Computer Graphics and Vision,* 2007 3(1):1-95.

There are commercially available, pre-formed, skin adherent wound dressings currently on the market, such as silicone wound dressing (e.g., Cica-Care®, Smith and Nephew, Andover, Mass.) and acrylic wound dressing (e.g., Tegaderm™, 3M, St. Paul, Minn.). However, such pre-formed wound dressings are of fixed area and size, cumbersome, visually noticeable, and do not provide sufficient flexibility and durability required by routine daily activities.

The 3M Company provides a "Liquid Bandage" product that claims to offer breathable, waterproof protection to keep out dirt and germs. However, such Liquid Bandages do not provide sufficient flexibility and durability required by routine daily activities, often have shiny/glossy appearances, and suffer from greatly compromised mechanically integrity and adhesiveness upon rubbing.

Yu et al. (United States Patent Publication 20130078209) disclose compositions for treating conditions of compromised skin barrier function such as dermatological disorders and post-laser, light or chemical-treatment management. However, such compositions are still not as durable as desired, and require more than one application per day.

Accordingly, there remains a need for compositions, devices and methods for modifying skin function that form quickly and that are thin, durable, non-invasive, easy to use, and with skin-like properties.

SUMMARY OF THE INVENTION

The present invention is based, at least in part, on the discovery of durable, natural looking, non-invasive compositions, and methods for using such compositions in treating conditions of compromised skin barrier function. The present invention provides safe compositions that can form a covering, a layer, a film, a device, or a prosthetic skin, which allows enhancement and/or reestablishment of one or more skin barrier functions.

The present compositions are distinct from prior compositions in that the layer formed by the present compositions have low tackiness and form quickly, resulting in a wearable, comfortable (maintains temperature and humidity similar to normal, healthy skin), breathable, thin, optically invisible, cosmetically elegant, flexible, stretchable, elastic and body-movement conforming, yet long-lasting covering, layer, film, or device on the outside of the body (e.g., over skin or any other body surface). The present inventions provide novel compositions that are longer lasting and perform better than prior compositions, particularly during more demanding activities, for example, exercising, showering and swimming (in sea-water, fresh water or chlorinated water), steam room (heat at high humidity), and sauna (heat at low humidity).

In particular, the covering, layer, film or device formed from the compositions disclosed herein regulates transdermal transport properties of skin. In one aspect, the covering, layer, film or device helps maintain skin hydration by reducing water vapor loss from the body. In another aspect, the covering, layer, film or device helps protect the body from external assaults, such as environmental factors (e.g., heat, cold, wind, water, humidity, bodily fluids (e.g., blood, pus/liquor puris, urine, saliva, sputum, tears, semen, milk, or vaginal secretion), sebum, saline, seawater, soapy water, detergent water, or chlorinated water), pathogens, allergens, and pruritogens. In another aspect, the covering, layer, film or device helps maintain conditions conducive to skin repair during new skin layer formation such as wound-healing that minimize scar formation. In another aspect, the covering, layer, film or device is used to treat conditions of compromised skin barrier function, including dermatological disorders, skin conditions, and wounds. In another aspect, the covering, layer, film or device is used to treat symptoms of conditions of compromised skin barrier function, such as itchy skin, dry skin, crusting, blistering, or cracking skin, dermatitis, skin edema, skin lesion formation. In another aspect, the covering, layer, film or device is used to deliver an agent to a subject to treat a condition of compromised skin barrier function, or to treat a symptom of such a condition.

The covering, layer, film or device formed by the present compositions is unobtrusive to normal activities of the wearer and is convenient (only one application is required for about 24 hours or more, up to about a week), affording localized and prolonged skin hydration and other therapeutic, aesthetic, and/or cosmetic benefits.

The covering, layer, film or device formed by the present compositions has the appearance of normal, healthy skin of the subject, thus conveying cosmetic benefits by masking, concealing, covering, or reducing the appearance of conditions of compromised skin barrier function, symptoms of compromised skin barrier function, and/or skin imperfections. The covering, layer, film or device formed by the present compositions may further comprise various colors, pearlescents, patterns or designs, thus conveying make up, cosmetic, aesthetic, and/or decorative benefits.

BRIEF DESCRIPTION OF THE FIGURES

FIG. 9 is a photoset illustrating in-vivo evaluation of optical modification of skin achieved by P1-030/P2-021: (top) on the coverage of natural hyperpigmentation, (bottom) on the coverage of tattoo.

FIG. 17 is an exemplary form used for clinical measurement of Psoriasis Area and Severity Index (PASI) Score.

DETAILED DESCRIPTION OF THE INVENTION

Figure 1:
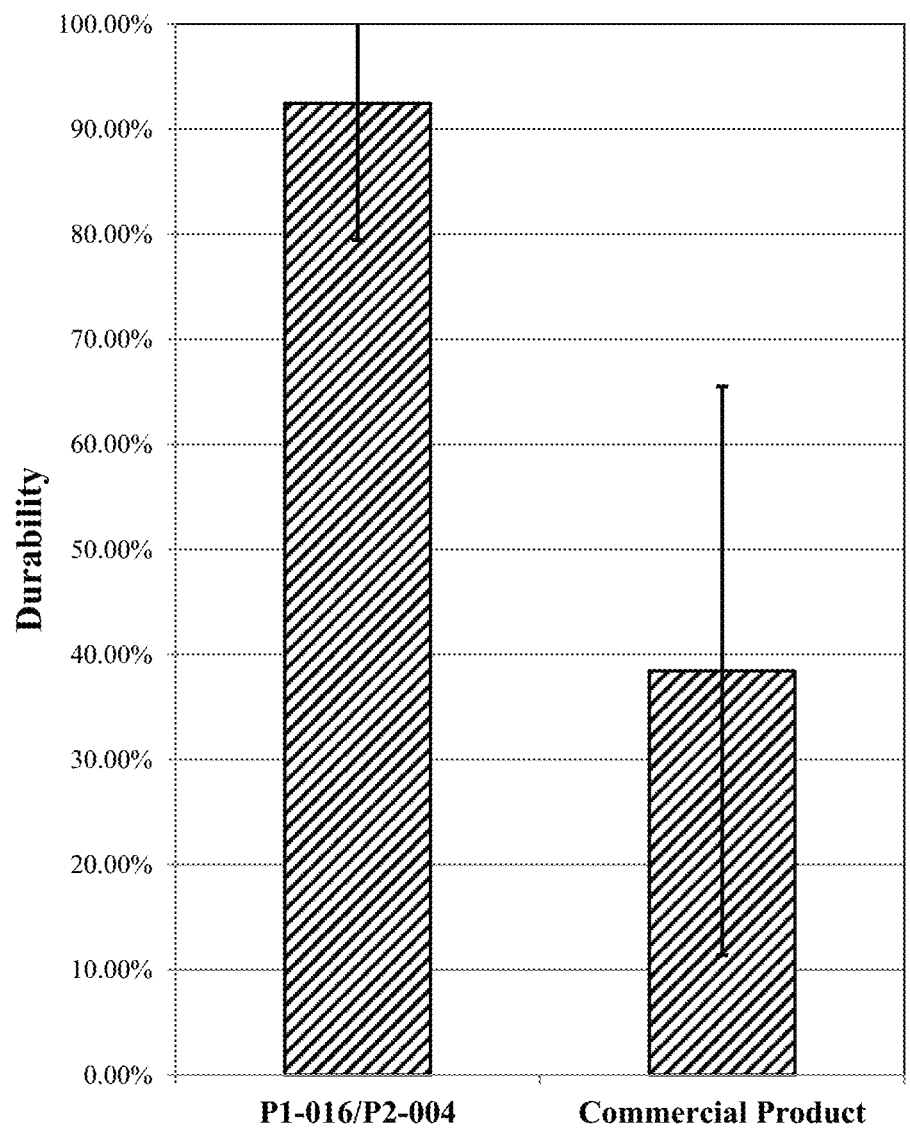
FIG. 1 is a chart illustrating the durability of layers formed from P1-016/P2-004 or a commercial product at about 24 hour time point.

Disclosed herein are compositions that can form a covering, layer, film, device, and/or prosthetic skin over the skin that have low tackiness and form quickly, resulting in a wearable, comfortable (maintains temperature and humidity similar to normal, healthy skin), breathable, thin, optically invisible, cosmetically elegant, flexible, stretchable, elastic and body-movement conforming, yet long-lasting covering, layer, film, device, and/or prosthetic skin, that can be comfortably worn to provide skin hydration and other therapeutic, aesthetic, and/or cosmetic benefits.

The present inventions provide novel compositions that are longer lasting and perform better than prior compositions, particularly during more demanding activities, for example, exercising, showering and swimming (in seawater, fresh water or chlorinated water), steam room (heat at high humidity), and sauna (heat at low humidity). An additional benefit is that the extended wearability and/or durability of the layer does not require repeated applications to sustain its benefits. The layer formed can be worn over a period of about 24 hours or more without the need to reapply.

In particular, the layer formed from the compositions disclosed herein regulates transdermal transport properties of skin, helps maintain skin hydration by providing an additional barrier over skin against water vapor loss from the body into the environment, helps protect the body against external and internal assaults, such as environmental factors (e.g., heat, cold, wind, water, humidity), bodily fluids (e.g., blood, pus/liquor puris, urine, saliva, sputum, tears, semen, milk, or vaginal secretion), sebum, saline, seawater, soapy water, detergent water, chlorinated water, pathogens, allergens, and pruritogens, and helps maintain conditions conducive to skin repair during new skin layer formation such as wound-healing that minimize scar formation.

In addition to providing increased compliance with a once-daily, or less frequent, application of aesthetically pleasing compositions, users of such compositions benefit from the therapeutic effects. The compositions and methods described herein provide a more attractive alternative to current treatment options for conditions of compromised skin barrier function.

The present compositions are suitable for easy topical application to form an aesthetically invisible, elastic, skin-conforming covering, layer, film, device, and/or prosthetic skin, which can be safely worn on the skin. Materials used in the present compositions are preferably selected from the US Food and Drug Administration's list of Generally Regarded as Safe (GRAS) substances or equivalents thereof, or are otherwise safe for skin and/or body applications.

As used herein, the term "skin" includes body surfaces where normal skin is intact, compromised, or partially or completely lost or removed. Skin further includes skin imperfections that are commonly considered to be part of "skin." Examples of skin imperfections include wrinkles, blemishes, freckles, acne, moles, warts, lesions, scars, tattoos, bruises, skin disfigurements, birth marks, sun damage, age damage, spots (e.g., aging spots), uneven skin tone, sagging skin, cellulite, stretch marks, loss of skin elasticity, skin roughness, enlarged pores, hyperpigmentation, telangiectasia, redness, shine, port wine stain (or nevus flammeus, e.g., nevus flammeus nuchae or midline nevus flammeus), and melasma. Skin further includes skin area over which any cosmetic, personal care, medical, paint, or any other foreign material, or a combination thereof, is applied.

As used herein, the term "layer" includes a covering, film, sheet, barrier, coating, membrane, device or prosthetic skin formed on, sprayed on, or spread over a surface. A layer may be, but is not necessarily, continuous. A layer may, but does not necessarily, have substantially even and/or uniform thickness.

As used herein, the terms "compromised skin barrier function," "compromised skin barrier," or "compromised skin condition" include conditions such as dermatological disorders, skin conditions, and wounds.

"Dermatological disorders" include disorders that cause at least one symptom on the skin of a subject that may require medical treatment. Dermatological disorders may be caused by, among other things, autoimmune disorders and/or environmental factors, such as allergens or chemicals. Examples of symptoms of dermatological disorders include, but are not limited to, itchy skin, dry skin, crusting, blistering, or cracking skin, dermatitis, skin edema, or skin lesion formation. Dermatological disorders include, but are not limited to, eczema, psoriasis, ichthyosis, rosacea, chronic dry skin, cutaneous lupus, lichen simplex chronicus, xeroderma, acne, disease-driven secondary dermatological disorder, and ulcer.

Eczema includes, e.g., atopic eczema, atopic dermatitis, contact dermatitis, phototoxic dermatitis, xerotic eczema (also known as asteatotic eczema, eczema craquele or craquelatum, winter itch, or pruritus hiemalis), seborrheic dermatitis (or seborrhoeic eczema), dyshidrosis (also known as dyshidrotic eczema, pompholyx, vesicular palmoplantar dermatitis, or housewife's eczema), discoid eczema (also known as nummular eczema, exudative eczema, microbial eczema), venous eczema (also known as gravitational eczema, stasis dermatitis, varicose eczema), dermatitis herpetiformis (also known as Duhring's Disease), neurodermatitis (also known as lichen simplex chronicus, localized scratch dermatitis), autoeczematization, and retinoid-induced dermatitis.

Psoriasis includes, e.g., psoriasis vulgaris (also known as plaque psoriasis), psoriatic erythroderma, pustular psoriasis (including von Zumbusch, Palmoplantar and Acropustulosis psoriasis), drug-induced psoriasis, inverse psoriasis, seborrheic-like psoriasis and guttate psoriasis.

Ichthyosis includes, e.g., ichthyosis vulgaris, acquired ichthyosis, X-linked ichthyosis, congenital ichthyosiform erythroderma, nonbullous (nbCIE), epidermolytic hyperkeratosis (bullous ichthyosis, bCIE), Harlequin type ichthyosis, ichthyosis bullosa of Siemens, ichthyosis hystrix, Curth-Macklin type, Hystrix-like ichthyosis with deafness, Lamellar ichthyosis, type 1, Lamellar ichthyosis, type 2, Lamellar ichthyosis, type 3, Lamellar ichthyosis, type 4, Lamellar ichthyosis, type 5, CHILD Syndrome, Conradi-Hünermann syndrome, ichthyosis follicularis with alopecia and photophobia syndrome, Keratitis-ichthyosis-deafness syndrome, Netherton syndrome, Neutral lipid storage disease with ichthyosis, adult Refsum disease, ichthyosis and male hypogonadism, Sjögren-Larsson syndrome, and photosensitive trichothiodystrophy (IBIDS syndrome).

Rosacea includes, e.g., erythematotelangiectatic rosacea, papulopustular rosacea, phymatous rosacea (e.g., rhinophyma), and granulomatous rosacea.

Cutaneous lupus includes, e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus.

Acne includes, e.g., acne vulgaris, acne aestivalis, acne conglobate, acne cosmetic, acne fulminans, acne keloidalis nuchae, acne mechanica, acne medicamentosa (also known as drug-induced acne, e.g., steroid acne), acne miliaris necrotica, acne necrotica, acne rosacea, and hidradenitis suppurativa.

A "disease-driven secondary dermatological disorder" refers to a dermatological condition that may require treatment and was caused by or is associated with a non-dermatological disorder. A "non-dermatological disorder" includes disorders not primarily associated with the skin but which may result in, be associated with, or have a secondary manifestation of a skin condition, for example, a disorder of the circulatory system or metabolism of the subject. Disease-driven secondary dermatological disorders include, for example, an ulcer caused by diabetes mellitus (e.g., diabetic foot ulcer), a bacterial, viral or fungal infection, cancer, pressure (e.g., a bedsore), blood disorders, conditions affecting the nervous system (e.g., neuropathic ulcers (also known as "mal perforans")), conditions affecting the nervous system (e.g., arterial insufficiency ulcers (also known as "ischemic ulcers") or vascular ulcers), and/or a chronic wound.

"Skin conditions" include, but are not limited to, itchy skin, raw skin, dry skin, flaking or peeling skin, blisters on the skin, redness, swelling or inflammation of the skin, and oozing, scabbing or scaling skin. Skin conditions also include compromised skin barrier conditions caused by laser, light or chemical peel treatment.

"Wounds" include injuries to the skin wherein the skin is torn, cut or punctured. Wounds include open wounds, for example, abrasions, lacerations, incisions, punctures, avulsions, or amputations. Wounds also include burn wounds, a type of injury to skin and/or flesh caused by heat, electricity, wind, chemicals, light, radiation or friction.

"Treat," "treating" and "treatment" include both therapeutic and prophylactic/preventative measures. "Treat," "treating" and "treatment" further include both disorder modifying treatment and symptomatic treatment. Treatment may ameliorate or cause a reduction in the severity and/or duration of at least one symptom of the conditions of compromised skin barrier function. Treatment may also cause a complete recovery from the conditions of compromised skin barrier function.

"Apply," "applied" and "application" includes any and all known methods of contacting or administering compositions of the invention to a subject's skin or body. The application may be by finger, hand, brush, cotton ball, cotton swab, tissue, pad, sponge, roll-on, spatula, dispenser, drops, spray, splash, foam, mousse, serum, spritz, and other appropriate methods.

"Subject" includes subjects in which the compositions disclosed herein would be appropriate for use, particularly animals (e.g., a human). Subjects may further include plants, wherein skin refers to the surface over portions of the plant that may benefit from application of the composition, such as flowers, leaves, fruits, stems, branches, bark, and roots.

"In vitro" means tested or formed not on, in, or over a subject's skin or body.

"Routine daily activities" include instrumental activities of daily living, such as feeding (e.g., eating, drinking, taking medications), continence (e.g., urination and defecation), toileting, dressing, bathing (e.g., shower, bath), grooming, physical ambulation (e.g., walking, using transportation), talking (e.g., using the telephone), preparing food, housekeeping, doing laundry, shopping, and handling finances. Examples of such daily activities are described in Lawton and Brody, Assessment of older people: self-maintaining and instrumental activities of daily living, *Gerontologist* 1969 Autumn; 9(3):179-86 and Katz et al., Studies of Illness in the Aged. The Index of ADL: A Standardized Measure of Biological and Psychosocial Function, *JAMA* 1963 Sep. 21; 185:914-9.

"Demanding activities" include activities that generate elevated level of strain and/or stress on the skin of a subject as compared to the strain or stress generated by routine daily activities. Examples of such demanding activities include exercising, swimming (in sea-water, fresh water or chlorinated water), steam room (heat at high humidity), sauna (heat at low humidity), and other like activities.

Unless otherwise stated, descriptions of any material used as part of any composition disclosed herein are of such material as an ingredient of the composition prior to mixing, combination and/or reaction of such material with other ingredient(s) of the composition.

One aspect of the invention is directed to a composition comprising at least one crosslinkable polymer. A "crosslinkable polymer" refers to a polymer that can physically or chemically interact, or both physically and chemically interact, with itself or with other polymers to form a layer on a surface (e.g., skin, leather, glass, plastic, metal) to which it is applied. "Physically interact" refers to the formation of non-covalent interaction (e.g., hydrogen bonds, or electrostatic, polar, ionic, van der Waals, or London forces) between two or more polymer chains. "Chemically interact" refers to the formation of covalent bonds between two or more polymer chains. Covalent bonds may be formed through chemical reactions that occur spontaneously or are initiated by, for example, catalyst, moisture, heat, pressure, change in pH, or radiation. The crosslinkable polymer(s) may be homopolymer or copolymer, for example, random copolymer, alternating copolymer, periodic copolymer, statistical copolymer, block copolymer, graft or grafted copolymer, or a combination thereof.

In certain embodiments, the composition comprises one or more physically crosslinkable polymers such as semi-crystalline polymers, charged polymers, polymers with hydrogen-bond capable linkages, or polymers capable of forming phase-separation networks (e.g., poly(styrene-butadiene), poly(dimethylsiloxane-ethyleneoxide)). In preferred embodiments, the composition comprises one or more physically crosslinkable polymers that can form hydrogen-bond crosslinking networks and/or ionic crosslinking networks, non-limiting examples of which include copolymers among two or more of the following: caprolactone, lactide, glycolide, sebacic, adipic, and trimethylene carbonate. In further preferred embodiments, the composition comprises one or more biological crosslinkable polymers, non-limiting examples of which include one or more of the following: protein-based polymers such as keratin, elastin, collagen; or sugar-based polymers such as chitin, chitosan, cellulose, starch; or lipid-based polymers such as ceramide, triglyceride, sphingosine or a combination thereof.

In certain embodiments, the composition comprises one or more chemically crosslinkable polymers such as polymers containing functional groups capable of performing addition polymerization, chain-growth polymerization, step-growth polymerization, ring-opening polymerization, radical polymerization, anionic polymerization, cationic polymerization, condensation polymerization, living polymerization, photopolymerization, radiation polymerization or other chemical reactions that form one or more chemical bonds. In preferred embodiments, the composition comprises one or more chemically crosslinkable polymers that can form covalent crosslinking networks. In further preferred embodiments, the composition comprises one or more chemically crosslinkable polymers selected from polysiloxane, polyethylene oxide, polypropylene oxide, polyurea, polycarbonate, polyglycerol, polyurethane, polyester (including, but not limited to, polylactic-co-glycolic acid, polycaprolactone, polylactic acid, polyglycolic acid, and polyhydroxybutyrate, polyamide), polysulfone, polyphosphate, polyamine, polyimine, polythiol, polyboron, or a combination thereof.

In certain embodiments, the composition comprises one or more both physically and chemically crosslinkable polymers. In preferred embodiments, the composition comprises one or more both physically and chemically crosslinkable polymers such as keratin, elastin, collagen, or a combination thereof.

In preferred embodiments, the composition comprises one or more crosslinkable organopolymer(s). An "organopolymer" refers to a polymer that includes carbon.

In certain embodiments, the composition comprises: Polymer A) one or more organopolymer(s) having on average at least two carbon double bonds (i.e., alkenyl-functional group) or at least one carbon triple bond (i.e., alkynyl-functional group) within each molecule; and Polymer B) one or more organopolysiloxane(s) having on average at least two Si-hydrogen-containing monomer units (Si—H units) within each molecule.

In preferred embodiments, the organopolymer comprises organopolysiloxanes, which are polymers based upon the following monomer units:

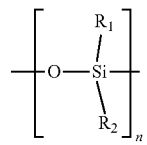

Formula I and terminal units:

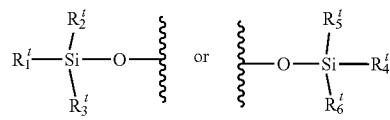

Formula II wherein each $R_1$, $R_2$, and $R^t_1$-$R^t_6$ is independently selected from hydrogen, $C_{1-25}$ alkyl, $C_{2-25}$ alkenyl, $C_{2-25}$ alkynyl, $C_{5-10}$ aryl, halogen, amino and hydroxy, wherein the $C_{1-25}$ alkyl, $C_{2-25}$ alkenyl, $C_{2-25}$ alkynyl, and $C_{5-10}$ aryl may be optionally substituted with 1 to 3 substituents selected from $C_{1-25}$ alkyl, halogen, halo$C_{1-25}$ alkyl, amino and hydroxy, and wherein n is an integer between 10 and 3000. $R_1$ and $R_2$ of each monomer unit may be, but are not necessarily the same.

As used herein, "alkyl," "alkenyl" and "alkynyl" include both straight-chain and branched hydrocarbon groups. As used herein, "amino" includes both primary amines such as —NH2 and secondary or tertiary amines wherein one or both of the hydrogen atoms have been replaced with an alkyl group. Non-siloxane repeat units may be present in the polymer backbone of organopolysiloxane.

In preferred embodiments, $R^t_1$ and $R^t_4$ are alkenyl or alkynyl and each $R_1$, $R_2$, $R^t_2$ $R^t_3$, $R^t_5$, and $R^t_6$ is independently selected from $C_{1-25}$ alkyl, $C_{5-10}$ aryl, halogen, amino and hydroxy, wherein the $C_{1-25}$ alkyl, $C_{2-25}$ alkenyl, and $C_{5-10}$ aryl may be optionally substituted with 1 to 3 substituents selected from $C_{1-25}$ alkyl, halogen, halo$C_{1-25}$ alkyl, amino and hydroxy. In further preferred embodiments, $R^t_1$ and $R^t_4$ are alkenyl or alkynyl and each $R_1$, $R_2$, $R^t_2$ $R^t_3$, $R^t_5$, and $R^t_6$ is independently $C_{1-25}$ alkyl optionally substituted with 1 to 3 substituents selected from halogen or halo$C_{1-25}$ alkyl.

In certain embodiments, $R^t_1$ and $R^t_4$ are hydrogen and each $R_1$, $R_2$, $R^t_2$ $R^t_3$, $R^t_5$, and $R^t_6$ is independently selected from $C_{1-25}$ alkyl, $C_{5-10}$ aryl, halogen, amino and hydroxy, wherein the $C_{1-25}$ alkyl, and $C_{5-10}$ aryl may be optionally substituted with 1 to 3 substituents selected from $C_{1-25}$ alkyl, halogen, halo$C_{1-25}$ alkyl, amino and hydroxy. In preferred embodiments, each $R_1$, $R_2$, and $R^t_1$-$R^t_6$ is independently selected from hydrogen, $C_{1-25}$ alkyl, $C_{5-10}$ aryl, halogen, amino and hydroxy, wherein the $C_{1-25}$ alkyl, and $C_{5-10}$ aryl may be optionally substituted with 1 to 3 substituents selected from $C_{1-25}$ alkyl, halogen, halo$C_{1-25}$ alkyl, amino and hydroxyl. In a preferred embodiment, the Si—H units in the organopolysiloxane are spaced on average by at least about 1 monomer units, about 2 monomer units, about 5 monomer units, about 10 monomer units, about 20 monomer units, about 40 monomer units, about 200 monomer units, about 400 monomer units, about 1,000 monomer units, or about 2,000 monomer units.

In certain embodiments, the organopolysiloxane is primarily comprised of siloxane monomer units, i.e., substantially all of the repeat units along the polymer backbone are siloxane units. In preferred embodiments, the organopolysiloxane comprises greater than 90%, greater than 95%, greater than 98%, or greater than 99% siloxane repeat units along the polymer backbone.

In certain embodiments, the Si—H to alkenyl (e.g., vinyl) or Si—H to alkynyl molar ratio of the polymers in the composition is about 1:5 to about 60:1; about 10:1 to about 30:1; or about 20:1 to about 25:1.

In preferred embodiments, the composition comprises: Polymer A) one or more organopolysiloxane(s) having on average at least two carbon double bonds or at least one carbon triple bond within each molecule; and Polymer B) one or more organopolysiloxane(s) having on average at least two Si—H units within each molecule.

In preferred embodiments, the composition further comprises one or more reinforcing component(s). In certain embodiments, the reinforcing component is selected from surface treated carbon, silver, mica, zinc sulfide, zinc oxide, titanium dioxide, aluminum oxide, clay (e.g., $Al_2O_3$, $SiO_2$), chalk, talc, calcite (e.g., $CaCO_3$), barium sulfate, zirconium dioxide, polymer beads and silica (e.g., silica aluminates, calcium silicates, or surface treated silica (e.g., fumed silica, hydrated silica, or anhydrous silica)), or a combination thereof. Such reinforcing components reinforce the physical properties of the layer as discussed herein. In preferred embodiments, the reinforcing component is surface treated silica, for example, silica treated with hexamethyldisilazane, polydimethylsiloxane, hexadecylsilane or methacrylsilane. In further preferred embodiments, the reinforcing component is fumed silica, including fumed silica having been surface treated with hexamethyldisilazane.

In certain embodiments, the particles of the reinforcing component have an average surface area of between about 50 and about 500 $m^2/g$. In preferred embodiments, the particles of the reinforcing component have an average surface area of between about 100 and about 350 $m^2/g$. In further preferred embodiments, the particles of the reinforcing component have an average surface area of between about 135 and about 250 $m^2/g$. In certain embodiments, the reinforcing component has an average particle diameter of between about 1 nm and about 20 In preferred embodiments, the reinforcing component has an average particle diameter of between about 2 nm and about 1 and further preferably between about 5 nm and about 50 nm.

In preferred embodiments, the composition comprises about 5 to about 90% by weight Polymer A; about 5 to about 75% by weight Polymer B; and about 0 to about 25% by weight reinforcing component. In further preferred embodiments, the composition comprises about 50 to about 90% by weight Polymer A; about 5 to about 30% by weight Polymer B; and about 5 to about 15% by weight reinforcing component.

In certain embodiments, the organopolysiloxane having carbon double or triple bonds includes such carbon double or triple bonds at terminal units of the polymer, in non-terminal monomer units of the polymer, or a combination thereof. In preferred embodiments, the organopolysiloxane having carbon double or triple bonds includes such carbon double or triple bonds in non-terminal monomer units of the polymer. In preferred embodiments, the carbon double bond-containing monomer units in the organopolysiloxane are spaced on average by at least about 40 monomer units, about 200 monomer units, about 400 monomer units, about 1,000 monomer units, or about 2,000 monomer units.

In certain embodiments, the organopolysiloxane having carbon double or triple bonds has a weight percent of carbon double/triple bond-containing monomer units of between about 0.01 and about 2%, and preferably, between about 0.03 and about 0.6%. In certain embodiments, the organopolysiloxane having carbon double or triple bonds has a vinyl equivalent per kilogram of between about 0.005 and about 0.5, and preferably, between about 0.01 and about 0.25. An approximate molar amount of the carbon double/triple bonds in the organopolysiloxane can be calculated based on the average molecular weight of the organopolysiloxane.

In certain embodiments, the organopolysiloxane having Si—H units includes such Si—H units at terminal units of the polymer, in non-terminal monomer units of the polymer, or a combination thereof. In preferred embodiments, the organopolysiloxane having Si—H units includes such Si—H units in non-terminal monomer units of the polymer. In preferred embodiments, the Si—H-containing monomer units in the organopolysiloxane are spaced on average by at least about 1 monomer units, about 2 monomer units, about 5 monomer units, about 10 monomer units, about 20 monomer units, about 40 monomer units, about 200 monomer units, about 400 monomer units, about 1,000 monomer units, or about 2,000 monomer units.

In certain embodiments, the organopolysiloxane having Si—H units has a weight percent of Si—H-containing monomer units of between about 0.003 and about 50%, and preferably, between about 0.01 and about 25%. In certain embodiments, the organopolysiloxane having Si—H units has an Si—H content of between about 0.1 mmol/g and about 20 mmol/g, about 0.5 mmol/g and about 10 mmol/g, and preferably, between about 1 mmol/g and about 5 mmol/g. An approximate molar amount of the Si—H units in the organopolysiloxane can be calculated based on the average molecular weight of the organopolysiloxane. Average molecular weight, or molar mass, of the ingredients disclosed herein are commonly provided by the supplier of the ingredients, expressed in units of Dalton (Da) or its equivalent g/mol.

The term "viscosity" refers to the measure of the resistance of a fluid which is being deformed by either shear stress or tensile stress. The viscosity of the composition affects the thickness, spreadability, and evenness and/or uniformity of the layer formed on a substrate. Viscosity may be reported as either dynamic viscosity (also known as absolute viscosity, typical units Pa·s, Poise, P, cP) or kinematic viscosity (typical units $cm^2/s$, Stokes, St, cSt), which is the dynamic viscosity divided by density of the fluid measured. Viscosity ranges of the ingredients disclosed herein are commonly provided by the supplier of the ingredients in units of kinematic viscosity (e.g., cSt), as measured using a Rheometer or a Cannon-Fenske Tube Viscometer.

Viscosity of a fluid can be measured in vitro, for example, using a rheometer (e.g., linear shear rheometer or dynamic shear rheometer) or a viscometer (also called viscosimeter, e.g., capillary viscometer or rotational viscometer), at an instrument specific strain. For example, Thomas G. Mezger, The Rheology Handbook: For Users of Rotational and Oscillatory Rheometers (2nd Ed.), Vincentz Network, 2006, and American Society for Testing and Materials (ASTM) standards such as ASTM D3835-08, ASTM D2857-95, ASTM D2196-10, and ASTM D2983-09 provide instructions on how to measure the viscosity of a fluid. Viscosity of a fluid is preferably measured in vitro using the Rheometer Viscosity Measurement Test described herein. Density of the fluid may vary with temperature or pressure. Unless otherwise specified, all properties of compositions, layers and/or devices disclosed herein, including viscosity, are measured at room temperature (about 25° C.) and about 1 atmosphere air pressure.

In certain embodiments, the composition has a viscosity above about 100 cP and below about 1,000,000 cP at about 25° C. In certain embodiments, the composition has a viscosity below about 750,000 cP, below about 500,000 cP, or below about 250,000 cP at about 25° C. In preferred embodiments, the composition has a viscosity below about 200,000 cP, below about 175,000 cP, below about 150,000 cP, below about 125,000 cP, below about 100,000 cP, or below about 80,000 cP at about 25° C. In certain embodiments, the composition has a viscosity above about 100 cP, above about 500 cP, or above about 1000 cP at about 25° C. In preferred embodiments, the composition has a viscosity above about 2000 cP, above about 5000 cP, above about 7500 cP, or above about 10,000 cP at about 25° C. In further preferred embodiments, the composition has a viscosity above about 15,000 cP at about 25° C.

In preferred embodiments, the composition comprises: Polymer A) one or more organopolysiloxane(s) having on average at least two alkenyl-functional groups and having a viscosity of about 10,000 to about 2,000,000 cSt at about 25° C.; Polymer B) one or more organopolysiloxane(s) having on average at least two Si—H units and having a viscosity of about 2 to about 100,000 cSt at about 25° C.; and, optionally, Polymer C) one or more organopolysiloxane(s) having on average at least one alkenyl-functional groups and having a viscosity of about 0.7 to about 10,000 cSt at about 25° C.

In certain embodiments, the molar ratio of Si—H functional group from Polymer B to alkenyl-functional group from Polymer A is from about 60:1 to about 1:5. In preferred embodiments, the molar ratio of Si—H functional group from Polymer B to alkenyl-functional group from Polymer A is about 45:1 to about 15:1. In certain embodiments, the molar ratio of Si—H functional group from Polymer B to alkenyl-functional group from Polymer C is from about 60:1 to about 1:5. In preferred embodiments, the molar ratio of Si—H functional group from Polymer B to alkenyl-functional group from Polymer C is about 45:1 to about 15:1. In certain embodiments, the molar ratio of alkenyl-functional group from Polymer A to alkenyl-functional group from Polymer C is about 100:1 to about 1:100. In preferred embodiments, the molar ratio of alkenyl-functional group from Polymer A to alkenyl-functional group from Polymer C is about 10:1 to about 1:10.

In certain embodiments, Polymer A has a viscosity between about 10,000 and about 2,000,000 cSt at about 25° C. In preferred embodiments, Polymer A has a viscosity above about 20,000, above about 40,000, above about 60,000, above about 80,000, or above about 100,000 cSt at about 25° C. In further preferred embodiments, Polymer A has a viscosity above about 125,000 or above about 150,000 cSt at about 25° C. In preferred embodiments, Polymer A has a viscosity below about 1,000,000 cSt, below about 500,000 cSt, below about 450,000, below about 400,000, below about 350,000, below about 300,000, or below about 250,000 cSt at about 25° C. In further preferred embodiments, Polymer A has a viscosity below about 200,000 or below about 180,000 cSt at about 25° C. In further preferred embodiments, Polymer A has a viscosity of about 165,000 cSt at about 25° C.

In certain embodiments, Polymer A has an average molecular weight between about 60,000 Da and about 500,000 Da. In preferred embodiments, Polymer A has an average molecular weight above about 72,000 Da, about 84,000 Da, about 96,000 Da, or about 100,000 Da. In further preferred embodiments, Polymer A has an average molecular weight above about 140,000 Da, or about 150,000 Da. In preferred embodiments, Polymer A has an average molecular weight below about 200,000 Da, below about 190,000 Da, about 180,000 Da, or about 170,000 Da. In further preferred embodiments, Polymer A has an average molecular weight below about 160,000 Da. In further preferred embodiments, Polymer A has an average molecular weight of about 155,000 Da.

In certain embodiments, Polymer B has a viscosity between about 2 to about 500,000 cSt at about 25° C. In preferred embodiments, Polymer B has a viscosity above about 3 cSt, above about 4 cSt, or above about 12 cSt at about 25° C. In further preferred embodiments, Polymer B has a viscosity above about 40 cSt at about 25° C. In preferred embodiments, Polymer B has a viscosity below about 200,000, below about 100,000, below about 50,000, below about 20,000, below about 10,000, below about 5,000, below about 2,000, or below about 1,000 cSt at about 25° C. In further preferred embodiments, Polymer B has a viscosity below about 500 cSt at about 25° C. In further preferred embodiments, Polymer B has a viscosity between about 45 to about 100 cSt at about 25° C.

In certain embodiments, Polymer B has an average molecular weight between about 400 and about 500,000 Da. In preferred embodiments, Polymer B has an average molecular weight above about 500 Da, about 800 Da, about 1,200 Da, or about 1,800 Da. In further preferred embodiments, Polymer B has an average molecular weight above about 2,000 Da. In preferred embodiments, Polymer B has an average molecular weight below about 250,000 Da, below about 140,000 Da, below about 100,000 Da, below about 72,000 Da, below about 62,700 Da, below about 49,500 Da, below about 36,000 Da, or below about 28,000 Da. In further preferred embodiments, Polymer B has an average molecular weight below about 17,200 Da. In further preferred embodiments, Polymer B has an average molecular weight between about 2,200 Da and 6,000 Da.

In certain embodiments, Polymer C has a viscosity of between about 0.7 cSt to about 10,000 cSt at about 25° C. In preferred embodiments, Polymer C has a viscosity of above about 1 cSt, above about 6 cSt, above about 10 cSt, above about 20 cSt, above about 50 cSt, or above about 100 cSt at about 25° C. In further preferred embodiments, Polymer C has a viscosity of above about 200 cSt at about 25° C. In preferred embodiments, Polymer C has a viscosity of below about 5,000 cSt, about 4,000 cSt, below about 2,000 cSt, or below about 1,000 cSt at about 25° C. In further preferred embodiments, Polymer C has a viscosity of below about 500 cSt at about 25° C. In further preferred embodiments, Polymer C has a viscosity of about 250 cSt at about 25° C.

In certain embodiments, Polymer C has an average molecular weight between about 180 Da and about 65,000 Da. In preferred embodiments, Polymer C has an average molecular weight above about 500 Da, about 800 Da, about 1,500 Da, about 3,000 Da, or about 6,000 Da. In further preferred embodiments, Polymer C has an average molecular weight above about 9,400 Da. In preferred embodiments, Polymer C has an average molecular weight below about 50,000 Da, about 45,000 Da, or about 30,000 Da. In further preferred embodiments, Polymer C has an average molecular weight below about 17,500 Da. In further preferred embodiments, Polymer C has an average molecular weight of about 10,000 Da.

In preferred embodiments, Polymers A and C are each independently selected from vinyl terminated polydimethylsiloxane, vinyl terminated diphenyl siloxane-dimethylsiloxane copolymers, vinyl terminated polyphenylmethylsiloxane, vinylphenylmethyl terminated vinylphenylsiloxane-phenylmethylsiloxane copolymer, vinyl terminated trifluoropropylmethylsiloxane-dimethylsiloxane copolymer, vinyl terminated diethyl siloxane-dimethylsiloxane copolymer, vinylmethylsiloxane-dimethylsiloxane copolymer, trimethylsiloxy terminated, vinylmethylsiloxane-dimethylsiloxane copolymers, silanol terminated, vinylmethylsiloxane-dimethylsiloxane copolymers, vinyl terminated, vinyl gums, vinylmethylsiloxane homopolymers, vinyl T-structure polymers, vinyl Q-structure polymers, unsaturated organopolymers (non-limiting examples of which include one or more of unsaturated fatty alcohols, unsaturated fatty acids, unsaturated fatty esters, unsaturated fatty amide, unsaturated fatty urethane, unsaturated fatty urea, ceramide, cocetin, lecithin and sphingosine), monovinyl terminated polydimethylsiloxanes, vinylmethylsiloxane terpolymers, vinylmethoxysilane homopolymers, vinyl terminated polyalkylsiloxane polymers, vinyl terminated polyalkoxysiloxane polymers and combinations thereof. In further preferred embodiments, Polymers A and C are each vinyl dimethicone.

In preferred embodiments, Polymer B is selected from hydride terminated polydimethylsiloxane, hydride terminated polyphenyl-(dimethylhydrosiloxy)siloxane, hydride terminated methylhydrosiloxane-phenylmethylsiloxane copolymer, trimethylsiloxy terminated methylhydrosiloxane-dimethylsiloxane copolymers, polymethylhydrosiloxanes, trimethylsiloxy terminated, polyethylhydrosiloxane, triethylsiloxane, methylhydrosiloxane-phenyloctylmethylsiloxane copolymer, methylhydrosiloxane-phenyloctylmethylsiloxane terpolymer, and combinations thereof. In further preferred embodiments, Polymer B is hydrogen dimethicone.

In certain embodiments, the composition is a two-part composition comprising a first part and a second part. In preferred embodiments, the first part comprises Polymers A and B. In preferred embodiments, the first part further comprises one or more reinforcing component(s). In preferred embodiments, the second part comprises Polymer C.

In certain embodiments, the weight ratio of polymers to reinforcing component is about 100:1 to about 1:1. In the preferred embodiments, the weight ratio of polymers to reinforcing component is about 50:1 to about 2:1. In further preferred embodiments, the weight ratio of polymers to reinforcing component is about 15:1 to about 3:1. In more preferred embodiments, the weight ratio of polymers to reinforcing component is about 10:1 to about 4:1. In even more preferred embodiments, the weight ratio of polymers to reinforcing component is about 7:1 to about 8:1.

In preferred embodiments, the first part comprises about 5 to about 90% by weight Polymer A; about 5 to about 75% by weight Polymer B; and about 0 to about 25% by weight reinforcing component. In further preferred embodiments, the first part comprises about 50 to about 90% by weight Polymer A; about 5 to about 30% by weight Polymer B; and about 5 to about 15% by weight reinforcing component.

081 In certain embodiments, the composition further comprises a catalyst that facilitates crosslinking of the one or more crosslinkable polymers. In case of a two-part composition, in certain embodiments, the second part further comprises one or more catalyst(s) that facilitates crosslinking of the one or more crosslinkable polymers. "Catalyst" includes any substance that causes, facilitates, or initiates a physical and/or chemical crosslinking reaction. The catalyst may or may not undergo permanent physical and/or chemical changes during or at the end of the process. In preferred embodiments, the catalyst is a metal catalyst capable of initiating and/or facilitating the crosslinking at or below body temperature, for example, Group VIII metal catalysts, such as platinum, rhodium, palladium, cobalt, nickel, ruthenium, osmium and iridium catalysts, and Group IVA metal catalysts, such as germanium and tin. In further preferred embodiments, the catalyst is a platinum catalyst, a rhodium catalyst or a tin catalyst. Examples of platinum catalysts include, for example, platinum carbonyl cyclovinylmethylsiloxane complexes, platinum divinyltetramethyldisiloxane complexes, platinum cyclovinylmethylsiloxane complexes, platinum octanaldehyde/octanol complexes, and other Pt(0) catalysts such as Karstedt's catalyst, platinum-alcohol complexes, platinum-alkoxide complexes, platinum-ether complexes, platinum-aldehyde complexes, platinum-ketone complexes, platinum-halogen complexes, platinum-sulfur complexes, platinum-nitrogen complexes, platinum-phosphorus complexes, platinum-carbon double-bond complexes, platinum carbon triple-bond complexes, platinum-imide complexes, platinum-amide complexes, platinum-ester complexes, platinum-phosphate ester complexes, platinum-thiol ester complexes, platinum lone-pair-electron complexes, platinum-aromatic complexes, platinum π-electron complexes, and combinations thereof. Examples of rhodium catalyst include tris (dibutylsulfide) rhodium trichloride and rhodium trichloride hydrate. Examples of tin catalysts include tin II octoate, tin II neodecanoate, dibutyltin diisooctylmaleate, Di-n-butylbis(2,4 pentanedionate)tin, di-n-butylbutoxychlorotin, dibutyltin dilaurate, dimethyltin dineodecanoate, dimethylhydroxy(oleate)tin and tin II oleate. In preferred embodiments, the catalyst is platinum catalyst. In further preferred embodiments, the catalyst is platinum divinyltetramethyldisiloxane complexes.

In preferred embodiments, the composition comprises about 0.001 to about 1% by weight (i.e., about 10 ppm to about 10,000 ppm), preferably about 0.005 to about 0.05% by weight (i.e., about 50 ppm to about 500 ppm) catalyst. In further preferred embodiments, the composition comprises about 0.01 to about 0.03% by weight catalyst.

In certain embodiments, the composition is a two-part composition, comprising a first part comprising polymer(s) A and Polymer B; and a second part comprising polymer(s) C and one or more catalyst(s).

In certain embodiments, the composition is a two-part composition, comprising a first part comprising polymer(s) A and polymer(s) C and one or more catalyst(s); and a second part comprising Polymer B.

In certain embodiments, the composition is a two-part composition, comprising a first part comprising polymer(s) A and one or more catalyst(s); and a second part comprising Polymer B and polymer(s) C.

In certain embodiments, the composition is a two-part composition, comprising a first part comprising Polymer B and polymer(s) C; and a second part comprising polymer(s) A and one or more catalyst(s).

In preferred embodiments, the second part comprises about 0.005 to about 0.05% by weight catalyst. In further preferred embodiments, the second part comprises about 0.01 to about 20% by weight Polymer C; and about 0.005 to about 0.05% by weight catalyst. In further preferred embodiments, the second part comprises about 0.5 to about 10% by weight Polymer C; and about 0.01 to about 0.03% by weight catalyst.

In certain embodiments, the first part is applied over skin prior to application of the second part, and a layer is formed after the second part is applied over the first part. In certain embodiments, the second part is applied over skin prior to application of the first part, and a layer is formed after the first part is applied over the second part. In certain embodiments, the first part is applied over skin together with the second part, and a layer is formed after both compositions are applied. In certain embodiments, the first part and the second part are mixed together and then applied over the skin, and a layer is formed after the mixture is applied. In preferred embodiments, the first part is gently spread over an area of skin of the subject, the second part is gently spread over the first part, covering the entire first part area.

In certain embodiments, the ratio of weight or volume amount of the first part to the second part is about 5:1 to about 1:20. In preferred embodiments, the ratio of weight or volume amount of the first part to the second part is about 2:1 to about 1:2. In further preferred embodiments, the ratio of weight or volume amount of the first part to the second part is about 1:1.

Anhydrous compositions generally have longer shelf-life than emulsions with similar ingredients, without the need for preservatives against bacteria or mold. "Anhydrous" as used herein refers to containing as an ingredient less than about 10%, less than about 5%, less than about 2%, less than about 1%, or less than about 0.1% water. In some embodiments, the composition is anhydrous. In some embodiments, the composition is an emulsion. In some embodiments, the composition is a dispersion. In some embodiments, the composition is a suspension. In some embodiments, the composition is a paste. In some embodiments, the composition is a semi-solid. In some embodiments, the composition is an ointment. In some embodiments, the composition is a cream. In some embodiments, the composition is a serum. In some embodiments, the composition is a lotion. In some embodiments, the composition is a patch. In certain embodiments, the composition can be spread, sprayed, stenciled stamped, patterned, patched, transferred, layered, covered or spritzed over skin.

In certain embodiments, the first part is anhydrous. Alternatively, the first part is an emulsion. In certain embodiments, the first part can be spread, sprayed or spritzed over skin.

In certain embodiments, the second part is anhydrous. Alternatively, the second part is an emulsion. In certain embodiments, the second part can be spread, sprayed or spritzed over skin.

In certain embodiments, the first part has a viscosity above about 100 cP, above about 500 cP, or above about 1000 cP at about 25° C. In preferred embodiments, the first part has a viscosity above about 2000 cP, above about 5000 cP, above about 7500 cP, or above about 10,000 cP at about 25° C. In further preferred embodiments, the first part has a viscosity above about 15,000 cP at about 25° C. In certain embodiments, the first part has a viscosity below about 1,000,000 cP, below about 750,000 cP, below about 500,000 cP, or below about 250,000 cP at about 25° C. In preferred embodiments, the first part has a viscosity below about 200,000 cP, below about 175,000 cP, below about 150,000 cP, below about 125,000 cP, below about 100,000 cP, or below about 80,000 cP at about 25° C.

In certain embodiments, the second part has a viscosity above about 100 cP, above about 500 cP, or above about 1000 cP at about 25° C. In preferred embodiments, the second part has a viscosity above about 2000 cP, above about 5000 cP, above about 7500 cP, or above about 10,000 cP at about 25° C. In further preferred embodiments, the second part has a viscosity above about 15,000 cP at about 25° C. In certain embodiments, the second part has a viscosity below about 1,000,000 cP, below about 750,000 cP, below about 500,000 cP, below about 250,000 cP, below about 200,000 cP, or below about 175,000 cP at about 25° C. In preferred embodiments, the second part has a viscosity below about 150,000 cP, below about 125,000 cP, or below about 100,000 cP at about 25° C. In further preferred embodiments, the second part has a viscosity below about 80,000 cP at about 25° C.

In certain embodiments, the composition further comprises one or more additives. In certain embodiments, the first part and/or the second part further independently comprise(s) one or more additives. Suitable additives include, but are not limited to, feel modifiers, tack modifiers, spreadability enhancers, diluents, adhesion modifiers, volatile siloxanes, emulsifiers, emollients, surfactants, thickeners, solvents, film formers, humectants, preservatives, pigments, skin permeation enhancers, optic modifiers, gas transport modifiers, liquid transport modifiers, pH modifiers, sensitizing modifiers, aesthetic modifiers, and a combination thereof. Additional suitable additives are disclosed in the International Nomenclature Cosmetic Ingredient (INCI) dictionary, which is incorporated herein by reference in its entirety. In preferred embodiments, the emulsifiers are alkoxydimethicone, alkyldimethicone, amodimethicone, sulfodimethicone, phosphodimethicone, borodimethicone, halodimethicone, fluorodimethicone, chlorodimethicone, bromodimethicone, charged dimethicone, and a combination thereof.

In certain embodiments, the composition further comprises one or more additional agents. In certain embodiments, the first part and/or the second part further independently comprise(s) one or more additional agents, including cosmetic agents, therapeutic agents, stimuli-responsive agents, sensing agents, drug-delivery agents, optical agents, coloring agents, pigments, scattering agents, sorbing agents, temperature-active agents, heat-active agents, UV-active agents, light-active agents, sound-active agents, pressure-active agents, motion-active agents, radioactive agents, electrical agents, magnetic agents, and other beneficial agents.

Suitable cosmetic agents include, but are not limited to, moisturizers, sunscreens, UV protecting agents, skin-protectant agents, skin-soothing agents, skin-lightening agents, skin-brightening agents, skin-softening agents, skin-smoothening agents, skin-bleaching agents, skin-exfoliating agents, skin-tightening agents, cosmeceutical agents, vitamins, anti-oxidants, cell-signaling agents, cell-modulating agents, cell-interacting agents, skin tanning agents, anti-aging agents, anti-wrinkle agents, spot reducers, alpha-hydroxy acids, beta-hydroxy acids, ceramides, and a combination thereof.

Suitable therapeutic agents include, but are not limited to, pain-relievers, analgesics, anti-itching agents, anti-acne agents (beta-hydroxy acids, salicylic acid, benzoyl peroxide), anti-flammatory agents, antihistamines, corticosteroids, NSAIDs (Non-Steroidal Anti-Inflammatory Drugs), anti-septic agents, antibiotics, anti-bacteria agents, anti-fungal agents, anti-viral agents, anti-allergenic agents, anti-irritants, insect-repelling agents, phototherapy agents, blood-coagulating agents, antineoplastics, immune system boosting agents, immune system suppressing agents, coal tar, anthralin, fluocinonide, methotrexate, cyclosporine, pimecrolimus, tacrolimus, azathioprine, fluoruracil, ceramides, counterirritants, skin cooling compounds, and a combination thereof.

Suitable beneficial agents include, but are not limited to, anti-oxidants, vitamins, vitamin D3 analogues, retinoids, minerals, mineral oil, petroleum jelly, fatty acids, plant extracts, polypeptides, antibodies, proteins, sugars, humectants, emollients, a combination thereof, and other similar agents beneficial for topical application known in the art.

Another aspect of the present invention is directed to a composition that forms a layer on the skin, wherein the composition has a glass transition temperature about or below body temperature. The term "glass transition temperature" refers to the temperature at a transition from the solid state to the liquid state occurs. A glass transition temperature may be reported as a temperature (° C., ° F. or K). Glass transition temperature can be measured in vitro, for example, using thermal analysis instruments such as a Differential Scanning Calorimeter (DSC) or a Thermogravimetric Analysis (TGA). In certain embodiments, the composition that forms the layer has a glass transition temperature below about 37° C. In preferred embodiments, the composition that forms the layer has a glass transition temperature below about 25° C. In further preferred embodiments, the composition that forms the layer has a glass transition temperature below about 0° C. In certain embodiments, the first part of the composition that forms the layer has a glass transition temperature below about 37° C. In preferred embodiments, the first part of the composition that forms the layer has a glass transition temperature below about 25° C. In further preferred embodiments, the first part of the composition that forms the layer has a glass transition temperature below about 0° C. In certain embodiments, the second part of the composition that forms the layer has a glass transition temperature below about 37° C. In preferred embodiments, the second part of the composition that forms the layer has a glass transition temperature below about 25° C. In further preferred embodiments, the second part of the composition that forms the layer has a glass transition temperature below about 0° C.

One aspect of the invention is directed to compositions that form a layer on a surface such as leather, glass, plastic, metal, ceramic, semiconductor, insulator, conductor, or the skin or the mucous membrane or the lip or the hair or the nail in-situ, i.e., in the location where the compositions disclosed herein are applied. The layer is preferably formed without the need of heating or UV or light or electrical or magnetic or pressure or sound exposure. The layer can be additionally formed with exposure to one or more of heating, UV, light, electricity, magnetism, pressure and sound. Another aspect of the invention is directed to compositions that form a layer on a surface such as leather, glass, plastic, ceramic, semiconductor, insulator, conductor, or metal, which is then applied over the skin or the mucous membrane or the lip or the hair or the nail of a subject.

Another aspect of the present invention is directed to a composition that forms a layer that has low tackiness and forms quickly. The term "set-to-touch time" refers to the time when the layer has solidified sufficiently that it no longer flows and transfers to a finger or an artificial substrate that lightly touches it under normal force less than 50 Newtons. When the layer is "set-to-touch," it becomes substantially resistant to environmental factors, thus allowing the user to resume intended activities. The term "tack-free time" refers to the time when the layer has solidified sufficiently that it no longer sticks to a finger or a substrate that lightly touches it under normal force less than 0.15 Newtons, incurring stickiness to the film. When the layer is "tack-free," it becomes substantially resistant to surface friction and abrasion from environmental factors, thus allowing the user to further resume intended activities. Consequently, an appropriate set-to-touch time and tack-free time for the layer is important: a longer set-to-touch time and tack-free time would require the user to wait a longer time before resuming activities, affecting consumer compliance; while a shorter set-to-touch time and tack-free time would require faster handling, application and/or spreading of the composition, which is not attainable by all users, or may otherwise negatively affect the continuity, evenness, uniformity, and/or physical properties of the layer. We have discovered that increasing the molar ratio of the low viscosity crosslinkable polymer(s), particularly low viscosity alkenyl or alkynyl organopolymer in the composition (further particularly in the second part in case of a two-part composition), reduced set-to-touch time and tack-free time of the layer formed. Thus, it is critical to have an appropriate amount of low viscosity crosslinkable polymer(s), particularly low viscosity alkenyl or alkynyl organopolymer in the composition to achieve a desirable set-to-touch time and tack-free time.

In certain embodiments, the composition further comprises between 0.05% and 30% by weight one or more polymers and/or non-polymers that affects the set-to-touch time of the composition. Such polymers may be, but are not necessarily, any one of the Polymers A, B or C. Other suitable polymers include, but are not limited to, polytetrafluoroethylene (PTFE), poly(methyl methacrylate) (PMMA), polyethylene (PE or polyethene), polypropylene (PP or polypropene), polyvinylidene fluoride (PVDF), polyurethane, acrylate, polyester such as nylons, polyether, polycarbonate, polysulfone, polyphosphate, or a combination thereof. Suitable non-polymers include, but are not limited to, particles such as carbon, silica, boron nitride, metal oxides (e.g., zinc oxide, titanium dioxide) and salts such as carbonate salts (e.g., calcium, magnesium, sodium salts), sulfates, phosphates, borates, halogenated salts, or a combination thereof.

Set-to-touch time can be measured on test subjects, for example, using the Set-to-Touch Time and Tack-Free Time of Film Test described herein, as modified from ASTM D5895-03. Set-to-touch time can also be measured in vitro, for example, using the Set-to-Touch Time Film Test described herein, using suitable substrates, for example, polyurethane, polypropylene and/or Cowhide Tooling leather. In certain embodiments, the composition has a set-to-touch time of greater than about 1 second and less than about 10 minutes. In preferred embodiments, the composition has a set-to-touch time of greater than about 30 seconds and less than about 4 minutes. In further preferred embodiments, the composition has a set-to-touch time of greater than about 30 seconds and less than about 2 minutes. In further preferred embodiments, the composition has a set-to-touch time of greater than about 1 minute and less than about 2 minutes. In other preferred embodiments, the composition has a set-to-touch time of about 2 minutes. Polyurethane and polypropylene have surface conditions preferably used for the measurement of set-to-touch time due to its smoothness, and low aspect ratio and cure characters in-vitro that are similar to the cure characters on skin in-vivo.

Id Tack-free time is measured on test subjects by using the Set-to-Touch Time and Tack-Free Time of Film Test described herein, as modified from ASTM D5895-03. Tack-free time can also be measured in vitro, by using the Set-to-Touch Time and Tack-Free Time of Film Test described herein over suitable substrates, for example, polyurethane, polypropylene, and Cowhide Tooling leather. In certain embodiments, the composition has a tack-free time of greater than about 1 second and less than about 10 minutes. In preferred embodiments, the composition has a tack-free time of greater than about 30 seconds and less than about 4 minutes. In further preferred embodiments, the composition has a tack-free time of greater than about 30 seconds and less than about 2 minutes. In further preferred embodiments, the composition has a tack-free time of greater than about 1 minute and less than about 2 minutes. In other preferred embodiments, the composition has a tack-free time of about 2 minutes. Polyurethane and polypropylene have surface conditions preferably used for the measurement of tack-free time due to their smooth surface with low aspect ratio and cure characters in-vitro that are similar to the cure characters on skin in-vivo.

Another aspect of the invention is directed to a composition that forms a thin layer on the skin. Thickness of the layer affects both its breathability, invisibility, compressibility, and its skin occlusive effects. "Thickness" refers to the average thickness of the layer applied to a surface. Thickness of the layer formed can be measured in vitro, for example, on a cross-section of a layer using microscope having a stage or ocular micrometer. Thickness of the layer is measured on a specimen formed from the composition in vitro by using the ASTM D3767 Rubber-Measurement of Dimensions using the Mitutoyo Thickness Gauge test, modified to be used on free-standing film or on a layer over a substrate such as polyurethane, polypropylene, and Cowhide Tooling leather at room temperature and about 50% relative humidity. Polyurethane and polypropylene have surface conditions that are preferably used for the thickness measurement due to their smooth surface with low aspect ratio, allowing the layer to be easily removed as a free-standing layer. Cowhide Tooling leather has the preferred water absorption and grain surface conditions needed for the thickness measurement. Cowhide Tooling leather is commonly vegetable tanned and absorbs water readily and dries out quickly because the fiber structure is less compact than that of chrome tanned leather. Cowhide Tooling leather is "full grain," meaning the hair has been removed and the original grain remains. Thickness of the layer can also be measured on a specimen formed from the composition in vitro, for example, using the ASTM D-6132 Nondestructive Measurement of Dry Film Thickness of Applied Organic Coatings using the PosiTector Ultrasonic Coating Thickness Gauges test, modified to use polyurethane as substrate at room temperature and about 50% relative humidity.

The thickness measurement of the substrate is made before and after applying the composition, from which the difference in thickness before and after applying the composition indicates the layer thickness. In certain embodiments, the average thickness of the layer is less than about 0.1 mm (100 microns). In preferred embodiments, the average thickness of the layer is about 0.5 to about 100 microns, about 1 to about 90 microns, about 10 to about 80 microns, about 30 to about 70 microns, about 40 to about 60 microns. In further preferred embodiments, the average thickness of the layer is about 50 microns.

Another aspect of the invention is directed to a composition that forms a durable layer on the skin. The durability of the layer on the skin can be determined, for example, using the Film Durability on Skin test described herein. We have discovered that increasing the molar ratio and/or viscosity/molecular weight of the high viscosity crosslinkable polymer, particularly high viscosity alkenyl or alkynyl organopolymer in the composition (further particularly in the first part in case of a two-part composition), enhances durability, including both physical integrity and adhesion, of the layer formed. We have discovered that there exists a range of the relative molar ratio between the unsaturated carbon groups in the alkenyl or alkynyl organopolymer(s) and the hydride groups in the organopolymer(s) in the composition (further particularly in the first part in case of a two-part composition), that further enhances durability, including both physical integrity and adhesion, of the layer formed. We have further discovered that while pre-forming the layer provides a cohesive layer with good adhesion to the substrate, in-situ formation of the layer promotes better adhesion to the surface, providing further enhanced layer durability. Gradients in cross-linking density created by catalyst migration in a two-part composition may further enhance adhesion to the substrate and, consequently, further enhanced layer durability. The balance of different viscosities and different types of crosslinkable polymers in the compositions affects the balance between set-to-touch time, tack-free time, and durability of the layer formed.

In certain embodiments, the layer remains substantially intact on the skin for about 24 hours or more with common, routine daily activities and/or with demanding activities. In preferred embodiments, the layer remains substantially intact on the skin for at least about 30 hours, about 36 hours, about 48 hours, about 60 hours, about 72 hours, about 84 hours, or about 96 hours with common, routine daily activities and/or with demanding activities. In other preferred embodiments, the layer remains substantially intact on the skin for at least about 120 hours, about 144 hours, or about 168 hours with common, routine daily activities and/or with demanding activities. "Remain substantially intact" means that the layer remains on at least about 50%, at least about 60%, at least about 70%, at least about 80%, at least about 90%, at least about 95% of the area of the skin to which it was originally applied, or at least about 50%, at least about 60%, at least about 70%, at least about 80%, at least about 90%, at least about 95% by weight remains on the skin.

In certain embodiments, the layer remains at least about 50% intact, at least about 60% intact, at least about 70% intact by either area or by weight on the skin for about 24 hours or more with common, routine daily activities and/or with demanding activities. In preferred embodiments, the layer remains at least about 80% intact by either area or by weight on the skin for about 24 hours or more with common, routine daily activities and/or with demanding activities. In other preferred embodiments, the layer remains at least about 90% intact, or at least about 95% intact by either area or by weight on the skin for about 24 hours or more with common, routine daily activities and/or with demanding activities. In certain embodiments, the layer remains at least about 50% intact, at least about 60% intact, at least about 70% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities. In preferred embodiments, the layer remains at least about 80% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities. In other preferred embodiments, the layer remains at least about 90% intact, or at least about 95% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities.

Another aspect of the invention is directed to a composition that forms a layer on the skin that resists peeling. Resistance to peeling is determined by measuring adhesive force using the Peel Adhesion test described herein. The term "adhesive force" refers to the force per unit length required to separate the materials adhered to a standard substrate such as leather or polypropylene or polyurethane. In certain embodiments, the adhesive force of the layer on polypropylene substrate is greater than about 2 N/m. In preferred embodiment, the adhesive force of the layer on polypropylene substrate is greater than about is greater than about 5 N/m. In further preferred embodiments, the adhesive force of the layer on polypropylene substrate is greater than about 20 N/m, 40 N/m, 60 N/m, 80 N/m, greater than about 100 N/m, or greater than about 200 N/m.

Another aspect of the invention is directed to a composition that forms a layer that is resistant to environmental factors, such as exposure to heat, cold, wind, water, humidity, bodily fluids (e.g., blood, pus/liquor puris, urine, saliva, sputum, tears, semen, milk, or vaginal secretion), sebum, saline, seawater, soapy water, detergent water, or chlorinated water. Such resistance to environmental factors is represented by the minimal weight increase upon exposures to these environmental factors. The weight change of the layer is determined by using the ASTM D2765-95 Determination of Gel Content and Swell Ratio of Crosslinked Ethylene Plastics test using a weight scale. In certain embodiments, the weight of the layer increases by less than about 10% upon exposure to such environmental factors at about 1-hour time point (i.e., 1 hour after application of the composition disclosed herein), about 4-hour, about 6-hour, about 12-hour, about 24-hour, about 30-hour, about 36-hour, about 48-hour, or between 48 hours and one week time point. In preferred embodiments, the weight of the layer increases by less than about 5%, or less than about 1% upon exposure to such environmental factors at about 1-hour, about 4-hour, about 6-hour, about 12-hour, about 24-hour, about 30-hour, about 36-hour, about 48-hour, or between 48 hours and one week time point. In further preferred embodiments, the weight of the layer increases by less than about 0.5% upon exposure to such environmental factors at about 1-hour, about 4-hour, about 6-hour, about 12-hour, about 24-hour, about 30-hour, about 36-hour, about 48-hour, or between 48 hours and one week time point.

In certain embodiments, the weight of the layer increases by less than about 50% upon exposure to such environmental factors at about 1-hour time point (i.e., 1 hour after application of the composition disclosed herein), about 4-hour, about 6-hour, about 12-hour, about 24-hour, about 30-hour, about 36-hour, about 48-hour, or between 48-hour and one-week time point. In preferred embodiments, the weight of the layer increases by less than about 5%, or less than about 1% upon exposure to such environmental factors at about 1-hour, about 4-hour, about 6-hour, about 12-hour, about 24-hour, about 30-hour, about 36-hour, about 48-hour, or between 48-hour and one-week time point. In further preferred embodiments, the weight of the layer increases by less than about 0.5% upon exposure to such environmental factors at about 1-hour, about 4-hour, about 6-hour, about 12-hour, about 24-hour, about 30-hour, about 36-hour, about 48-hour, or between 48-hour and one-week time point.

Another aspect of the invention is directed to a composition that forms a layer that is flexible, stretchable, elastic and body-movement conforming. Such flexible, stretchable, elastic and body-movement conforming properties of the layer are represented by the tensile modulus, shear modulus, cyclic tensile residual strain, cyclic tensile hysteresis loss energy, fracture strain, fracture stress, and fracture toughness measurements, which can be tested in vitro on a specimen formed from the composition using the methods described herein. For a layer to have the appearance and durability of normal, healthy skin, these physical properties of the layer preferably fall within specific ranges so that the layer will not break when being deformed by body movements and will return to essentially the same state when the body returns to the original state.

The terms "tensile strength," or "ultimate tensile strength," or "fracture stress," or "stress at break," or "maximum tensile stress," or "ultimate tensile stress," or "fracture strength," or "breaking strength" refer to stress at which a specimen fails via fracture. Tensile strength can be measured on a specimen formed from the composition in vitro, for example, using the Cyclic and Extension Pull Test as described herein. In certain embodiments, the tensile strength of the layer is greater than about 0.05 MPa, or greater than 0.10 MPa, or greater than 0.20 MPa, or greater than about 0.5 MPa. In preferred embodiments, the tensile strength of the layer is greater than about 1.0 MPa, or greater than about 2.0 MPa. In preferred embodiments, the tensile strength of the layer is less than about 5 MPa. In further preferred embodiments, the tensile strength of the layer is about 3.0 MPa.

The terms "fracture strain," or "elongation at break," or "stretchiness at break," or "strain at break," or "maximum elongation," or "maximum strain," or "maximum stretchiness" or "extension at break" or "maximum extension" refer to strain at which a specimen fails via fracture. Fracture strain can be measured on a specimen formed from the composition in vitro, for example, using the Cyclic and Extension Pull Test as described herein. In certain embodiments, the fracture strain of the layer is greater than about 25%, greater than 50%, greater than about 100%, greater than about 200%, or greater than about 400%. In further preferred embodiments, the fracture strain of the layer is greater than about 600%, greater than about 800%, greater than about 1000%, greater than about 1200, or greater than about 1500%.

The terms "tensile modulus," or "Young's modulus," or "modulus of elasticity," or "stiffness," or "tensile stiffness," or "elastic modulus" refer to the force per unit area that is needed to stretch and deform a material beyond the initial length. Tensile modulus is an inverse of compliance, relating to flexibility or deformability of a material beyond the initial length. Tensile modulus can be measured on a specimen formed from the composition in vitro, for example, using the Cyclic and Extension Pull Test as described herein. Tensile modulus can also be measured using the ASTM D5083 Tensile Properties of Reinforced Thermosetting Plastics Using Straight-Sided Specimens standard test. In certain embodiments, the tensile modulus of the layer is about 0.01 to about 40 MPa. In preferred embodiments, the tensile modulus of the layer is about 0.05 to about 20 MPa, or about 0.1 to about 10 MPa, about 0.1 to about 5 MPa, about 0.1 to about 11 MPa. In further preferred embodiments, the tensile modulus of the layer is about 0.25 to about 0.75 MPa. In further preferred embodiments, the tensile modulus of the layer is about 0.5 MPa.

The terms "shear modulus" or "modulus of rigidity" or "shear stiffness" refer to the force per unit area that is needed to shear and deform a material beyond the initial length. Shear modulus is be measured on a specimen formed from the composition in vitro by using the ASTM D7175 Determining the Rheological Properties of Asphalt Binder using a Dynamic Shear Rheometer. In certain embodiments, the shear modulus of the layer is about 0.005 to about 10 MPa. In preferred embodiments, the shear modulus of the layer is about 0.05 to about 5 MPa, or about 0.1 to about 11 MPa. In further preferred embodiments, the shear modulus of the layer is about 0.25 to about 0.75 MPa. In further preferred embodiments, the shear modulus of the layer is about 0.5 MPa.

The term "cyclic tensile residual strain" refers to tensile residual strain after cyclic tensile deformation. The term "residual strain" refers to strain that remains in a material after the original cause of stress has been removed. Residual strain may be reported as plastic strain, inelastic strain, non-elastic strain, or viscoelastic strain. The cyclic tensile residual strain can be measured on a specimen formed from the composition in vitro, for example, using the Cyclic and Extension Pull Test as described herein. In certain embodiments, the cyclic tensile residual strain of the layer is less than about 10%. In preferred embodiments, the cyclic tensile residual strain of the layer is less than about 5% or less than about 2.5%. In further preferred embodiments, the cyclic tensile residual strain of the layer is less than about 1%. In other preferred embodiments, the cyclic tensile residual strain of the layer is less than about 0.5%, less than about 0.25%, or less than about 0.1%.

The terms "cyclic tensile hysteresis loss energy" or "cyclic hysteresis strain energy" refer to the excess energy being dissipated as heat when the specimen is subjected to cyclic tensile deformation. Cyclic tensile hysteresis loss energy can be measured on a specimen formed from the composition in vitro, for example, using the Cyclic and Extension Pull Test as described herein. In certain embodiments, the cyclic tensile hysteresis loss energy of the layer is less than about 1 $kJ/m^3$. In preferred embodiments, the cyclic tensile hysteresis loss energy of the layer is less than about 0.5 $kJ/m^3$. In further preferred embodiments, the cyclic tensile hysteresis loss energy of the layer is less than about 0.2 $kJ/m^3$.

The terms "fracture toughness," or "toughness," or "tensile toughness," or "deformation energy," or "failure energy," or "fracture energy" refer to the ability to absorb energy of mechanical deformation per unit volume up to the point of failure. Fracture toughness can be measured on a specimen formed from the composition in vitro, for example, using the Cyclic and Extension Pull Test as described herein. In certain embodiments, the fracture toughness of the layer is greater than about 500 $kJ/m^3$. In preferred embodiments, the fracture toughness of the layer is greater than about 5,000 $kJ/m^3$. In further preferred embodiments, the fracture toughness of the layer is greater than about 10,000 $kJ/m^3$, or greater than about 50,000 $kJ/m^3$.

Another aspect of the invention is directed to a composition that forms a layer that is permeable to oxygen and water vapor, as represented by the oxygen permeability coefficient, water vapor permeability coefficient, oxygen transmission rate, water vapor transmission rate, oxygen permeance and/or water vapor permeance, which are tested in vitro using the methods described herein.

The term "oxygen transmission rate" or OTR refers to the permeation flux of oxygen through a membrane with certain thickness. Oxygen transmission rate can be measured on a specimen formed from the composition in vitro, for example, using the ASTM F2622 Oxygen Gas Transmission Rate Through Plastic Film and Sheeting Using Various Sensors test. In certain embodiments, the oxygen transmission rate of the layer is greater than about $5\times10^{-9}$ $cm^3/(cm^2 \cdot s)$. In preferred embodiments, the oxygen transmission rate of the layer is greater than about $5\times10^{-7}$ $cm^3/(cm^2 \cdot s)$. In further preferred embodiments, the oxygen transmission rate of the layer is greater than about $5\times10^{-5}$ $cm^3/(cm^2 \cdot s)$. In other preferred embodiments, the oxygen transmission rate of the layer is greater than about $5\times10^{-4}$ $cm^3/(cm^2 \cdot s)$, greater than about $5\times10^{-3}$ $cm^3/(cm^2 \cdot s)$, greater than about $5\times10^{-2}$ $cm^3/(cm^2 \cdot s)$, greater than about 0.5 $cm^3/(cm^2 \cdot s)$. In preferred embodiments, the oxygen transmission rate of the layer is less than about 5 $cm^3/(cm^2 \cdot s)$.

The term "oxygen permeance" refers to the permeation flux of oxygen through a membrane with certain thickness, per unit oxygen vapor pressure difference between the membrane (typically in cmHg). Oxygen permeance can be measured on a specimen formed from the composition in vitro, for example, using the ASTM F2622 Oxygen Gas Transmission Rate Through Plastic Film and Sheeting Using Various Sensors test. In certain embodiments, the oxygen permeance of the layer is greater than about $5\times10^{-11}$ $cm^3/(cm^2 \cdot s \cdot cm\ Hg)$. In preferred embodiments, the oxygen permeance of the layer is greater than about $5\times10^{-9}$ $cm^3/(cm^2 \cdot s \cdot cm\ Hg)$, or greater than about $5\times10^{-7}$ $cm^3/(cm^2 \cdot s \cdot cm\ Hg)$. In further preferred embodiments, the oxygen permeance of the layer is greater than about $5\times10^{-6}$ $cm^3/(cm^2 \cdot s \cdot cm\ Hg)$. In other preferred embodiments, the oxygen permeance of the layer is greater than about $5\times10^{-5}$ $cm^3/(cm^2 \cdot s \cdot cm\ Hg)$, greater than about $5\times10^{-4}$ $cm^3/(cm^2 \cdot s \cdot cm\ Hg)$, greater than about $5\times10^{-3}$ $cm^3/(cm^2 \cdot s \cdot cm\ Hg)$, or greater than about $5\times10^{-2}$ $cm^3/(cm^2 \cdot s \cdot cm\ Hg)$. In preferred embodiments, the oxygen permeance of the layer is less than about 0.5 $cm^3/(cm^2 \cdot s \cdot cm\ Hg)$.

The terms "oxygen permeability coefficient" or "intrinsic oxygen permeability" refer to a measure of how fast the oxygen can move through a membrane, which involves a successive process of oxygen sorption into a membrane then followed by oxygen diffusion through the membrane. Oxygen permeability coefficient can be measured on a specimen formed from the composition in vitro, for example, using the ASTM F2622 Oxygen Gas Transmission Rate Through Plastic Film and Sheeting Using Various Sensors test. In certain embodiments, the oxygen permeability coefficient of the layer is greater than about $5\times10^{-4}$ Barrer. In preferred embodiments, the oxygen permeability coefficient of the layer is greater than about $5\times10^{-2}$ Barrer, greater than about 5 Barrer, or greater than about 50 Barrer. In further preferred embodiments, the oxygen permeability coefficient of the layer is greater than about 500 Barrer. In other preferred embodiments, the oxygen permeability coefficient of the layer is greater than about 5,000 Barrer. In preferred embodiments, the oxygen permeability coefficient of the layer is less than about 20,000 Barrer.

The term "water vapor transmission rate" or WVTR refers to the permeation flux of water vapor through a membrane with certain thickness. Water vapor transmission rate can be measured on a specimen formed from the composition in vitro, for example, using the ASTM F1249 Water Vapor Transmission Rate Through Plastic Film and Sheeting Using a Modulated Infrared Sensor test. In certain embodiments, the water vapor transmission rate of the layer is greater than about $1\times10^{-9}$ $cm^3/(cm^2 \cdot s)$ and less than about $1.5\times10^{-1}$ $cm^3/(cm^2 \cdot s)$. In preferred embodiments, the water vapor transmission rate of the layer is greater than about $1\times10^{-8}$ $cm^3/(cm^2 \cdot s)$. In further preferred embodiments, the water vapor transmission rate of the layer is greater than about $1\times10^{-7}$ $cm^3/(cm^2 \cdot s)$. In other preferred embodiments, the water vapor transmission rate of the layer is greater than about $1\times10^{-6}$ $cm^3/(cm^2 \cdot s)$, greater than about $1\times10^{-5}$ $cm^3/(cm^2 \cdot s)$, or greater than about $1\times10^{-4}$ $cm^3/(cm^2 \cdot s)$. In preferred embodiments, the water vapor transmission rate of the layer is less than about $1.5 \times 10^{-2}$ cm$^3$/(cm$^2$·s).

The term "water vapor permeance" refers to the permeation flux of water vapor through a barrier with certain thickness, per unit water vapor pressure difference between one side and the other side of the barrier (typically in cmHg). Water vapor permeance can be measured on a specimen formed from the composition in vitro, for example, using the ASTM F1249 Water Vapor Transmission Rate Through Plastic Film and Sheeting Using a Modulated Infrared Sensor test. In certain embodiments, the water vapor permeance of the layer is greater than about $1 \times 10^{-11}$ cm$^3$/(cm$^2$·s·cm Hg) and less than about $2 \times 10^{-3}$ cm$^3$/(cm$^2$·s·cm Hg). In preferred embodiments, the water vapor permeance of the layer is greater than about $1 \times 10^{-10}$ cm$^3$/(cm$^2$·s·cm Hg), or greater than about $1 \times 10^{-9}$ cm$^3$/(cm$^2$·s·cm Hg). In further preferred embodiments, the water vapor permeance of the layer is greater than about $1 \times 10^{-8}$ cm$^3$/(cm$^2$·s·cm Hg). In other preferred embodiments, the water vapor permeance of the layer is greater than $1 \times 10^{-7}$ cm$^3$/(cm$^2$·s·cm Hg), or greater than $1 \times 10^{-6}$ cm$^3$/(cm$^2$·s·cm Hg). In preferred embodiments, the water vapor permeance of the layer is less than about $2 \times 10^{-2}$ cm$^3$/(cm$^2$·s·cm Hg).

The terms "water vapor permeability coefficient" or "intrinsic water vapor permeability" refer to a measure of how fast water vapor can move through a barrier, which involves a successive process of water vapor sorption into a barrier, followed by water vapor diffusion through the barrier. Water vapor permeability coefficient can be measured on a specimen formed from the composition in vitro, for example, using the ASTM F1249 Water Vapor Transmission Rate Through Plastic Film and Sheeting Using a Modulated Infrared Sensor test. In certain embodiments, the water vapor permeability coefficient of the layer is greater than about $1 \times 10^{-3}$ Barrer and less than about $1 \times 10^{6}$ Barrer. In preferred embodiments, the water vapor permeability coefficient of the layer is greater than about 0.01 Barrer, greater than about 0.1 Barrer, greater than about 1 Barrer, greater than about 10 Barrer, greater than about 100 Barrer, or greater than about $1 \times 10^{3}$ Barrer. In further preferred embodiments, the water vapor permeability coefficient of the layer is greater than about $1 \times 10^{4}$ Barrer and less than about $1 \times 10^{5}$ Barrer.

Another aspect of the invention is directed to a composition that forms a layer over skin such that the transepidermal water loss of the area treated with the composition is reduced or comparable to untreated skin. The term "transepidermal water loss" refers to the measurement of the quantity of water that passes from inside a body through the epidermal layer to the surrounding atmosphere via diffusion and evaporation processes. Transepidermal water loss is measured by using the Transepidermal Water Loss (TEWL) Measurement Test as described herein. Differences in TEWL measurements caused by age, race, gender, and/or area of the skin of the subject tested are generally less than the standard error in the TEWL measurements. TEWL measurements can be made at any time on or after about 30 minutes time point, for example, at about 1-hour, about 4-hour, about 6-hour, about 12-hour, about 24-hour, about 30-hour, about 36-hour, about 48-hour, or between 48 hours and one week time point. In certain embodiments, the transepidermal water loss after application of the composition is less than about 40 g/(m$^2$·hr). In preferred embodiments, the transepidermal water loss after application of the composition is less than about 20 g/(m$^2$·hr). In further preferred embodiments, the transepidermal water loss after application of the composition is less than about 10 g/(m$^2$·hr). In other preferred embodiments, the transepidermal water loss after application of the composition is less than about 5 g/(m$^2$·hr), or less than about 1 g/(m$^2$·hr).

Another aspect of the invention is directed to a composition that forms a layer over skin such that the skin hydration of the area treated with the composition is improved or comparable to untreated skin. The term "skin hydration" refers to the measure of water content of the skin, typically through a Corneometer which is based on capacitance measurement of a dielectric medium near skin surface. Skin hydration measurements can be made at any time on or after about 30-minute time point, such as at about 1-hour, about 4-hour, about 6-hour, about 12-hour, about 24-hour, about 30-hour, about 36-hour, about 48-hour, or between 48 hours and one week time point. Skin hydration can be measured, for example, using a Corneometer pursuant to the procedure as described in H. Dobrev, "Use of Cutometer to assess epidermal hydration," *Skin Research and Technology* 2000, 6(4):239-244. In certain embodiments, the skin hydration after application of the composition is greater than about 20 arbitrary units (normalized hydration value) of Corneometer. In preferred embodiments, the skin hydration after application of the composition is greater than about 40 arbitrary units of Corneometer. In other preferred embodiments, the skin hydration after application of the composition is greater than about 60 arbitrary units of Corneometer, or greater than about 80 arbitrary units of Corneometer.

Skin hydration can also be measured, for example, using the procedure as described in Clarys et al., Hydration measurements of the stratum corneum: comparison between the capacitance method (digital version of the Corneometer CM 825®) and the impedance method (Skicon-200EX®), *Skin Research and Technology* 2011, 18(3):316-23. In certain embodiments, the skin hydration after application of the composition is greater than about 20 microSiemens. In preferred embodiments, the skin hydration after application of the composition is greater than about 50 microSiemens. In other preferred embodiments, the skin hydration after application of the composition is greater than about 100 microSiemens, or greater than about 200 microSiemens, or about 400 microSiemens.

Another aspect of the invention is directed to a composition that forms a layer on the skin that tightens the skin. The tightening effect which is caused by increasing the skin tension is quantified from a specimen formed from the composition in vitro by using the with the in-vitro curl test as described herein. In certain embodiments, the tension is increased by greater than 0.1 N/m. In preferred embodiments, the tension is increased by greater than 0.2 N/m. In preferred embodiments, the tension is increased by greater than 0.5 N/m, by greater than 1.0 N/m, by greater than 2.0 N/m, by greater than 5.0 N/m, by greater than 10 N/m, by greater than 20 N/m, by greater than 50 N/m, by greater than 100 N/m, by greater than 500 N/m, or by greater than 1,000 N/m.

Another aspect of the invention is directed to a composition that forms a layer on the skin such that the surface contour of the skin can be modulated. The "surface contour of the skin" is observed with Canfield 3-D Imaging System or visually with the comparative photos before and after the application of the test composition.

In preferred embodiments, the composition forms a layer that is cosmetically elegant and has the appearance of normal, healthy, and youthful skin of the subject to which the composition or layer is applied. Consequently, the layer may convey cosmetic and therapeutic benefits that reduce the appearance of any signs of ageing which include under eye bags, laugh lines, crow feets, forehead lines and wrinkles.

Another aspect of the invention is directed to a composition that forms a layer on the skin such that retraction time of the area treated with the composition is decreased comparing with untreated skin. The term "retraction time" refers to the time taken for the skin to return to its original state after initial deformation by the Suction Cup device. Skin retraction time can be measured, for example, using a cutometer/suction cup pursuant to the procedure as described in H. Dobrev, "Use of Cutometer to assess epidermal hydration," *Skin Research and Technology* 2000, 6(4):239-244. Skin retraction time measurements can be made at any time on or after about 30 minutes time point, such as at about 1-hour, about 4-hour, about 6-hour, about 12-hour, about 24-hour, about 30-hour, about 36-hour, about 48-hour, or between 48 hours and one week time point. In certain embodiments, the skin retraction time after application of the composition is decreased by about 5% to about 75%. In preferred embodiments, the skin retraction time after application of the composition is decreased by greater than about 10%. In other preferred embodiments, the skin retraction time after application of the composition is decreased by greater than about 25%, or greater than about 50%.

Another aspect of the invention is directed to a composition that forms a layer that is cosmetically elegant and has the appearance of normal, healthy skin of the subject to which the composition or layer is applied. Consequently, the layer may convey cosmetic and therapeutic benefits by masking, concealing, covering, or reducing the appearance of skin conditions, e.g., conditions of compromised skin barrier function, symptoms of skin conditions, e.g., conditions of compromised skin barrier function, and/or skin imperfections such as hyperpigmentation, melisma, and vitiligo.

Another aspect of the invention is directed to a composition that forms a layer that is cosmetically elegant and has the novel appearance of the skin of the subject to which the composition or layer is applied. Consequently, the layer may convey cosmetic and therapeutic benefits by enhancing the appearance of skin which includes tattoo and make-up.

In preferred embodiments, the composition further comprises one or more optics modifiers. In other preferred embodiments, the first part and/or the second part further independently comprise one or more optics modifiers or particles. Optics modifiers or particles introduce surfaces responsive to optical or photonic interaction, e.g., roughness for light scattering, thereby imparting desirable shine, glossy, glow, matte appearance beyond or comparable to that of normal, healthy skin, preferably avoiding a significantly more shiny and/or glossy appearance than normal skin. Suitable optics modifiers or particles include, for example, pigments, dyes, polymers such as nylon (e.g., nylon-6, nylon-10, nylon-12), silicone, acrylic, acrylates/carbamate or other polymer or copolymer beads or particles, polyethylene beads, polymethymethacrylate beads, polystyrene beads, polyurethane beads; inorganics such as silica (e.g., silica and DMPA/isophthalic acid/SMDI copolymer, available as ChronoSphere® Opticals from Lonza Group), boron nitride, talc, mica, alumina, titania; metal such as silver nanoparticles; and silicone, acrylic, acrylates/carbamate or other polymer or copolymer beads or particles. In certain embodiments, the optics modifiers or particles have an average particle diameter of between about 1 µm and about 20 µm. In a preferred embodiment, the optics modifiers or particles have an average particle diameter of between about 0.1 µm and about 20 µm. In preferred embodiments, the optics modifiers or particles have an average particle diameter of 2 µm to 15 µm, and further preferably 5 to 10 µm.

Another aspect of the invention is directed to a composition that forms a layer that does not significantly change the shine and/or gloss of the area over which the composition is applied. Shine and/or gloss can be measured on a specimen formed from the composition in vitro, for example, using a Glossmeter pursuant to the ASTM D523 Specular Gloss test, at 20°, 60°, and/or 85° measurement angels. The light and measurement angel can be selected based on the anticipated gloss range. For example, if the measurement made at 60° is greater than about 70 gloss units (GU), the measurement angle should be changed to 20° to optimize measurement accuracy. Conversely, if the measurement made at 60° is less than about 10 GU, the measurement angle should be changed to 85° to optimize measurement accuracy. 45° or 75° measurement angle may also be used depending on the gloss of the substrate used for the test. Various materials can be used as substrate to mimic normal, healthy skin for the test, for example, Cowhide Tooling leather in natural color. Shine and/or gloss change is indicated by the percentage increase or decrease of gloss units in a measurement area after the treatment comparing to before treatment. In certain embodiments, the shine and/or gloss change of the area treated with the composition is less than about 20%. In preferred embodiments, the shine and/or gloss change of the area treated with the composition is less than about 10%. In further preferred embodiments, the shine and/or gloss change of the area treated with the composition is less than about 5%.

Another aspect of the invention is directed to a composition that forms a layer that is clear, transparent, and/or optically invisible. Another aspect of the invention is directed to a composition that forms a layer so that the area with the composition applied has minimal color change before and after the application, such as color L* scale change, color a* scale change, and/or color b* scale change. Color L* scale, color a* scale and color b* scale are the three L*a*b* color space specified by the International Commission on Illumination. Color L* scale, color a* scale and color b* scale changes can be measured on a specimen formed from the composition in vitro, for example, using a Minolta Color Meter pursuant to the ASTM E313 Calculating Yellowness and Whiteness Indices from Instrumentally Measured Color Coordinates. Various materials can be used as substrate to mimic normal, healthy skin for the test, for example, Cowhide Tooling leather in natural color.

In certain embodiments, the color L* scale change of the area treated with the composition is less than about 2. In preferred embodiments, the color L* scale change of the area treated with the composition is less than about 1.5. In other preferred embodiments, the color L* scale change of the area treated with the composition is less than about 1, or less than about 0.5. In certain embodiments, the color a* scale change of the area treated with the composition is less than about 2. In preferred embodiments, the color a* scale change of the area treated with the composition is less than about 1.5. In other preferred embodiments, the color a* scale change of the area treated with the composition is less than about 1, or less than about 0.5. In certain embodiments, the color b* scale change of the area treated with the composition is less than about 2. In preferred embodiments, the color b* scale change of the area treated with the composition is less than about 1.5. In other preferred embodiments, the color b* scale change of the area treated with the composition is less than about 1, or less than about 0.5.

Another aspect of the invention is directed to a composition that forms a layer that is translucent or opaque. In certain embodiments, the composition further comprises one or more colorants, including, but not limited to, pigments, dyes (including fluorescent dyes), FD&C colors, D&C colors, lake colors, other color-imparting compounds, and a combination thereof. Other suitable colorants are disclosed, for example, in the CTFA Cosmetic Ingredient Handbook, 2nd ed. 1992. In preferred embodiments, the color of the layer substantially matches the color of normal, healthy skin of the subject. In other preferred embodiments, the layer further comprises various colorants, pearlescents, patterns, designs, or a combination thereof, thus conveying make up, cosmetic, aesthetic, and/or decorative benefits.

In certain embodiments, a finishing formulation may be applied with or over the layer during or after its formation to provide a desired tactile sensation or aesthetic look. For example, the finishing formulation may provide a silky, soft and/or smooth tactile sensation or a dewy, fresh, matte, shiny or luminescent aesthetic look. In certain embodiments, the finishing formulation comprises one or more of oils, esters or ethers, feel modifiers, tack modifiers, spreadability enhancers, adhesion modifiers, emulsifiers, emollients, surfactants, thickeners, film formers, humectants, preservatives, cosmetic agents, and/or therapeutic agents.

In certain embodiments, the finishing formulation comprises optics modifiers or particles, colorants, pearlescents, patterns, and/or designs.

In certain embodiments, the finishing formulation may be in various forms, for example, liquid, lotion, cream, ointment, serum, gel, spray, foam, mousse, spritz, powder, or other suitable forms.

Another aspect of the invention is directed to a kit for use in modifying skin condition of a subject; in treatment of conditions of compromised skin barrier function. In certain embodiments, the kit comprises (i) a composition disclosed herein, and (ii) instructions for use.

In certain embodiments, the kit comprises (i) a first part disclosed herein, (ii) a second part disclosed herein, and (iii) instructions for use. In preferred embodiments, the first part and the second part are prevented from coming into contact prior to use. In preferred embodiments, the first part and the second part are packaged in separate containers or compartments, and applied one at a time or mixed together prior to or upon use.

In certain embodiments, the kit further comprises a finishing formulation. In certain embodiments, the kit further comprises a cleanser suitable for removing the layer from the skin, e.g., the cleansers disclosed in U.S. Pat. No. 8,691,202. In certain embodiments, the kit further comprises one or more brush(es), swab(s), and/or mirror(s).

Another aspect of the invention is directed to a device formed by application of any of the compositions disclosed herein. Another aspect of the invention is a prosthetic device, for example, a prosthetic skin, that modulates moisture retention, oxygen permeability and water vapor permeability on the skin formed by application of any of the composition disclosed herein. Another aspect of the invention is a prosthetic device, for example, a prosthetic skin, that modulates optical appearance on the skin formed by application of any of the composition disclosed herein. Another aspect of the invention is a prosthetic device, for example, a prosthetic skin, that modulates mechanical responses of the skin formed by application of any of the composition disclosed herein. Another aspect of the invention is a prosthetic device, for example, a prosthetic skin, that modulates electrical responses of the skin (for example by incorporating graphene or magnetic particles, preferably in Part 1) formed by application of any of the composition disclosed herein. Another aspect of the invention is a prosthetic device, for example, a prosthetic skin, that modulates magnetic responses of the skin formed by application of any of the composition disclosed herein. Another aspect of the invention is a prosthetic device, for example, a prosthetic skin, that modulates pressure responses of the skin formed by application of any of the composition disclosed herein. Another aspect of the invention is a prosthetic device, for example, a prosthetic skin, that modulates pH responses of the skin formed by application of any of the composition disclosed herein. Another aspect of the invention is a prosthetic device, for example, a prosthetic skin, that modulates temperature responses of the skin formed by application of any of the composition disclosed herein. Another aspect of the invention is a prosthetic device, for example, a prosthetic skin, that modulates heat responses of the skin formed by application of any of the composition disclosed herein. Another aspect of the invention is a prosthetic device, for example, a prosthetic skin, that modulates sound responses of the skin formed by application of any of the composition disclosed herein.

Another aspect of the invention is directed to a method for modifying skin functions, by including delivering agents (therapeutics and cosmetics). Non-limiting examples of skin functions that may be modified are skin barrier function; skin pigmentation; skin appearance, including but not limited to wards, acne (sebacic gland), melasma, ventiligo, psoriasis; contact dermatitis or other dermatitis such as stasis dermatitis; and pruritus. Non-limiting examples of therapeutics that may be included are anti-inflammatories, anticoagulants, antibiotics and antiseptics. Therapeutics and cosmetics are administered to a subject in need thereof, by applying to the subject's skin or body a composition as described herein.

Another aspect of the invention is directed to a method for treating conditions of compromised skin barrier function, including dermatological disorders, skin conditions, and wounds, in a subject in need thereof, by applying to the subject's skin or body a composition as described herein.

Another aspect of the invention is directed to a method for treating symptoms of conditions of compromised skin barrier function in a subject in need thereof, comprising applying to the subject's skin or body a composition as described herein, thereby treating one or more symptoms of a condition of compromised skin barrier function.

Another aspect of the invention is directed to a method for occluding skin of a subject in need thereof, comprising applying to the subject's skin or body a composition as described herein, thereby occluding the skin. "Occluding skin" means forming a barrier semi-permeable or impermeable to water vapor directly or indirectly over skin. In certain embodiments, the layer is semi-occlusive in that the composition forms a layer that is semi-permeable to water vapor. Alternatively, the layer is fully-occlusive in that the composition forms a layer that is impermeable to water vapor.

In another aspect of the invention, the occlusion enhances the efficacy of a topical drug also administered to the patient's skin. In one embodiment, the topical drug is a corticosteroid and the disease for the treatment of which the corticosteroid is administered is eczema. In one embodiment, occlusion restores the skin's barrier function. In one embodiment, occlusion enhanced drug delivery.

Occlusive Therapy with semi-occlusive or fully-occlusive layer has been well-established, particularly for atopic dermatitis treatment (for detailed reference: Misha M. Heller, Eric S. Lee, Faranak Kamangar, Wilson Liao and John Y. M Koo (2012). Occlusive Therapy in Atopic Dermatitis, Atopic Dermatitis—Disease Etiology and Clinical Management, Dr. Jorge Esparza-Gordillo (Ed.), ISBN: 978-953-51-0110-9).

We have discovered that our layer can impart the benefit of occlusion to modify and/or restore the barrier function of skin.

Another aspect of the invention is directed to a method for treating a subject for a condition of compromised skin barrier function, or to treat a symptom of such a condition, comprising applying to the subject's skin or body a composition as described herein.

Another aspect of the invention is directed to a method for delivering an agent to a subject to treat a condition of compromised skin barrier function, or to treat a symptom of such a condition, comprising applying to the subject's skin or body a composition as described herein, thereby delivering the agent to the subject.

In one aspect, the present invention imparts its benefit by controlling the rate of delivery of therapeutic agents into the skin, or by modifying and/or enhancing the efficacy of therapy with respect to the administered dosage of therapeutic agents over time.

Another aspect of the invention is directed to a method for delivering to a subject a therapeutic agent to treat a condition of compromised skin barrier function, or to treat a symptom of such a condition, comprising applying to the subject's skin or body a composition as described herein.

In another aspect, the invention imparts its benefit by occlusion and enhancing (trans)dermal drug delivery, with or without the presence of permeation enhancers in the composition described herein. The benefit of occlusion in enhancing (trans)dermal drug delivery modifies and/or enhances the efficacy of drugs with respect to potency and corresponding side-effects.

Another aspect of the invention is directed to a method to mask, conceal, or cover conditions of compromised skin barrier function, symptoms of compromised skin barrier function, and/or skin imperfections, comprising applying to the subject's skin or body a composition as described herein, thereby masking, concealing, or covering the area with the conditions of compromised skin barrier function, symptoms of compromised skin barrier function, and/or skin imperfections.

Another aspect of the invention is directed to a method for treating conditions of compromised skin barrier function, symptoms of compromised skin barrier function, and/or skin imperfections in conjunction with other treatment agent(s) (topical medication, cosmetics and/or personal care products, in the form of ointment, cream, lotion, gel, spray, foam, mousse, or other suitable forms), wherein said other treatment agent(s) is applied to the skin are first, then the composition disclosed herein is applied over such other treatment agent(s) to provide a durable barrier for the other treatment agent(s).

In certain embodiments, the condition of compromised skin barrier function is a dermatological disorder selected from eczema, psoriasis, ichthyosis, rosacea, chronic dry skin, cutaneous lupus, lichen simplex chronicus, xeroderma, acne, disease-driven secondary dermatological disorder, ulcer, and a combination thereof. In preferred embodiments, the condition of compromised skin barrier function is selected from eczema, psoriasis, ichthyosis, rosacea, and chronic dry skin.

Identification and/or pre-treatment of the area of skin function (e.g., washing, shaving, or otherwise preparing the area for treatment) may be performed. After the optional pre-treatment, the composition is applied to the area in need of treatment to form the layer over the entire or a portion of the area in need of treatment, thereby treating the conditions of skin function. In certain embodiments wherein the composition is a two-part composition, the first part and the second part are applied either one at a time or in combination to form the layer.

Another aspect of the invention is directed to a method of modifying the surface of the skin. In some embodiments, the surface of the skin is modified chemically by altering its surface pH. In some embodiments, the skin is modified by covering portions of its surface with melanin for UV protection. In some embodiments, the skin is modified by covering portions of its surface with silicone to reduce its friction. In some embodiments, the skin is modified physically, such that eye-bags and/or laugh-lines are reduced. In some embodiments, skin is modified by covering portions of its surface with pigments for cosmetic purposes. In some embodiments, skin is modified by covering portions of its surface with soft-focus elements to modify the appearance of the skin. In some embodiments, skin is modified by covering portions of its surface with components that allow for electrical responses, for example by incorporating graphene or magnetic particles, preferably in Part 1.

Physically such as eye-bag, Optically such as pigments and soft-focus.

Another aspect of the invention is directed to a method of modifying skin tension. A change in skin tension may modify the skin's surface contour and/or the skin's recoil dynamic after stress response. As individuals age, they generally lose skin tension and the recoil dynamic response of the skin.

The amount of the composition applied is determined by the size and location of the area to be treated as well as the type of conditions of skin function, e.g., compromised skin barrier function, to be treated.

The layer may remain over the area until the conditions of compromised skin barrier function resolve, or improve, or maybe removed after an appropriate period of time as determined by a skilled practitioner (e.g., a medical practitioner such as a physician) or by the subject. The application can be repeated as many times as needed in order to achieve a desired result.

Physical properties of the compositions were measured using the methods (either standard or described herein) and devices set forth. Such methods and devices are merely exemplary, and other tests, methods, materials, and/or devices may be known or developed appropriate to test the properties of the compositions disclosed.

Unless otherwise specified, all properties of compositions, layers and/or devices disclosed herein are measured at room temperature (about 22-25° C.) and about 1 atmosphere air pressure.

Rheometer Viscosity Measurement Test

The following test method may be used to determine the dynamic viscosity (Pa·s) of fluid materials at 0.5 s$^{-1}$, using a Bohlin CVO100 Rheometer (Malvern Instruments) mounted with 20 mm Parallel plate geometry. Similar Rheometers can be used for viscosity measurements. For each material tested, at least 3 samples are measured, and average viscosity and standard deviation of the measurements are recorded.

About 1 g of each test sample is required. Visually inspect the sample to ensure the sample appears uniform. Turn on the Bohlin Rheometer and the temperature controller; start the Bohlin software and load the viscosity stability test template; install the geometry and zero the instrument. Make sure that both the geometry and plate are clean, which is critical for accurate test results. Place about 1 g of the test sample onto the bottom plate of the Rheometer in a mound centered below the geometry. Lower the geometry to the correct gap (about 250 µm). Clean any excess sample from the sides of the geometry using the flat end of a spatula. Start the test and allow the test to run to completion, then record the viscosity (Pa·s) data.

Film Durability on Skin Test

Application of Test Composition. Healthy subjects (at least 3) are selected irrespective of age, race or gender. Tests are conducted at room temperature and about 50% relative humidity. Drawn 4×4 cm$^2$ square outlines on selected volar forearm areas using a standard template as guide. Using a balance, weigh out appropriate amounts (e.g., about 0.1 g to about 0.3 g) of the test composition (or about 0.1 g of the first part and about 0.15 g of the second part in cases of a two-part composition) onto weigh boats (in cases of a two-part composition, do not mix). Apply the test composition evenly over the 4×4 cm$^2$ squares on the forearm using a fingertip, preferably wearing finger cot. Make sure that all areas of the squares are covered by the composition. In case of a two-part composition, a clean fingertip or fresh finger cot should be used to spread the second part gently over the first part, covering the entire first part area.

Measurement. The composition is allowed to sit untouched over the area for about 15 minutes. The subject is then allowed to resume daily activities. The subjects are permitted to conduct either only routine daily activities, or routine daily activities with demanding activities, for example, exercising, swimming, steam room, sauna, and the like. The type and length of each demanding activity are recorded. The layers formed by the test composition are left on skin for about 24 hours or more. At certain time points after application of the composition, durability of layers are assessed by measuring the percentage of the area intact on the skin using an 8×8 square grid of 0.5×0.5 cm$^2$ each (total 64 squares). Any excess layer outside of the 4×4 cm$^2$ square area is not considered in the evaluation. Each square is only considered to be durable if there is no visible imperfection, e.g., seams, flaking, cracking, and/or peeling, of the layer. Record the observations.

Set-to-Touch Time and Tack-Free Time of Film Test

This method was modified from ASTM D5895-03 Evaluating Drying or Curing During Film Formation of Organic Coatings Using Mechanical Recorders. The materials and application of test composition to the selected subjects are the same as described in the Film Durability on Skin Test. The test can also be conducted on other substrates instead of human skin, for example, on Cowhide Tooling leather in natural color, polyurethane, or polypropylene substrates with comparable results. For each composition tested, at least 3 samples are tested, and average set-to-touch time, average tack-free time and standard deviation of the measurements are recorded.

Measurement. Start a timer when the test composition (or the second part in case of a two-part composition) is applied to the entire test area on the forearm. Allow the composition to sit untouched over the area for a certain period of time, e.g., 30 seconds or one minute. At certain time points, touch one corner of the test area lightly using a fingertip, and visually evaluate: first the presence or absence of any test composition on the fingertip (Set-to-Touch Time); then the presence or absence of any film surface being pulled up by the fingertip (Tack-Free Time of Film Test). Repeat the fingertip evaluation on untouched portions of the test area at a certain time interval, e.g., every 15 seconds or 30 seconds or one minute. The time at which no more test composition is observed on the fingertip is reported as the "set-to-touch time" of the test composition. The time at which no more film surface is pulled up by the fingertip is reported as the "tack-free time" of the test composition.

Set-to-Touch Time and Tack-Free Time of Film Test In-Vitro

This method was modified from ASTM D5895-03 Evaluating Drying or Curing During Film Formation of Organic Coatings Using Mechanical Recorders. The materials and application of test composition to the selected substrates are described as follows: Place a 50-micron spacer (for example, one layer of 3M Magic Scotch Tape) onto the substrate sheet size 4.5"×1.5", forming an opening rectangular of 3.75"× 0.75", exposing the substrate surface. Apply test composition onto the substrate, then gliding the glass slide back and forth along the spacer edges to deposit a smooth and uniform layer of test composition. The test can also be conducted on many substrates such as on Cowhide Tooling leather in natural color, polyurethane, or polypropylene substrates with comparable results. For each composition tested, at least 3 samples are tested, and average set-to-touch time, average tack-free time and standard deviation of the measurements are recorded.

Measurement. Start a timer when the test composition (or the second part in case of a two-part composition) is applied to the entire test area on the substrate. Allow the test composition to sit untouched over the area at room temperature and ambient humidity for a certain period of time, e.g., 30 seconds or one minute. At certain time points, place a 1.5 cm×4 cm polypropylene sheet on the surface of the test composition, then place a 15 g weight on top of polypropylene sheet. Wait for 2 seconds, before removing the weight and the polypropylene sheet from the surface of the test composition. Visually evaluate: first the presence or absence of any test composition on the polypropylene sheet. Repeat the polypropylene sheet evaluation on untouched portions of the test area at a certain time interval, e.g., every 15 seconds or 30 seconds or one minute. The time at which no more test composition on the polypropylene sheet is observed is reported as the "set-to-touch time" of the test composition. After "set-to-touch time" is reported, transfer the specimen to the 30-degree slope surface to evaluate the "tack-free time". Place the specimen 6 inches up along the slope surface away from the lowest point and secure the specimen on the slope surface. Drop a 1/32" diameter stainless steel ball onto the top part of the film surface from a distance an inch above the film surface. Observe the movement of the stainless steel ball on the film surface as the ball trying to roll down on its own gravity. Report "tack-free time" when the ball is able to roll from the top to the bottom part of the film surface continuously, without any interruption from the frictional film surface as the film becomes tack-free.

Peel Adhesion Test

This test method for adhesive force was developed in accordance with ASTM C794 Adhesion-in-Peel of Elastomeric Joint Sealants. Instron 3342 single column tension/ compression testing system (Instron, Norwood, Mass.) with 100N load cell (Instron #2519-103) mounted with extension grip geometry may be used, with polypropylene sheet of 1/32" thickness as test substrate. Other similar equipment and other soft, flexible test substrates can also be used to measure the peeling force. The materials and application of test composition to the selected substrates are described as follows: Place a 50-micron spacer (for example, one layer of 3M Magic Scotch Tape) onto the substrate sheet size 4.5"×1.5", forming an opening rectangular of 3.75"×0.75", exposing the substrate surface. Apply test composition onto the substrate, then gliding the glass slide back and forth along the spacer edges to deposit a smooth and uniform layer of test composition. Allow the test composition to sit untouched over the area at room temperature and ambient humidity for 3 hours. Then, place a silicone adhesive tape (Mepitac) of 0.75" width on top of the film to fully cover the film surface on the polypropylene substrate, ready for measurement. For each material tested, at least 3 samples are measured, and average peeling force and standard deviation of the measurements are recorded.

Measurement. Partially peel the silicone tape-covered test specimen at one end by hand to separate enough of the silicone tape-covered film from the polypropylene substrate for effective grip by extension grip geometry mounts of the instrument. Secure each peeling side in its own instrument grip. Make sure the strips are clamped substantially parallel to the geometry. Perform the extension test at a rate of 1 mm/s until the two peeling strips separate completely from each other. Record the peeling force vs. time data. The sample's average peeling force (N/m) is calculated by averaging the instantaneous force (N) measured by the instrument during the experiment normalized by the sample width (0.75" or 0.019 m).

Curl Test for Surface Tension of Curved Specimen

The deposition of the test article on substrate such as skin or elastic band or parafilm results in residual compressive stress within the film due to volume loss (strain), which in turn translate to the tensile stress on the underneath substrate. The combined result of the film deposited on substrate could be observed and quantified based on the level of surface curvature of the substrate after the deposition of the film.

To prepare the test article for curl test, first the test article was deposited onto either an elastic synthetic rubber sheet or a parafilm substrate as described earlier in the application of test composition to the selected substrates. The materials and application of test composition to the selected substrates are described as follows: Place a 50-micron spacer (for example, one layer of 3M Magic Scotch Tape) onto the substrate sheet size 4.5"×1.5", forming an opening rectangular of 3.75"×0.75", exposing the substrate surface. Apply test composition onto the substrate, then gliding the glass slide back and forth along the spacer edges to deposit a smooth and uniform layer of test composition. Allow the test composition to sit untouched over the area at room temperature and ambient humidity for 24 hours.

Measurement. Use a Vernier Caliper to measure the end-to-end distance of the width side of the test specimen that is curved upward. The end-to-end distance refers to the chord length, forming an incomplete upward circle where subsequent calculation of corresponding radius of the circle is computed. Report the radius value and its reciprocal as the "curvature" value. Use the curvature value to calculate the surface tension incurred on the substrate. In the case of originally curved surface with inherent surface tension such as skin, the change in surface tension incurred by the deposited top layer, will modify the inherent surface tension accordingly.

Cyclic and Extension Pull Test

These test methods for Cyclic Tensile Residual Strain (Instant Residual Strain), Cyclic Tensile Hysteresis Loss Energy, Tensile (Young's) Modulus, Shear Modulus, Tensile Strength/Maximum Stress, Fracture Strain, and Fracture Toughness was developed to be better suited for the specimens disclosed herein in compliance with ASTM D638, ASTM D412, ASTM D1876 test guidelines. Instron 3342 single column tension/compression testing system (Instron, Norwood, Mass.) with 100N load cell (Instron #2519-103) mounted with extension grip geometry may be used. Other similar equipment can also be used to measure the properties tested herein. For each material tested, at least 3 samples are measured, and average results and standard deviation of the measurements are recorded.

About 10 g of the composition tested is needed for each sample. The samples are cast inside dumbbell shaped molds mounted on Teflon, consistent with the ASTM D638 guidelines. The dimensions of the "neck" of the mold are about 20 mm in length, about 5 mm in width and about 1.5 mm in depth. The dimensions of the "handles/bell" of the mold are about 20 mm in length, about 15 mm in width and about 1.5 mm in depth, which provides adequate area to insure secure slip-free grip during testing. Level the top surface of the filled mold with a smooth microscope slide. Ensure that the molds are filled without voids and the top surface is smooth. The casted samples are allowed to fully cure and dry for about 20 to about 30 hours. The specimens formed are extracted from their individual molds by means of a spatula. Width and thickness of the "neck" of the finished specimens are measured with a caliper, recorded and input into the instrument. The Area of the "neck" portion of the specimen is calculated by its width and thickness.

Layers formed by compositions disclosed herein can also be tested once separated from the substrates. Such a layer can be formed or trimmed into a rectangular shape, and the Area of a cross-section of a layer can be calculated by its width and thickness. In such as case, the ends of the rectangular specimen would be considered the "handle/bell" portions whereas the middle of the rectangular specimen would be considered the "neck" portion.

Mechanical characterization of specimens is carried out on the Instron 3342 (Instron, Norwood Mass.) equipped with 100N load-cell. Dumbbell or rectangular shaped specimens are mounted onto the instrument via Instron 2710-101 grips on each end, which are modified to insure the specimens do not slip or fail inside the grips during testing. The specimen is mounted onto the instrument such that all the rectangular "handle/bell" portions of the specimen and none of the "neck" of the specimen are fixed within the instrument grips. Make sure that the specimen is mounted substantially vertical in both vertical planes. The instrument grip distance is adjusted such that the sample is at neutral extension as indicated by the instrument force being close to zero (±0.01 N).

Two types of tests are performed sequentially on each specimen, first the Cyclic Test followed by the Extension Pull Test. It is noted that the Cyclic Test has negligible effects on the result of the Extension Pull Test on the same specimen. Each test is preprogrammed into the instrument.

Cyclic Test: The Cyclic Test is designed to determine the elasticity of the tested materials by measuring Cyclic Tensile Residual Strain (Instant Residual Strain). Generally, the more elastic the material, the faster it returns to its original shape after deformation. Lower Cyclic Tensile Residual Strain scores indicate better elasticity. For perfectly elastic materials, the Cyclic Tensile Residual Strain and cycle test area should approach zero.

The specimen is mounted onto the instrument as described above. Stretch the specimen slightly at about 1 mm/s by raising the geometry until a force of 0.06-0.08 N is registered by the instrument, record the stretched length of the "neck" portion of the specimen as the initial specimen length. Cyclic extension is performed at about 1 mm/s to a maximum extension of 15% of initial specimen length. A total of 15 (and up to 100) cycles are executed and the stress strain data is recorded.

The Cyclic Tensile Modulus is calculated as the straight line slope of the stress-strain curve of first cycle between 1% and 4% strain. The R squared value of the linear fit should be above 0.99 or the test data should be recorded as outlier and discarded. The Cyclic Tensile Residual Strain is calculated for each cycle as the strain difference between the loading and unloading curves at half the maximum stress achieved during the first cycle. The Cyclic Tensile Residual Strain for the first cycle as well as the average Cyclic Tensile Residual Strain for the 2nd through 12th cycles are recorded. The area bound by the loading and unloading curves of each cycle is also calculated as Cyclic Tensile Hysteresis Loss Energy. Good agreement is observed between the Cyclic Tensile Residual Strain and the calculated cycle area.

The majority of the specimens formed by the compositions disclosed herein are sufficiently flexible and elastic such that the Cyclic Test could be repeated on the same sample without a significant change in calculated properties, which suggests that this test did not result in long lasting changes to the tested specimens.

Extension Pull Test: The Extension Pull Test was used to determine the stiffness and stretchiness/flexibility of a material by measuring the Tensile/Young's Modulus and fracture strain, respectively.

The specimen is mounted onto the instrument as described above. Stretch the specimen slightly at about 10 mm/s by raising the geometry until a force of 0.01-0.02 N is registered by the instrument, record the stretched length of the "neck" portion of the specimen as "Original Length." The extension Tensile/Young's Modulus is calculated as the straight line slope of the stress-strain curve between 6% and 11% strain. The R squared value of the linear fit should be above 0.99 or the Tensile/Young's Modulus is calculated from a more linear 5% strain range on the stress strain curve.

The Shear Modulus is determined from the same strain range as the Tensile/Young's Modulus. Shear Modulus is calculated as the slope of the best line fit between recorded stress and $\alpha - 1/\alpha^2$, where $\alpha$ is 1 plus the instantaneous strain.

Stretch the specimen at about 10 mm/s until it is broken at one side or completely. Record the force applied at the time when the specimen is broken as the "Maximum Tensile Force." Record the length of the "neck" portion of the specimen when it is broken extended beyond the Original Length of the specimen as the "Maximum Elongation Length." Tensile Strength/Maximum Stress is calculated as the Maximum Tensile Force over the Area of the "neck" portion of the specimen. Fracture Strain is calculated as the Maximum Elongation Length as percentage of the Original Length.

Fracture Toughness ($kJ/m^3$) is calculated as the area under the stress-strain curve in the Extension Pull Test. The Yield Strain is determined as the strain at which the measured stress differed by more than 10% from the Neo-Hookean stress; the multiple of Shear Modulus and $(\alpha - 1/\alpha^2)$.

Transepidermal Water Loss (TEWL) Measurement Test

Evaporative water loss measurements provide an instrumental assessment of skin barrier function. Evaporimetry with TEWL Probe is fully described in Grove et al., Comparative metrology of the evaporimeter and the DermaLab® TEWL probe, *Skin Res. & Tech.* 1999, 5:1-8 and Grove et al., Computerized evaporimetry using the DermaLab® TEWL probe, *Skin Res. & Tech.* 1999, 5:9-13. The guidelines established for using the Servo Med Evaporimeter described by Pinnagoda (Pinnagoda et al., Guidelines for transepidermal water loss (TEWL) measurement, *Contact Dermatitis* 1990, 22:164-178) are appropriate for the DermaLab® TEWL Probe as well.

Evaporative water loss measurements can be made using a recently calibrated Servo Med Evaporimeter. Alternatively, these measurements can be made using a recently calibrated cyberDERM RG1 Evaporimeter System (Broomall, Pa.) with TEWL Probes (manufactured by Cortex Technology of Hadsund, Denmark and available in the US through cyberDERM, Inc. Broomall, Pa.), or other similar equipment.

Both Evaporimeters are based on the vapor pressure gradient estimation method pioneered by Gert E. Nilsson (e.g., Nilsson, G. E., Measurement of water exchange through skin, Med Biol Eng Comput 1977, 15:209-218). There are slight dimensional differences and the sensor technology is greatly improved in the DermaLab® TEWL Probe but the underlying principles of the measurement remain the same. Both probes contain two sensors that measure the temperature and relative humidity at two fixed points along the axis normal to the skin surface. This arrangement is such that the device can electronically derive a value that corresponds to evaporative water loss expressed in $gm/(m^2 \cdot hr)$. The Evaporimeter System extracts value of average evaporative water loss rate collected over a twenty-second interval once steady state conditions had been achieved.

Subjects are treated with test compositions on selected volar forearm test areas as described in the Film Durability on Skin Test. Measurements are taken from each of the volar forearm sites prior to treatment and at various time points (for example, at about 1-hour, about 4-hour, about 6-hour, about 12-hour, about 24-hour, about 30-hour, about 36-hour, about 48-hour, or between 48 hours and one week time point) after application of the composition. Measurements are taken following a minimum of 25 minutes acclimation period in a controlled environment with the relative humidity maintained at less than about 50% and temperature maintained at about 19-22° C. Duplicate water loss readings are taken from each site. TEWL properties ($g/(m^2 \cdot hr)$) are calculated based on the data recorded by the instrument.

Optical Measurement Based on Color L*a *b*Test

This test uses a Minolta CR-400 Chroma meter in accordance with the instructions by the manufacturer, which are generally known in the art. Triplicate measurements of L*(D65), a*(D65), and b*(D65) are then collected at >6 different locations of the test articles.

Barrier Protection Test Based on Viral Penetration

Barrier protection test based on viral penetration is performed to evaluate the barrier performance of protective materials, which are intended to protect against blood borne pathogen hazards. Test articles were conditioned for a minimum of 24 hours at 21±5° C. and 60±10% relative humidity (% RH) and then tested for viral penetraton using a φX174 bacteriophage suspension. At the end of the test, the observed side of the test article was rinsed with a sterile medium and assayed for the presence of φX174 bacteriophage. The viral penetration method complies with ISO 16604. Triplicate readings are taken from each test article.

Barrier Protection Test Based on Chemical Protection Against Nickel Contact

Nickel can be detected at the ppm level with a simple spot test containing 1% dimethylglyoxime and 10% ammonium hydroxide solution, which turns pink upon contact with nickel. A 0.2 M solution of nickel (II) sulfate hexahydrate solution is added to a substrate, and both are covered by the test article. The spot test solution is subsequently applied on the test. A change of color to pink indicates that the nickel has penetrated the test article and come in contact with the color solution, or vice versa. In contrast, absence of color change indicates that the test article is not penetrated and that its barrier function is intact.

Barrier Protection Test Based on Protection from Ultraviolet Radiation

The presence of the test article could help reduce the skin absorption of ultraviolet light, particularly when the test article contains SPF active ingredients such as titanium dioxide, zinc oxide, avobenzone, octinoxate, octocrylene, homosalate, or oxybenzone.

To prepare the test article for barrier protection against UV radiation, first the test article was deposited onto a blank Cellophane sheet substrate as described earlier in the application of test composition to the selected substrates. Cellophane sheet size 12.78 cm(L)×8.55 cm(W) is employed to match plateholder of UV-Vis Spectrophotometer. Measure UV absorbance with UV-Vis Spectrophotometer from the wavelength 260 nm to 400 nm with 1 nm scan interval. Report absorption data based on averaged value of at least 4 different spot locations.

EXAMPLES

Example 1: Testing the Properties of the Compositions and the Layers Formed by the Compositions

TABLE 1

Exemplary Methods for Measurement of Physical Properties

| PHYSICAL PROPERTIES | METHODS USED | DEVICE USED |
|---|---|---|
| Viscosity | ASTM C1749 Rheological Properties of Hydraulic Cementious Paste Using a Rotational Rheometer | Rotational Rheometer |
| Glass transition temperature | ASTM D3418-03 Transition Temperatures of Polymers By DSC | Differential Scanning Calorimeter (DSC) |
| Layer Thickness | ASTM D3767 Rubber-Measurement of Dimensions using Cowhide Tooling leather | Mitutoyo Thickness Gauge |
| Weight increase upon exposure to environmental factors | ASTM D2765-95 Determination of Gel Content and Swell Ratio of Crosslinked Ethylene Plastics | Mettler Toledo Weigh Scale |
| Tack free time on skin | Set-to-Touch Time of Film on Skin | Visual Examination |
| Durability on skin | Film Durability on Skin | Visual Examination |
| Adhesive force | Peel Adhesion Test in accordance with ASTM C794 | Instron (Adhesion) |
| Tension of curved specimen | Curl test for surface tension of curved specimen | Instron |
| Surface contour | Vector analysis of surface | Canfield 3D Imaging Optical Coherence Tomography |
| Tensile strength Fracture strain Tensile modulus Fracture toughness Cyclic tensile residual strain Cyclic tensile hysteresis | Cyclic and Extension Pull Test/ ASTM D5083 Tensile Properties of Reinforced Thermosetting Plastics Using Straight-Sided Specimens | Instron (Uniaxial Tensile) |
| Shear modulus | ASTM D4065, D4440, D5279 | Dynamic Mechanical Analysis (DMA) Rotational Rheometer |
| Oxygen transmission rate (OTR) Oxygen permeance Oxygen permeability coefficient | ASTM F2622 Oxygen Gas Transmission Rate Through Plastic Film and Sheeting Using Various Sensors | MOCON |
| Water vapor transmission rate (WVTR) Water vapor permeance Water vapor permeability coefficient | ASTM F1249 Water Vapor Transmission Rate Through Plastic Film and Sheeting Using a Modulated Infrared Sensor | MOCON |
| Transepidermal water loss | Transepidermal Water Loss (TEWL) Measurement Test | Servo Med Evaporimeter/ CyberDERM RG1 Evaporimeter System |
| Barrier protection (Biological) | ISO16604 Viral Penetration Test | ΦX Bacteriophage Suspension |
| Barrier protection (Chemical) | Nickel Test | Color assay for nickel contact |
| Barrier protection (Radiation) | Optical Transmission | UV/Vis Spectrophotometer |

TABLE 1-continued

Exemplary Methods for Measurement of Physical Properties

| PHYSICAL PROPERTIES | METHODS USED | DEVICE USED |
|---|---|---|
| Skin hydration | H. Dobrev, "Use of Cutometer to assess epidermal hydration," Skin Research and Technology 2000, 6(4):239-244 | Corneometer |
| Skin hydration | Clarys et al., Hydration measurements of the stratum corneum: comparison between the capacitance method (digital version of the Corneometer CM 825 (R)) and the impedance method (Skicon-200EX (R)), Skin Research and Technology 2011, 18(3):316-23 | Conductance/ Impedance Meter for skin surface |
| Skin retraction time | H. Dobrev, "Use of Cutometer to assess epidermal hydration," Skin Research and Technology 2000, 6(4):239-244 | Cutometer/Suction Cup |
| Color L*; Color a*; Color b* | ASTM E313 Calculating Yellowness and Whiteness Indices from Instrumentally Measured Color Coordinates | Minolta Color Meter |

Example 2: First Part (Formula P-1-001)

TABLE 2

Active Ingredients of Formula P1-001

| Phase | No. | Component | Description | Weight Percent (Wt %) |
|---|---|---|---|---|
| A | 1 | Andisil VS 10,000 | 10,000 cSt Vinyl dimethicone | 70.46% |
| A | 2 | Andisil XL-17 | 50 cSt Hydrogen dimethicone | 17.53% |
| A | 3 | Aerosil R812s | Silica silylate (fumed silica) | 12.01% |

All compositions herein were mixed using Dual Asymmetric Centrifugal Laboratory Mixer System (Hauschild, Germany).

Components 1 and 2 were added to a container and mixed for 2 minutes at 2000 rpm. Then, Component 3 was added to the mixture and mixed for 12 minutes at 2000 rpm (with manual scraping of the walls of the container at every 2 minute interval to ensure complete dispersion of Component 3).

Example 3: First Part (Formula P1-002)

TABLE 3

Active Ingredients of Formula P1-002

| Phase | No. | Component | Description | Wt % |
|---|---|---|---|---|
| A | 1 | Andisil VS 165,000 | 165,000 cSt Vinyl dimethicone | 70.46% |
| A | 2 | Andisil XL-17 | 50 cSt Hydrogen dimethicone | 17.53% |
| A | 3 | Aerosil R812s | Silica silylate (fumed silica) | 12.01% |

Formula P1-002 was prepared using the same method as Formula P1-001.

Example 4: First Part (Formula P1-003)

TABLE 4

Active Ingredients of Formula P1-003

| Phase | No. | Component | Description | Wt % |
|---|---|---|---|---|
| A | 1 | Andisil VS 165,000 | 165,000 cSt Vinyl dimethicone | 3.01% |
| A | 2 | Andisil VS 10,000 | 10,000 cSt Vinyl dimethicone | 48.15% |
| A | 3 | Andisil XL-17 | 50 cSt Hydrogen dimethicone | 25.20% |
| A | 4 | Aerosil R812s | Silica silylate (fumed silica) | 10.91% |
| A | 5 | Silsoft ETS | Ethyl Trisiloxane | 5.45% |
| A | 6 | Jeechem BUGL | Butylene Glycol | 7.27% |

Components 1-3 were added to a container and mixed for 2 minutes at 2000 rpm. Component 4 was added to the mixture and mixed for 12 minutes at 2000 rpm (with manual scraping of the walls of the container at every 2-minute interval to ensure complete dispersion of Component 4). Component 5 was slowly added to the mixture and mixed for 5 minutes at 500 rpm. Component 6 was slowly added to the mixture and mixed for 30 minutes at 500 rpm.

Example 5: First Part (Formula P1-004)

TABLE 5

Active Ingredients of Formula P1-004

| Phase | No. | Component | Description | Wt % |
|---|---|---|---|---|
| A | 1 | Andisil VS 165,000 | 165,000 cSt Vinyl dimethicone | 3.31% |
| A | 2 | Andisil VS 10,000 | 10,000 cSt Vinyl dimethicone | 52.97% |
| A | 3 | Andisil XL-17 | 50 cSt Hydrogen dimethicone | 27.72% |
| A | 4 | Aerosil R812s | Silica silylate (fumed silica) | 7.00% |

TABLE 5-continued

Active Ingredients of Formula P1-004

| Phase | No. | Component | Description | Wt % |
|---|---|---|---|---|
| A | 5 | Aerosil R8200 | Silica silylate (fumed silica) | 9.00% |

Components 1-3 were added to a container and mixed for 2 minutes at 2000 rpm. Component 4 was added to the mixture and mixed for 12 minutes at 2000 rpm (with manual scraping of the walls of the container at every 2-minute interval to ensure complete dispersion of Component 4). Component 5 was added to the mixture and mixed for 12 minutes at 2000 rpm (with manual scraping of the walls of the container at every 2-minute interval to ensure complete dispersion of Component 5).

Example 6: First Part (Formula P1-005)

TABLE 6

Active Ingredients of Formula P1-005

| Phase | No. | Component | Description | Wt % |
|---|---|---|---|---|
| A | 1 | Andisil VS 165,000 | 165,000 cSt Vinyl dimethicone | 9.92% |
| A | 2 | Andisil VS 10,000 | 10,000 cSt Vinyl dimethicone | 42.40% |
| A | 3 | Andisil XL-11 | 45 cSt Hydrogen dimethicone | 20.75% |
| A | 4 | Aerosil R8200 | Silica silylate (fumed silica) | 26.93% |

Components 1-3 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4).

Example 7: First Part (Formula P1-006)

TABLE 7

Active Ingredients of Formula P1-006

| Phase | No. | Component | Description | Wt % |
|---|---|---|---|---|
| A | 1 | Andisil VS 165,000 | 165,000 cSt Vinyl dimethicone | 12.19% |
| A | 2 | Andisil VS 10,000 | 10,000 cSt Vinyl dimethicone | 60.96% |
| A | 3 | Andisil XL-11 | 45 cSt Hydrogen dimethicone | 14.85% |
| A | 4 | Aerosil R812s | Silica silylate (fumed silica) | 12.00% |

Formula P1-006 was prepared using the same method as Formula P1-005.

Example 8: First Part (Formula P1-007)

TABLE 8

Active Ingredients of Formula P1-007

| Phase | No. | Component | Description | Wt % |
|---|---|---|---|---|
| A | 1 | Andisil VS 165,000 | 165,000 cSt Vinyl dimethicone | 14.69% |
| A | 2 | Andisil VS 10,000 | 10,000 cSt Vinyl dimethicone | 58.78% |
| A | 3 | Andisil XL-11 | 45 cSt Hydrogen dimethicone | 14.53% |
| A | 4 | Aerosil R812s | Silica silylate (fumed silica) | 12.00% |

Formula P1-007 was prepared using the same method as Formula P1-005.

Example 9: First Part (Formula P1-008)

TABLE 9

Active Ingredients of Formula P1-008

| Phase | No. | Component | Description | Wt % |
|---|---|---|---|---|
| A | 1 | Andisil VS 165,000 | 165,000 cSt Vinyl dimethicone | 24.94% |
| A | 2 | Andisil VS 10,000 | 10,000 cSt Vinyl dimethicone | 49.88% |
| A | 3 | Andisil XL-11 | 45 cSt Hydrogen dimethicone | 13.18% |
| A | 4 | Aerosil R812s | Silica silylate (fumed silica) | 12.00% |

Formula P1-008 was prepared using the same method as Formula P1-005.

Example 10: First Part (Formula P1-009)

TABLE 10

Active Ingredients of Formula P1-009

| Phase | No. | Component | Description | Wt % |
|---|---|---|---|---|
| A | 1 | Andisil VS 165,000 | 165,000 cSt Vinyl dimethicone | 36.98% |
| A | 2 | Andisil VS 10,000 | 10,000 cSt Vinyl dimethicone | 36.98% |
| A | 3 | Andisil XL-11 | 45 cSt Hydrogen dimethicone | 11.05% |
| A | 4 | Aerosil R812s | Silica silylate (fumed silica) | 15.00% |

Formula P1-009 was prepared using the same method as Formula P1-005.

Example 11: First Part (Formula P1-010)

TABLE 11

Active Ingredients of Formula P1-010

| Phase | No. | Component | Description | Wt % |
|---|---|---|---|---|
| A | 1 | Andisil VS 165,000 | 165,000 cSt Vinyl dimethicone | 56.50% |
| A | 2 | Andisil XL-17 | 50 cSt Hydrogen dimethicone | 14.05% |
| A | 3 | Aerosil R812s | Silica silylate (fumed silica) | 9.63% |
| A | 4 | Silsoft ETS | Ethyl Trisiloxane | 19.81% |

Components 1-3 were mixed to form Formula P1-002 as described. Then, Component 4 was slowly added to the mixture and mixed for 30 minutes at 500 rpm.

Example 12: First Part (Formula P1-011)

TABLE 12

Active Ingredients of Formula P1-011

| Phase | No. | Component | Description | Wt % |
|---|---|---|---|---|
| A | 1 | Andisil VS 165,000 | 165,000 cSt Vinyl dimethicone | 52.84% |
| A | 2 | Andisil XL-17 | 50 cSt Hydrogen dimethicone | 13.15% |
| A | 3 | Aerosil R812s | Silica silylate (fumed silica) | 9.01% |
| A | 4 | Xiameter PMX-1184 | Dimethicone and Trisiloxane | 25.00% |

Components 1-3 were mixed to form Formula P1-002 as described. Then, Component 4 was slowly added to the mixture and mixed for 30 minutes at 500 rpm.

Example 13: First Part (Formula P1-012)

TABLE 13

Active Ingredients of Formula P1-012

| Phase | No. | Component | Description | Wt % |
|---|---|---|---|---|
| A | 1 | Andisil VS 165,000 | 165,000 cSt Vinyl dimethicone | 52.84% |
| A | 2 | Andisil XL-17 | 50 cSt Hydrogen dimethicone | 13.15% |
| A | 3 | Aerosil R812s | Silica silylate (fumed silica) | 9.00% |
| A | 4 | Andisil VS 10,000 | 10,000 cSt Vinyl dimethicone | 0.01% |
| A | 5 | Xiameter PMX-1184 | Dimethicone and Trisiloxane | 25.00% |

Components 1-3 were mixed to form Formula P1-002 as described. Component 4 was added to the mixture and mixed for 5 minutes at 500 rpm. Then, Component 5 was slowly added to the mixture and mixed for 30 minutes at 500 rpm.

Example 14: First Part (Formula P1-013)

TABLE 14

Active Ingredients of Formula P1-013

| Phase | No. | Component | Description | Wt % |
|---|---|---|---|---|
| A | 1 | Andisil VS 165,000 | 165,000 cSt Vinyl dimethicone | 70.46% |
| A | 2 | Andisil VS 10,000 | 10,000 cSt Vinyl dimethicone | 0.01% |
| A | 3 | Andisil XL-17 | 50 cSt Hydrogen dimethicone | 17.53% |
| A | 4 | Aerosil R812s | Silica silylate (fumed silica) | 12.00% |

Components 1, 2 and 3 were added to a container and mixed for 2 minutes at 2000 rpm. Then, Component 4 was added to the mixture and mixed for 12 minutes at 2000 rpm (with manual scraping of the walls of the container at every 2 minute interval to ensure complete dispersion of Component 4).

Example 15: First Part (Formula P1-014)

TABLE 15

Active Ingredients of Formula P1-014

| Phase | No. | Component | Description | Wt % |
|---|---|---|---|---|
| A | 1 | Andisil VS 165,000 | 165,000 cSt Vinyl dimethicone | 52.84% |
| A | 2 | Andisil VS 10,000 | 10,000 cSt Vinyl dimethicone | 0.01% |
| A | 3 | Andisil XL-17 | 50 cSt Hydrogen dimethicone | 13.15% |
| A | 4 | Aerosil R812s | Silica silylate (fumed silica) | 9.00% |
| A | 5 | Xiameter PMX-1184 | Dimethicone and Trisiloxane | 25.00% |

Components 1-4 were mixed to form Formula P1-013 as described. Then, Component 5 was slowly added to the mixture and mixed for 30 minutes at 500 rpm.

Example 16: First Part (Formula P1-015)

TABLE 16

Active Ingredients of Formula P1-015

| Phase | No. | Component | Description | Wt % |
|---|---|---|---|---|
| A | 1 | Andisil VS 165,000 | 165,000 cSt Vinyl dimethicone | 45.80% |
| A | 2 | Andisil XL-17 | 50 cSt Hydrogen dimethicone | 11.39% |
| A | 3 | Aerosil R812s | Silica silylate (fumed silica) | 7.81% |
| A | 4 | Xiameter PMX-1184 | Dimethicone and Trisiloxane | 35.00% |

Components 1-3 were mixed to form Formula P1-002 as described. Then, Component 4 was slowly added to the mixture and mixed for 30 minutes at 500 rpm.

Example 17: First Part (Formula P1-016)

TABLE 17

Active Ingredients of Formula P1-016

| Phase | No. | Component | Description | Wt % |
|---|---|---|---|---|
| A | 1 | Andisil VS 165,000 | 165,000 cSt Vinyl dimethicone | 45.80% |
| A | 2 | Andisil VS 10,000 | 10,000 cSt Vinyl dimethicone | 0.01% |
| A | 3 | Andisil XL-17 | 50 cSt Hydrogen dimethicone | 11.39% |
| A | 4 | Aerosil R812s | Silica silylate (fumed silica) | 7.80% |
| A | 5 | Xiameter PMX-1184 | Dimethicone and Trisiloxane | 35.00% |

Components 1-4 were mixed to form Formula P1-013 as described. Component 5 was slowly added to the mixture and mixed for 30 minutes at 500 rpm.

Example 18: First Part (Formula P1-017)

TABLE 18

Active Ingredients of Formula P1-017

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-1 | 500 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 19: First Part (Formula P1-018)

TABLE 19

Active Ingredients of Formula P1-018

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-1B | 500 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 20: First Part (Formula P1-019)

TABLE 20

Active Ingredients of Formula P1-019

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-17 | 50 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 21: First Part (Formula P1-020)

TABLE 21

Active Ingredients of Formula P1-020

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-15 | 40 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 22: First Part (Formula P1-021)

TABLE 22

Active Ingredients of Formula P1-021

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-13 | 500 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 23: First Part (Formula P1-022)

TABLE 23

Active Ingredients of Formula P1-022

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-11 | 50 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 24: First Part (Formula P1-023)

TABLE 24

Active Ingredients of Formula P1-023

| Phase | No | Component | Description | Wt % |
|---|---|---|---|---|
| A | 1 | Andisil VS 165,000 | 165,000 cSt Vinyl dimethicone | 45.80% |
| A | 2 | Andisil XL-10 | 45 cSt Hydrogen dimethicone | 11.40% |
| A | 3 | Aerosil R812s | Silica silylate (fumed silica) | 7.80% |
| A | 4 | Xiameter PMX-1184 | Dimethicone and Trisiloxane | 35.00% |

Components 1-3 were mixed to form a pre-mixture, before Component 4 was slowly added to the pre-mixture and mixed for 30 minutes at 500 rpm.

Example 25: First Part (Formula P1-024)

TABLE 25

Active Ingredients of Formula P1-024

| Phase | No | Component | Description | Wt % |
|---|---|---|---|---|
| A | 1 | Andisil VS 65,000 | 65,000 cSt Vinyl dimethicone | 38.50% |
| A | 2 | Andisil CE-4 | 4 cSt Hydrogen dimethicone | 19.64% |
| A | 3 | Aerosil R812s | Silica silylate (fumed silica) | 7.80% |
| A | 4 | Xiameter PMX-1184 | Dimethicone and Trisiloxane | 34.00% |

Components 1-3 were mixed to form a pre-mixture, before Component 4 was slowly added to the pre-mixture and mixed for 30 minutes at 500 rpm.

Example 26: First Part (Formula P1-025)

TABLE 26

Active Ingredients of Formula P1-025

| Phase | No. | Component | Description | Wt % |
|---|---|---|---|---|
| A | 1 | Andisil VS 65,000 | 65,000 cSt Vinyl dimethicone | 10.48% |
| A | 2 | Andisil CE-4 | 4 cSt Hydrogen dimethicone | 47.72% |
| A | 3 | Aerosil R812s | Silica silylate (fumed silica) | 7.80% |
| A | 4 | Xiameter PMX-1184 | Dimethicone and Trisiloxane | 34.00% |

Components 1-3 were mixed to form a pre-mixture, before Component 4 was slowly added to the pre-mixture and mixed for 30 minutes at 500 rpm.

Example 27: First Part (Formula P1-026)

TABLE 27

Active Ingredients of Formula P1-026

| Phase | No | Component | Description | Wt % |
|---|---|---|---|---|
| A | 1 | Andisil VS 165,000 | 165,000 cSt Vinyl dimethicone | 22.80% |
| A | 2 | Andisil XL-17 | 50 cSt Hydrogen dimethicone | 5.70% |
| A | 3 | Aerosil R812s | Silica silylate (fumed silica) | 4.00% |
| A | 4 | Matlake TMO | Titanium dioxide | 5.00% |
| A | 5 | Zano 10 Plus | Zinc oxide | 5.00% |
| A | 6 | Xiameter PMX-1184 | Dimethicone and Trisiloxane | 40.00% |

Components 1-5 were mixed to form a pre-mixture, before Component 6 was slowly added to the pre-mixture and mixed for 30 minutes at 500 rpm.

Example 28: First Part (Formula P1-027)

TABLE 28

Active Ingredients of Formula P1-027

| Phase | No. | Component | Description | Wt % |
|---|---|---|---|---|
| A | 1 | Andisil VS 165,000 | 165,000 cSt Vinyl dimethicone | 41.22% |
| A | 2 | Andisil VS 10,000 | 10,000 cSt Vinyl dimethicone | 0.01% |
| A | 3 | Andisil XL-17 | 50 cSt Hydrogen dimethicone | 10.25% |
| A | 4 | Aerosil R812s | Silica silylate (fumed silica) | 7.02% |
| A | 5 | Xiameter PMX-1184 | Dimethicone and Trisiloxane | 31.50% |
| A | 6 | Shin-Etsu KSG240 | Dimethicone/PEG-10/15 Crosspolymer, Cyclopentasiloxane | 3.50% |
| A | 7 | Dow Corning FZ2233 | Bis-Isobutyl PEG/PPG-10/7/Dimethicone Copolymer | 0.50% |
| B | 8 | PEG-200 | Polyethylene glycol 200 | 5.90% |
| B | 9 | Triamcinolone acetonide | Triamcinolone acetonide | 0.10% |

Components 1-4 were mixed to form Formula P1-013 as described. Component 5-7 was slowly added to the mixture and mixed for 30 minutes at 500 rpm. The resultant Components 1-7 mixture is Phase A. In a separate container, Components 7-12 were mixed for 10 minutes at 400 rpm. The resultant Components 8-9 mixture is Phase B. Phase B was then slowly added to Phase A while mixing at 500 rpm, then stirred for 15 minutes at 500 rpm. The resultant emulsion is then homogenized for 15 minutes at 1150 rpm.

Example 29: First Part (Formula P1-028)

TABLE 29

Active Ingredients of Formula P1-028

| Phase | No | Component | Description | Wt % |
|---|---|---|---|---|
| A | 1 | Andisil VS 165,000 | 165,000 cSt Vinyl dimethicone | 43.97% |
| A | 2 | Andisil VS 10,000 | 10,000 cSt Vinyl dimethicone | 0.01% |
| A | 3 | Andisil XL-17 | 50 cSt Hydrogen dimethicone | 10.93% |
| A | 4 | Aerosil R812s | Silica silylate (fumed silica) | 4.49% |
| A | 5 | Xiameter PMX-1184 | Dimethicone and Trisiloxane | 33.86% |
| A | 6 | Phoenix PS-112 | Dimethicone PEG7 Phosphate | 3.78% |
| A | 7 | Sensient Unicert Red K7053-J | CI 45410 pH-sensitive dye | 0.20% |

Components 1-4 were mixed to form Formula P1-013 as described. Component 5-7 was slowly added to the mixture and mixed for 30 minutes at 500 rpm.

Example 30: First Part (Formula P1-029)

TABLE 30

Active Ingredients of Formula P1-029

| Phase | No | Component | Description | Wt % |
|---|---|---|---|---|
| A | 1 | Andisil VS 165,000 | 165,000 cSt Vinyl dimethicone | 37.77% |
| A | 2 | Andisil VS 10,000 | 10,000 cSt Vinyl dimethicone | 0.01% |
| A | 3 | Andisil XL-17 | 50 cSt Hydrogen dimethicone | 9.39% |
| A | 4 | Aerosil R812s | Silica silylate (fumed silica) | 6.43% |
| A | 5 | Xiameter PMX-1184 | Dimethicone and Trisiloxane | 28.86% |
| A | 6 | Phoenix PS-112 | Dimethicone PEG7 Phosphate | 2.06% |
| A | 7 | Celtig Cicarbo Graphene Nanosheets | Graphene | 15.46% |

Components 1-4 were mixed to form Formula P1-013 as described. Component 5-7 was slowly added to the mixture and mixed for 30 minutes at 500 rpm.

Example 31: First Part (Formula P1-030)

TABLE 31

Active Ingredients of Formula P1-030

| Phase | No | Component | Description | Wt % |
|---|---|---|---|---|
| A | 1 | Andisil VS 165,000 | 165,000 cSt Vinyl dimethicone | 0.68% |
| A | 2 | Andisil VS 10,000 | 10,000 cSt Vinyl dimethicone | 10.85% |
| A | 3 | Andisil XL-11 | 45 cSt Hydrogen dimethicone | 2.55% |
| A | 4 | Aerosil R812s | Silica silylate (fumed silica) | 1.92% |
| A | 5 | Xiameter PMX-1184 | Dimethicone and Trisiloxane | 24.00% |
| A | 6 | Kobo FAS70USI-E | $TiO_2$ white pigment | 47.78% |
| A | 7 | Kobo FAS50EYSI-E | $Fe_2O_3$ yellow dispersion | 9.62% |
| A | 8 | Kobo FAS55EYSI-E | $Fe_2O_3$ red dispersion | 2.05% |
| A | 9 | Kobo FAS60EYSI-E | $Fe_2O_3$ black dispersion | 0.55% |

Components 1-4 were mixed to form Formula P1-013 as described. Component 5-9 was slowly added to the mixture and mixed for 30 minutes at 500 rpm.

Example 32: First Part (Formula P1-031)

TABLE 32

Active Ingredients of Formula P1-031

| Phase | No. | Component | Description | Wt % |
|---|---|---|---|---|
| A | 1 | Andisil VS 165,000 | 165,000 cSt Vinyl dimethicone | 1.19% |
| A | 2 | Andisil VS 10,000 | 10,000 cSt Vinyl dimethicone | 19.00% |
| A | 3 | Andisil XL-11 | 45 cSt Hydrogen dimethicone | 4.45% |
| A | 4 | Aerosil R812s | Silica silylate (fumed silica) | 3.36% |
| A | 5 | Xiameter PMX-1184 | Dimethicone and Trisiloxane | 14.80% |
| A | 6 | Shin-Etsu KSG240 | Dimethicone/PEG-10/15 Crosspolymer, Cyclopentasiloxane | 4.25% |
| A | 7 | Dow Corning FZ2233 | Bis-Isobutyl PEG/PPG-10/7/Dimethicone Copolymer | 0.30% |
| A | 8 | Shin-Etsu KF6048 | Cetyl PEG/PPG-10/1 Dimethicone | 0.50% |
| B | 9 | water | water | 51.23% |
| B | 10 | Jeecide CAP-4 | Phenoxyethanol, Caprylyl Glycol | 0.33% |
| B | 11 | Lubrizol Pemulen TR-2 | Acrylates/C10-30 Alkyl Acrylate Crosspolymer | 0.16% |
| B | 12 | Lubrizol Carbopol Ultrez 10 Polymer | Carbomer | 0.48% |
| B | 13 | Angus AMP-Ultra PC 2000 | Aminomethyl propanol (5% water) | 0.09% |

Components 1-4 were mixed to form Formula P1-013 as described. Component 5-8 was slowly added to the mixture and mixed for 30 minutes at 500 rpm. The resultant Components 1-8 mixture is Phase A. In a separate container, Components 10-12 were gradually added to Component 9 then mixed for 10 minutes at 400 rpm until the mixture is uniform. Then, dropwise add Component 13 then mixed for 10 minutes at 400 rpm. The resultant Components 9-13 mixture is Phase B. Phase B was then slowly added to Phase A while mixing at 500 rpm, then stirred for 15 minutes at 500 rpm. The resultant emulsion is then homogenized for 15 minutes at 1150 rpm.

Example 33: First Part (Formula P1-032)

TABLE 33

Active Ingredients of Formula P1-032

| Phase | No. | Component | Description | Wt % |
|---|---|---|---|---|
| A | 1 | Andisil VS 165,000 | 165,000 cSt Vinyl dimethicone | 46.84% |
| A | 2 | Andisil XL-11 | 45 cSt Hydrogen dimethicone | 11.66% |
| A | 3 | Aerosil R812s | Silica silylate (fumed silica) | 6.50% |
| A | 4 | Xiameter PMX-1184 | Dimethicone and Trisiloxane | 35.00% |

Components 1-3 were mixed to form Formula P1-013 as described. Component 4 was slowly added to the mixture and mixed for 30 minutes at 500 rpm.

Example 34: First Part (Formula P1-033)

TABLE 34

Active Ingredients of Formula P1-033

| Phase | No. | Component | Description | Wt % |
|---|---|---|---|---|
| A | 1 | Andisil VS 165,000 | 165,000 cSt Vinyl dimethicone | 40.54% |
| A | 2 | Andisil XL-11 | 45 cSt Hydrogen dimethicone | 7.87% |
| A | 3 | Aerosil R812s | Silica silylate (fumed silica) | 6.60% |
| A | 4 | Xiameter PMX-1184 | Dimethicone and Trisiloxane | 44.99% |

Components 1-3 were mixed to form Formula P1-013 as described. Component 4 was slowly added to the mixture and mixed for 30 minutes at 500 rpm.

Example 35. Second Part (Formula P2-001)

TABLE 35

Active Ingredients of Formula P2-001

| Phase | No. | Component | Description | Wt % |
|---|---|---|---|---|
| A | 1 | Johnson Matthey C1142AF | Platinum Divinyldisiloxane, Divinyldisiloxane, Vinyl Dimethicone | 99.00% |
| A | 2 | Andisil 2827-186L | Divinyldisiloxane | 1.00% |

Component 2 was added to Component 1 and mixed for 15 minutes at 250 rpm.

Example 36: Second Part (Formula P2-002)

TABLE 36

Active Ingredients of Formula P2-002

| Phase | No. | Component | Description | Wt % |
|---|---|---|---|---|
| A | 1 | Shin-Etsu KF995 | Cyclopentasiloxane | 15.89% |
| A | 2 | Kobo Nylon 10-I2 | Nylon 12, Isopropyl Titanium Triisostearate | 4.50% |
| A | 3 | Dow Corning DC9045 Elastomer blend | Dimethicone Crosspolymer, Cyclopentasiloxane | 10.00% |
| A | 4 | Shin-Etsu KSG240 | Dimethicone/PEG-10/15 Crosspolymer, Cyclopentasiloxane | 4.00% |
| A | 5 | Dow Corning FZ2233 | Bis-Isobutyl PEG/PPG-10/7/Dimethicone Copolymer | 0.10% |
| A | 6 | P2-001 | Platinum Divinyldisiloxane, Divinyldisiloxane, Vinyl Dimethicone | 1.01% |
| B | 7 | DI Water | Water | 29.50% |
| B | 8 | Jeecide CAP-4 | Phenoxyethanol, Caprylyl Glycol | 0.50% |
| B | 9 | Glycerin | Glycerin | 4.00% |
| B | 10 | Propylene Glycol | Propylene Glycol | 20.00% |
| B | 11 | Butylene Glycol | Butylene Glycol | 10.00% |
| B | 12 | Sodium Chloride | Sodium Chloride | 0.50% |

Component 2 was slowly added to Component 1 while mixing at 500 rpm, then stirred for 20 minutes at 500 rpm. Components 3-6 were mixed in a separate container for 5 minutes at 500 rpm. The Components 1-2 mixture was added to the container containing the Components 3-6 mixture, then stirred for 10 minutes at 500 rpm. The resultant Components 1-6 mixture is Phase A. In a separate container, Components 7-12 were mixed for 10 minutes at 400 rpm. The resultant Components 7-12 mixture is Phase B. Phase B was then slowly added to Phase A while mixing at 500 rpm, then stirred for 15 minutes at 500 rpm. The resultant emulsion is then homogenized for 15 minutes at 1150 rpm.

Example 37: Second Part (Formula P2-003)

TABLE 37

Active Ingredients of Formula P2-003

| Phase | No. | Component | Description | Wt % |
|---|---|---|---|---|
| A | 1 | Shin-Etsu KF995 | Cyclopentasiloxane | 10.80% |
| A | 2 | Kobo Nylon 10-I2 | Nylon 12, Isopropyl Titanium Triisostearate | 3.60% |
| A | 3 | Dow Corning DC9045 | Dimethicone Crosspolymer, Cyclopentasiloxane | 9.45% |
| A | 4 | Shin-Etsu KSG240 | Dimethicone/PEG-10/15 Crosspolymer, Cyclopentasiloxane | 3.60% |
| A | 5 | Dow Corning FZ2233 | Bis-Isobutyl PEG/PPG-10/7/Dimethicone Copolymer | 0.45% |
| A | 6 | Andisil VS250 | Vinyl Dimethicone | 2.70% |
| A | 7 | Momentive Tospearl 3000A | Methylsilsesquioxane | 10.00% |
| A | 8 | P2-001 | Platinum Divinyldisiloxane, Divinyldisiloxane, Vinyl Dimethicone | 0.90% |

TABLE 37-continued

Active Ingredients of Formula P2-003

| Phase | No. | Component | Description | Wt % |
|---|---|---|---|---|
| B | 9 | DI Water | Water | 22.05% |
| B | 10 | Jeecide CAP-4 | Phenoxyethanol, Caprylyl Glycol | 0.45% |
| B | 11 | Propylene Glycol | Propylene Glycol | 18.00% |
| B | 12 | Butylene Glycol | Butylene Glycol | 9.00% |
| B | 13 | Baycusan C1008 | Polyurethane 48, Water | 9.00% |

Component 2 was slowly added to Component 1 while mixing at 500 rpm, then stirred for 20 minutes at 500 rpm. Components 3-6 were mixed in a separate container for 5 minutes at 500 rpm. The Components 1-2 mixture was added to the container containing the Components 3-6 mixture, then stirred for 10 minutes at 500 rpm. Component 7 was slowly added to the Components 1-6 mixture while mixing at 500 rpm, then stirred for 5 minutes at 500 rpm. Component 8 was added to the Components 1-7 mixture and stirred for 5 minutes at 500 rpm. The resultant Components 1-8 mixture is Phase A. In a separate container, Components 9-13 were mixed for 10 minutes at 400 rpm. The resultant Components 9-13 mixture is Phase B. Phase B was then slowly added to Phase A while mixing at 500 rpm, then stirred for 15 minutes at 500 rpm. The resultant emulsion was then homogenized for 15 minutes at 1150 rpm.

Example 38: Second Part (Formula P2-004)

TABLE 38

Active Ingredients of Formula P2-004

| Phase | No. | Component | Description | Wt % |
|---|---|---|---|---|
| A | 1 | Shin-Etsu KF995 | Cyclopentasiloxane | 11.39% |
| A | 2 | Kobo Nylon 10-I2 | Nylon 12, Isopropyl Titanium Triisostearate | 3.80% |
| A | 3 | Dow Corning DC9045 | Dimethicone Crosspolymer, Cyclopentasiloxane | 9.975% |
| A | 4 | Shin-Etsu KSG240 | Dimethicone/PEG-10/15 Crosspolymer, Cyclopentasiloxane | 3.80% |
| A | 5 | Dow Corning FZ2233 | Bis-Isobutyl PEG/PPG-10/7/Dimethicone Copolymer | 0.475% |
| A | 6 | Andisil VS250 | Vinyl Dimethicone | 2.85% |
| A | 7 | Momentive Tospearl 3000A | Methylsilsesquioxane | 5.00% |
| A | 8 | P2-001 | Platinum Divinyldisiloxane, Divinyldisiloxane, Vinyl Dimethicone | 0.96% |
| B | 9 | DI Water | Water | 23.275% |
| B | 10 | Jeecide CAP-4 | Phenoxyethanol, Caprylyl Glycol | 0.475% |
| B | 11 | Propylene Glycol | Propylene Glycol | 19.00% |
| B | 12 | Butylene Glycol | Butylene Glycol | 9.50% |
| B | 13 | Baycusan C1008 | Polyurethane 48, Water | 9.50% |

Formula P2-004 was prepared using the same method as Formula P2-003.

Example 39: Second Part (Formula P2-004)

TABLE 39

Active Ingredients of Formula P2-004

| Phase | No. | Component | Description | Wt % |
|---|---|---|---|---|
| A | 1 | Dow Corning DC9045 | Dimethicone Crosspolymer, Cyclopentasiloxane | 41.18% |
| A | 2 | Shin-Etsu KSG240 | Dimethicone/PEG-10/15 Crosspolymer, Cyclopentasiloxane | 29.41% |
| A | 3 | Dow Corning FZ2233 | Bis-Isobutyl PEG/PPG-10/7/Dimethicone Copolymer | 5.88% |
| A | 4 | Andisil VS250 | Vinyl Dimethicone | 17.65% |
| A | 5 | P2-001 | Platinum Divinyldisiloxane, Divinyldisiloxane, Vinyl Dimethicone | 5.88% |

Each component was added and mixed altogether for 15 minutes at 250 rpm.

Example 40: Second Part (Formula P2-005)

TABLE 40

Active Ingredients of Formula P2-005

| Phase | No. | Component | Description | Wt % |
|---|---|---|---|---|
| A | 1 | Dow Corning PMX-200 Fluid, 0.65 CST | Hexamethyldisoloxane | 99.2% |
| A | 2 | P2-001 | Platinum Divinyldisiloxane, Divinyldisiloxane, Vinyl Dimethicone | 0.8% |

Each component was added and mixed altogether for 5 minutes at 50 rpm.

Example 41: Second Part (Formula P2-006)

TABLE 41

Active Ingredients of Formula P2-006

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil 2827-186L | 0.7 cSt Vinyl Dimethicone (Divinyldisiloxane) | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 42: Second Part (Formula P2-007)

TABLE 42

Active Ingredients of Formula P2-007

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VS6 | 6 cSt Vinyl Dimethicone | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 43: Second Part (Formula P2-008)

TABLE 43

Active Ingredients of Formula P2-008

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VS20 | 20 cSt Vinyl Dimethicone | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 44: Second Part (Formula P2-009)

TABLE 44

Active Ingredients of Formula P2-009

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VS250 | 250 cSt Vinyl Dimethicone | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 45: Second Part (Formula P2-010)

TABLE 45

Active Ingredients of Formula P2-010

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VS500 | 500 cSt Vinyl Dimethicone | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 46: Second Part (Formula P2-011)

TABLE 46

Active Ingredients of Formula P2-011

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VS1000 | 1000 cSt Vinyl Dimethicone | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 47: Second Part (Formula P2-012)

TABLE 47

Active Ingredients of Formula P2-012

| Phase | No. | Component | Description | Wt % |
|---|---|---|---|---|
| A | 1 | Dow Corning PMX-200 Fluid, 0.65 CST | Hexamethyldisoloxane | 91.7% |
| A | 2 | Andisil VQM2050 | 1000 cSt Vinyl QM-resin | 7.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 48: Second Part (Formula P2-013)

TABLE 48

Active Ingredients of Formula P2-013

| Phase | No. | Component | Description | Wt % |
|---|---|---|---|---|
| A | 1 | Dow Corning PMX-200 Fluid, 0.65 CST | Hexamethyldisoloxane | 95.7% |
| A | 2 | Andisil VS250 | 250 cSt Vinyl Dimethicone | 2.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 49: Second Part (Formula P2-014)

TABLE 49

Active Ingredients of Formula P2-014

| Phase | No. | Component | Description | Wt % |
|---|---|---|---|---|
| A | 1 | Dow Corning PMX-200 Fluid, 0.65 CST | Hexamethyldisoloxane | 93.2% |
| A | 2 | Andisil VS250 | 250 cSt Vinyl Dimethicone | 5.0% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 50: Second Part (Formula P2-015)

TABLE 50

Active Ingredients of Formula P2-015

| Phase | No. | Component | Description | Wt % |
|---|---|---|---|---|
| A | 1 | Dow Corning PMX-200 Fluid, 0.65 CST | Hexamethyldisoloxane | 89.2% |
| A | 2 | Andisil VS250 | 250 cSt Vinyl Dimethicone | 10.0% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 51: Second Part (Formula P2-016)

TABLE 51

Active Ingredients of Formula P2-016

| Phase | No. | Component | Description | Wt % |
|---|---|---|---|---|
| A | 1 | Dow Corning PMX-200 Fluid, 0.65 CST | Hexamethyldisoloxane | 86.7% |
| A | 2 | Andisil VS250 | 250 cSt Vinyl Dimethicone | 12.5% |
| A | 3 | P2-001 | Platinum Divinyldisiloxane, Divinyldisiloxane, Vinyl Dimethicone | 0.8% |

Each component was added and mixed altogether for 5 minutes at 50 rpm.

Example 52: Second Part (Formula P2-017)

TABLE 52

Active Ingredients of Formula P2-017

| Phase | No. | Component | Description | Wt % |
|---|---|---|---|---|
| A | 1 | Dow Corning PMX-200 Fluid, 0.65 CST | Hexamethyldisoloxane | 89.0% |
| A | 2 | Andisil VS250 | 250 cSt Vinyl Dimethicone | 10.0% |
| A | 3 | P2-001 | Platinum Divinyldisiloxane, Divinyldisiloxane, Vinyl Dimethicone | 1.0% |

Each component was added and mixed altogether for 5 minutes at 50 rpm.

Example 53: Second Part (Formula P2-018)

TABLE 53

Active Ingredients of Formula P2-018

| Phase | No. | Component | Description | Wt % |
|---|---|---|---|---|
| A | 1 | Dow Corning PMX-200 Fluid, 0.65 CST | Hexamethyldisoloxane | 88.8% |
| A | 2 | Andisil VS250 | 250 cSt Vinyl Dimethicone | 10.0% |
| A | 3 | P2-001 | Platinum Divinyldisiloxane, Divinyldisiloxane, Vinyl Dimethicone | 1.2% |

Each component was added and mixed altogether for 5 minutes at 50 rpm.

Example 54: Second Part (Formula P2-019)

TABLE 54

Active Ingredients of Formula P2-019

| Phase | No. | Component | Description | Wt % |
|---|---|---|---|---|
| A | 1 | Dow Corning PMX-200 Fluid, 0.65 CST | Hexamethyldisoloxane | 88.6% |
| A | 2 | Andisil VS250 | 250 cSt Vinyl Dimethicone | 10.0% |
| A | 3 | P2-001 | Platinum Divinyldisiloxane, Divinyldisiloxane, Vinyl Dimethicone | 1.4% |

Each component was added and mixed altogether for 5 minutes at 50 rpm.

Example 55: Second Part (Formula P2-020)

TABLE 55

Active Ingredients of Formula P2-020

| Phase | No. | Component | Description | Wt % |
|---|---|---|---|---|
| A | 1 | Dow Corning PMX-200 Fluid, 0.65 CST | Hexamethyldisoloxane | 74.5% |
| A | 2 | Andisil VS250 | 250 cSt Vinyl Dimethicone | 5.0% |
| A | 3 | P2-001 | Platinum Divinyldisiloxane, Divinyldisiloxane, Vinyl Dimethicone | 1.5% |
| A | 4 | Kobo Nylon 10-I2 | Nylon 12, Isopropyl Titanium Triisostearate | 4.0% |
| A | 5 | Momentive Tospearl 2000B | Methylsilsesquioxane | 3.0% |
| A | 6 | Propylene Glycol | Propylene Glycol | 10.0% |
| A | 7 | Magnesium Sulfate | Magnesium Sulfate | 2.0% |

Each component was added and mixed altogether for 5 minutes at 50 rpm.

Example 56: Second Part (Formula P2-021)

TABLE 56

Active Ingredients of Formula P2-021

| Phase | No. | Component | Description | Wt % |
|---|---|---|---|---|
| A | 1 | P2-001 | Platinum Divinyldisiloxane, Divinyldisiloxane, Vinyl Dimethicone | 1.08% |
| A | 2 | Water | water | 48.96% |
| A | 3 | Ethanol | Ethyl alcohol | 45.26% |
| A | 4 | Baycusan C1008 | Polyurethane 48, Water | 4.17% |
| A | 5 | Lubrizol Carbopol Ultrez 10 Polymer | Carbomer | 0.49% |
| A | 6 | Angus AMP-Ultra PC 2000 | Aminomethyl propanol (5% water) | 0.04% |

Each component was added and mixed altogether for 5 minutes at 50 rpm.

Example 57: Second Part (Formula P2-022)

TABLE 57

Active Ingredients of Formula P2-022

| Phase | No. | Component | Description | Wt % |
|---|---|---|---|---|
| A | 1 | Shin-Etsu KF995 | Cyclopentasiloxane | 10.83% |
| A | 2 | Kobo Nylon 10-I2 | Nylon 12, Isopropyl Titanium Triisostearate | 3.80% |
| A | 3 | Dow Corning DC9045 | Dimethicone Crosspolymer, Cyclopentasiloxane | 10.50% |
| A | 4 | Shin-Etsu KSG240 | Dimethicone/PEG-10/15 Crosspolymer, Cyclopentasiloxane | 3.80% |
| A | 5 | Dow Corning FZ2233 | Bis-Isobutyl PEG/PPG-10/7/Dimethicone Copolymer | 0.475% |
| A | 6 | Andisil VS250 | Vinyl Dimethicone | 2.85% |
| A | 7 | Momentive Tospearl 3000A | Methylsesquioxane | 5.00% |
| A | 8 | P2-001 | Platinum Divinyldisiloxane, Divinyldisiloxane, Vinyl Dimethicone | 0.96% |
| B | 9 | DI Water | Water | 23.275% |
| B | 10 | Jeecide CAP-4 | Phenoxyethanol, Caprylyl Glycol | 0.475% |
| B | 11 | Propylene Glycol | Propylene Glycol | 19.00% |
| B | 12 | Butylene Glycol | Butylene Glycol | 9.50% |
| B | 13 | Baycusan C1008 | Polyurethane 48, Water | 9.50% |

Formula P2-004 was prepared using the same method as Formula P2-003.

Example 58: Second Part (Formula P2-023)

TABLE 58

Active Ingredients of Formula P2-023

| Phase | No. | Component | Description | Wt % |
|---|---|---|---|---|
| A | 1 | Shin-Etsu KF995 | Cyclopentasiloxane | 11.75% |
| A | 2 | Kobo Nylon 10-I2 | Nylon 12, Isopropyl Titanium Triisostearate | 4.00% |
| A | 3 | Dow Corning DC9045 | Dimethicone Crosspolymer, Cyclopentasiloxane | 10.50% |
| A | 4 | Shin-Etsu KSG240 | Dimethicone/PEG-10/15 Crosspolymer, Cyclopentasiloxane | 4.00% |
| A | 5 | Dow Corning FZ2233 | Bis-Isobutyl PEG/PPG-10/7/Dimethicone Copolymer | 0.50% |
| A | 6 | Andisil VS250 | Vinyl Dimethicone | 3.00% |
| A | 7 | P2-001 | Platinum Divinyldisiloxane, Divinyldisiloxane, Vinyl Dimethicone | 1.25% |
| B | 8 | DI Water | Water | 33.80% |
| B | 9 | Jeecide CAP-4 | Phenoxyethanol, Caprylyl Glycol | 0.50% |
| B | 10 | Propylene Glycol | Propylene Glycol | 20.00% |
| B | 11 | Butylene Glycol | Butylene Glycol | 10.00% |
| B | 12 | Sodium Chloride | Sodium Chloride | 0.70% |

Formula P2-004 was prepared using the same method as Formula P2-003.

Example 59. Comparison of Durability and Set-to-Touch Time of Different Formulations

TABLE 59

Durability and Set-to-Touch Time of Different Formulations

| | First part | | | | | |
|---|---|---|---|---|---|---|
| Formula | VS165K * (wt %) | VS10K † (wt %) | Silica ‡ (wt %) | Second part | Durability | Set-to-Touch Time |
| P1-001 | 0 | 70.46 | 12 | P2-002 | ~20 hours | >15 minutes |
| P1-003 | 3.01 | 48.15 | 12.72 | P2-002 | <24 hours | >10 minutes |
| P1-004 | 3.31 | 52.97 | 16.0 | P2-002 | <24 hours | >10 minutes |
| P1-005 | 9.92 | 42.4 | 26.9 | P2-002 | <24 hours | >10 minutes |
| P1-006 | 12.19 | 60.96 | 12 | P2-002 | <24 hours | >10 minutes |
| P1-007 | 14.69 | 58.78 | 12 | P2-002 | <24 hours | >10 minutes |
| P1-008 | 24.94 | 49.88 | 12 | P2-002 | <24 hours | >10 minutes |
| P1-009 | 36.98 | 36.98 | 15 | P2-002 | <24 hours | >10 minutes |
| P1-002 | 70.46 | 0 | 12 | P2-002 | 30-48 hours | >15 minutes |
| P1-010 | 70.46 | 0 | 12 | P2-003 | 24+ hours | ~2 minutes |
| P1-011 | 70.46 | 0 | 12 | P2-003 | 24+ hours | ~2 minutes |
| P1-012 | 70.46 | 0.01 | 12 | P2-003 | 24+ hours | ~2 minutes |

TABLE 59-continued

Durability and Set-to-Touch Time of Different Formulations

| | First part | | | | | |
|---|---|---|---|---|---|---|
| Formula | VS165K * (wt %) | VS10K † (wt %) | Silica ‡ (wt %) | Second part | Durability | Set-to-Touch Time |
| P1-014 | 70.46 | 0.01 | 12 | P2-004 | 24+ hours | ~2 minutes |
| P1-015 | 70.46 | 0 | 12 | P2-004 | 24+ hours | ~2 minutes |

Notes:
* VS165K represents Andisil VS 165,000, a high viscosity alkenyl organopolysiloxane;
† VS10K represents Andisil VS 10,000, a low viscosity alkenyl organopolysiloxane;
‡ Silica represents Aerosil R812s, a fumed silica.

Example 60: Comparison of Durability of P1-016/P2-004 with a Commercial Product

TABLE 60

Comparing Durability of P1-016/P2-004 with a Commercial Product at About 24 Hour Time Point

| Formula | Average Durability | STDEV |
|---|---|---|
| P1-016/P2-004 | 92.45% | 13.00% |
| Commercial Product | 38.45% | 27.06% |

Film Durability on Skin Tests were conducted comparing P1-016/P2-004 and a commercial product in accordance with Yu et al. (U.S. 20130078209), with four healthy subjects having the two formulas applied to skin areas on opposite volar forearms. Durability was determined at about 24 hour time points. Results are also shown in FIG. 1.

Example 61: Comparison of Set-to-Touch Time of P1-016/P2-004 with a Commercial Product

TABLE 61

Comparing Set-to-Touch Time of P1-016/ P2-004 with a Commercial Product

| Formula | Average Set-to-Touch Time | STDEV |
|---|---|---|
| P1-016/P2-004 | 2.33 mins | 0.82 mins |
| Commercial Product | 6.00 mins | 1.73 mins |

Figure 2:
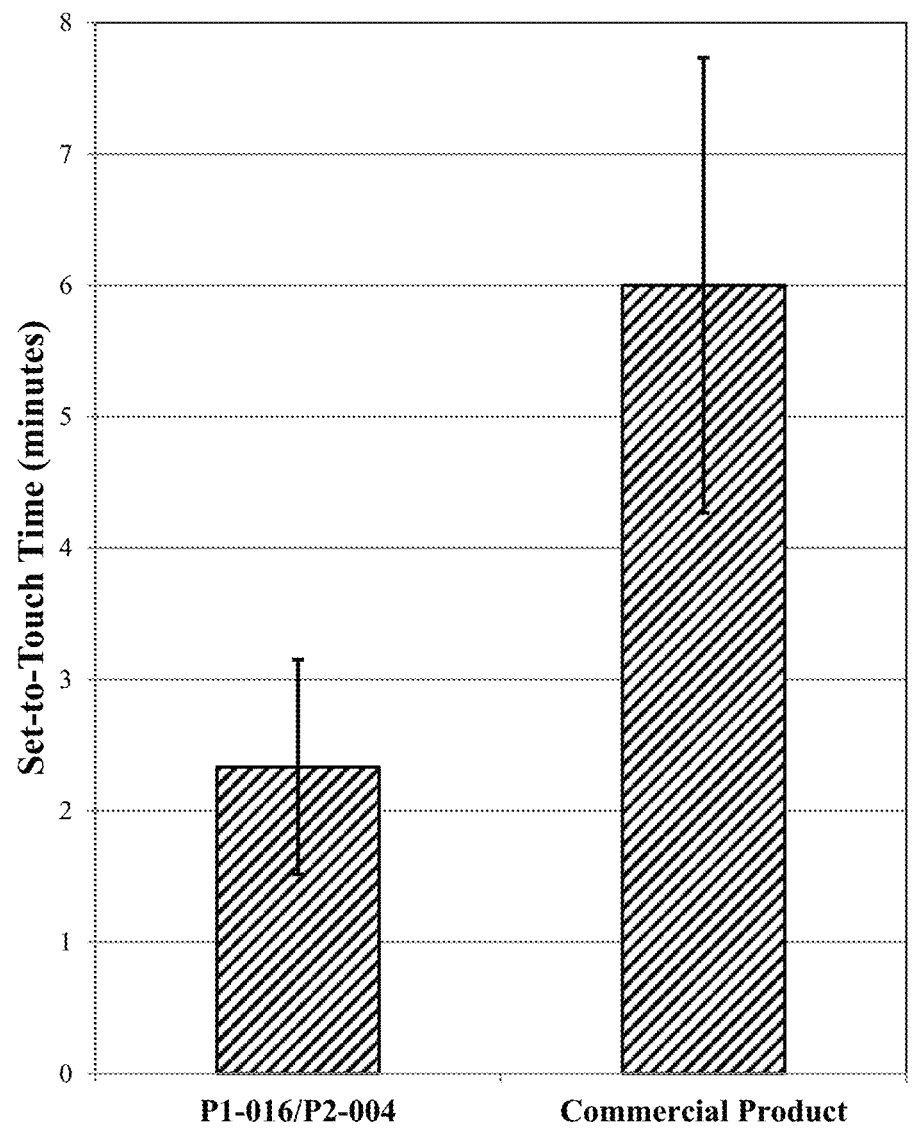
FIG. 2 is a chart illustrating the set-to-touch times of layers formed from P1-016/P2-004 or a commercial product.

Set-to-Touch Time of Film Tests were conducted comparing P1-016/P2-004 and a commercial product in accordance with Yu et al. (U.S. 20130078209). Results are also shown in FIG. 2.

Example 62: Comparison of In-Vivo Set-to-Touch Time and Tack-Free Time of Different Formulations

TABLE 62 in-vivo Set-to-Touch Time and Tack-Free Time of Different Formulations

| First Part | Hydride:Vinyl mole ratio within the First Part | Second Part | Low MW vinyl in Second part | Set-to-touch time (seconds) | Tack-free time (seconds) |
|---|---|---|---|---|---|
| P1-017 | 6:1 | P2-004 | Yes | >15 minutes | >15 minutes |
| P1-018 | 11:1 | P2-004 | Yes | 98 ± 15 seconds | 240 ± 73 seconds |
| P1-019 | 23:1 | P2-004 | Yes | 68 ± 15 seconds | 150 ± 55 seconds |
| P1-020 | 37:1 | P2-004 | Yes | 60 ± 0 seconds | 60 ± 0 seconds |
| P1-021 | 45:1 | P2-004 | Yes | 15 ± 0 seconds | 15 ± 0 seconds |
| P1-022 | 52:1 | P2-004 | Yes | 15 ± 0 seconds | 15 ± 0 seconds |
| P1-023 | 90:1 | P2-004 | Yes | <15 seconds | <15 seconds |

Example 63: Comparison of In-Vitro Set-to-Touch Time and Tack-Free Time of Different Formulations

TABLE 63 in-vitro Set-to-Touch Time and Tack-Free Time of Different Formulations

| First Part | Hydride:Vinyl mole ratio within the First Part | Second Part | Low MW vinyl in Second part | Set-to-touch time (seconds) | Tack-free time (seconds) |
|---|---|---|---|---|---|
| P1-017 | 6:1 | P2-004 | Yes | 860.00 ± 40.00 | 1020.00 ± 30.00 |
| P1-018 | 11:1 | P2-004 | Yes | 286.67 ± 51.32 | 313.33 ± 56.86 |
| P1-019 | 23:1 | P2-004 | Yes | 150.00 ± 10.00 | 190.00 ± 17.32 |
| P1-020 | 37:1 | P2-004 | Yes | 53.33 ± 7.64 | 66.67 ± 11.55 |

TABLE 63-continued in-vitro Set-to-Touch Time and Tack-Free Time of Different Formulations

| First Part | Hydride:Vinyl mole ratio within the First Part | Second Part | Low MW vinyl in Second part | Set-to-touch time (seconds) | Tack-free time (seconds) |
|---|---|---|---|---|---|
| P1-021 | 45:1 | P2-004 | Yes | 51.67 ± 2.89 | 65.00 ± 8.66 |
| P1-022 | 52:1 | P2-004 | Yes | 40.00 ± 0.00 | 50.00 ± 0.00 |
| P1-023 | 90:1 | P2-004 | Yes | 33.33 ± 5.77 | 38.33 ± 10.41 |

Figure 3:
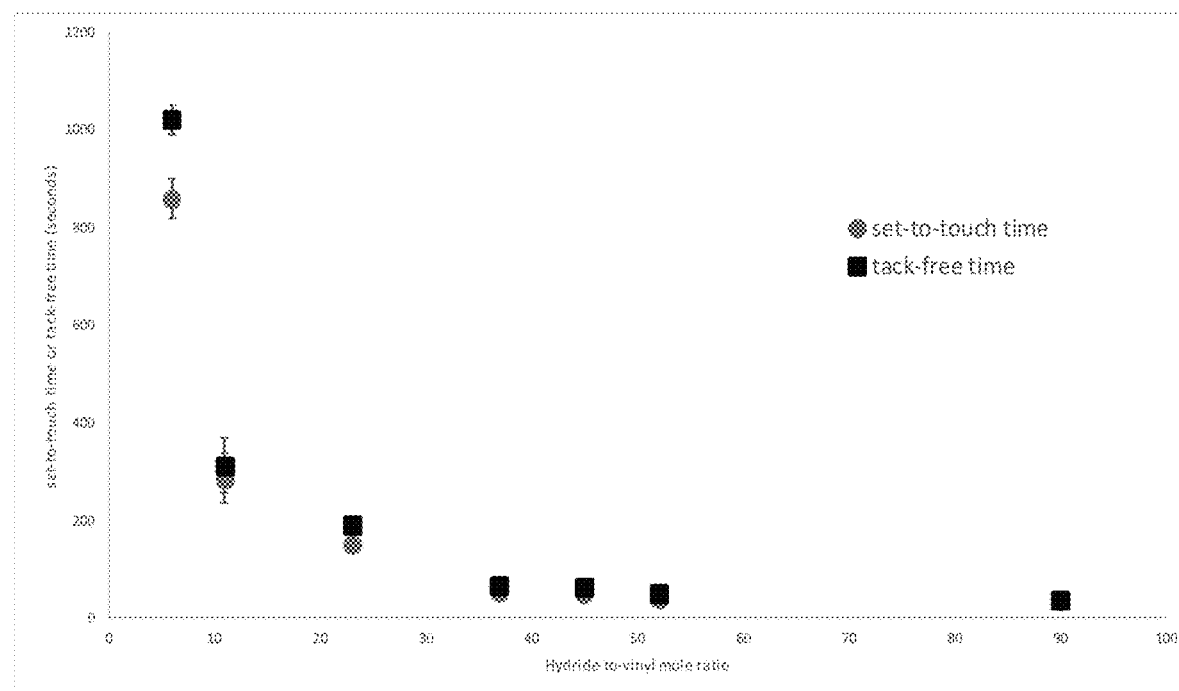
FIG. 3 is a chart illustrating Set-to-Touch Time and Tack-Free Time comparing compositions P1-017/P2-004 to P1-023/P2-004, ranked based on hydride-to-vinyl mole ratio within the first part.

Set-to-Touch Time and Tack-Free Time of Film Tests were conducted comparing P1-017/P2-004 to P1-023/P2-004 ranking based on relative hydride-to-vinyl mole ratio within the first part. Results are also shown in FIG. 3.

Example 64: Comparison of In-Vivo Set-to-Touch Time and Tack-Free Time of Different Formulations

TABLE 64 in-vivo Set-to-Touch Time and Tack-Free Time of Different Formulations

| First Part | Hydride:Vinyl mole ratio within the First Part | Second Part | Low MW vinyl in Second part | Set-to-touch time |
|---|---|---|---|---|
| P1-023 | 1:1 | P2-002 | No | >15 mins |
| P1-023 | 1:1 | P2-004 | Yes | 10-15 mins |
| P1-024 | 10:1 | P2-002 | No | 10-15 mins |
| P1-024 | 10:1 | P2-004 | Yes | 5-10 mins |
| P1-016 | 20:1 | P2-004 | Yes | <2 mins |

Example 65: Comparison of In-Vitro Set-to-Touch Time and Tack-Free Time of Different Formulations

TABLE 65 in-vitro Set-to-Touch Time and Tack-Free Time of Different Formulations

| First Part | Hydride:Vinyl mole ratio within the First Part | Second Part | Low MW vinyl in Second part | Set-to-touch time (mins) | Tack-free time (mins) |
|---|---|---|---|---|---|
| P1-016 | 20:1 | P2-005 | None | >60 | >60 |
| P1-016 | 20:1 | P2-006 | 7.5% 0.7 cSt vinyl | >60 | >60 |
| P1-016 | 20:1 | P2-007 | 7.5% 6 cSt vinyl | 20 | 21 |
| P1-016 | 20:1 | P2-008 | 7.5% 20 cSt vinyl | 2.5 | 3 |
| P1-016 | 20:1 | P2-009 | 7.5% 250 cSt vinyl | 2.5 | 5 |
| P1-016 | 20:1 | P2-010 | 7.5% 500 cSt vinyl | 2.25 | 30 |
| P1-016 | 20:1 | P2-011 | 7.5% 1000 cSt vinyl | 2.25 | >7 |
| P1-016 | 20:1 | P2-013 | 7.5% 500 cSt vinyl (Q-resin) | 6 | 6 |

Set-to-Touch Time and Tack-Free Time of Film Tests were conducted comparing P1-016/P2-005 to P1-016/P2-013 ranking based on relative vinyl polysiloxane viscosity which directly relate to molecular weight within the second part.

Example 66: Comparison of In-Vitro Set-to-Touch Time and Tack-Free Time of Different Formulations

TABLE 66 in-vitro Set-to-Touch Time and Tack-Free Time of Different Formulations

| First Part | Hydride:Vinyl mole ratio within the First Part | Second Part | 250 cSt vinyl wt % in Second part | Set-to-touch time (mins) | Tack-free time (mins) |
|---|---|---|---|---|---|
| P1-016 | 20:1 | P2-013 | 2.5% | 2.5 | >10 |
| P1-016 | 20:1 | P2-014 | 5.0% | 2.5 | >5 |

TABLE 66-continued in-vitro Set-to-Touch Time and Tack-Free Time of Different Formulations

| First Part | Hydride:Vinyl mole ratio within the First Part | Second Part | 250 cSt vinyl wt % in Second part | Set-to-touch time (mins) | Tack-free time (mins) |
|---|---|---|---|---|---|
| P1-016 | 20:1 | P2-009 | 7.5% | 2.5 | 5 |
| P1-016 | 20:1 | P2-015 | 10.0% | 2.5 | 4 |
| P1-016 | 20:1 | P2-016 | 12.5% | 2.5 | 2.5 |

Set-to-Touch Time and Tack-Free Time of Film Tests were conducted comparing P1-016/P2-013 to P1-016/P2-016 ranking based on relative weight percentage content of vinyl polysiloxane of 250 cSt viscosity in the second part.

Example 67: Comparison of In-Vitro Set-to-Touch Time and Tack-Free Time of Different Formulations

TABLE 67 in-vitro Set-to-Touch Time and Tack-Free Time of Different Formulations

| First Part | Hydride:Vinyl mole ratio within the First Part | Second Part | P2-001 wt % in Second part | Set-to-touch time (mins) | Tack-free time (mins) |
|---|---|---|---|---|---|
| P1-016 | 20:1 | P2-015 | 2.5% | 2.5 | 4 |
| P1-016 | 20:1 | P2-017 | 5.0% | 2.5 | 4 |
| P1-016 | 20:1 | P2-018 | 7.5% | 2.5 | 4 |
| P1-016 | 20:1 | P2-019 | 10.0% | 2.25 | 3 |

Set-to-Touch Time and Tack-Free Time of Film Tests were conducted comparing P1-016/P2-017 to P1-016/P2-019 ranking based on relative weight percentage content of P2-001 in the second part.

Example 68: Comparison of In-Vivo Durability of Different Formulations after 24 Hours

TABLE 68

Durability on Forearm Skin of Different Formulations after 24 hours

| First Part | Hydride:Vinyl mole ratio within the First Part | Second Part | Low MW vinyl in Second part | 24 hour durability (% intact) |
|---|---|---|---|---|
| P1-017 | 6:1 | P2-004 | Yes | 0% (no cohesive film formation) |
| P1-018 | 11:1 | P2-004 | Yes | 87% ± 16% |
| P1-019 | 23:1 | P2-004 | Yes | 82% ± 11% |
| P1-020 | 37:1 | P2-004 | Yes | 70% ± 22% |
| P1-021 | 45:1 | P2-004 | Yes | 60% ± 20% |
| P1-022 | 52:1 | P2-004 | Yes | 79% ± 12% |
| P1-023 | 90:1 | P2-004 | Yes | 22% ± 28% |

Example 69: Comparison of In-Vitro Peeling Adhesion Test of Different Formulations

TABLE 69 in-vitro Peeling Adhesion Test of Different Formulations on Polypropylene Substrate

| First Part | Hydride:Vinyl mole ratio within the First Part | Second Part | Low MW vinyl in Second part | Adhesion peel force per unit length (N/m) |
|---|---|---|---|---|
| P1-017 | 6:1 | P2-004 | Yes | 8.64 ± 5.52 |
| P1-018 | 11:1 | P2-004 | Yes | 12.67 ± 2.50 |
| P1-019 | 23:1 | P2-004 | Yes | 21.01 ± 4.55 |
| P1-020 | 37:1 | P2-004 | Yes | 8.81 ± 2.66 |
| P1-021 | 45:1 | P2-004 | Yes | 17.25 ± 7.08 |
| P1-022 | 52:1 | P2-004 | Yes | 15.70 ± 5.21 |
| P1-023 | 90:1 | P2-004 | Yes | 9.84 ± 3.16 |

Figure 4:
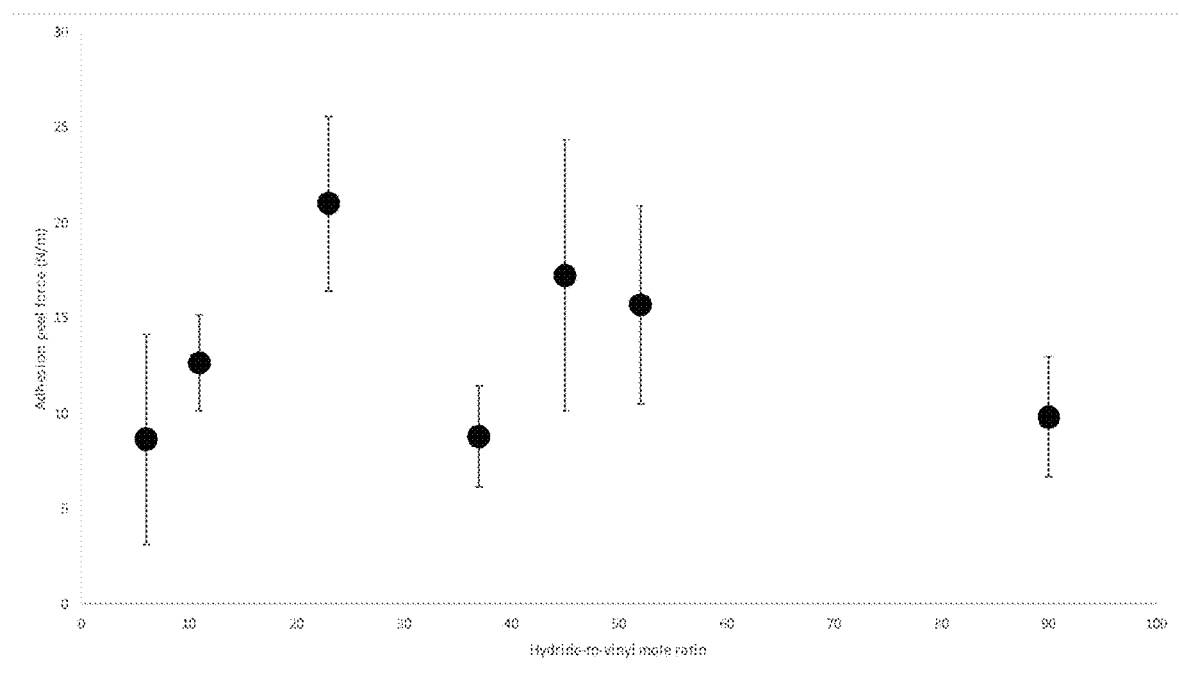
FIG. 4 is a chart illustrating Adhesion Peel Force per unit length comparing compositions P1-017/P2-004 to P1-023/P2-004, ranked based on hydride-to-vinyl mole ratio within the first part.

In-vitro Peeling Adhesion Tests were conducted comparing P1-017/P2-004-P1023/P2-004 ranking based on relative hydride-to-vinyl mole ratio within the first part. Results are also shown in FIG. 4.

Example 70: Demonstration of In-Vivo Film Resistance Against Rubbing

Figure 5:
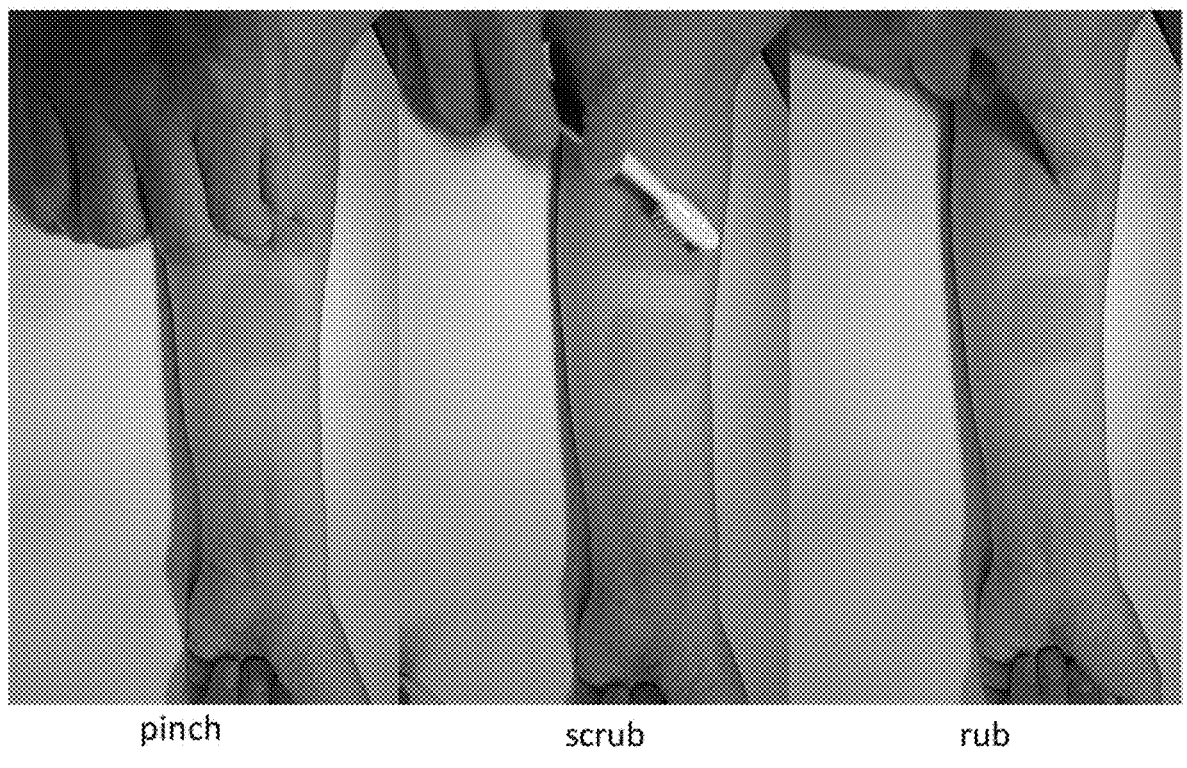
FIG. 5 is a photoset illustrating in-vivo film resistance against rubbing of the test composition P1-030/P2-021 (full coverage colored film) and P1-028/P2-004 (transparent colored film) on skin.

In-vivo film resistance against rubbing of the test composition P1-030/P2-021 (full coverage colored film) and P1-028/P2-004 (transparent colored film) on skin was demonstrated visually in FIG. 5.

Figure 6:
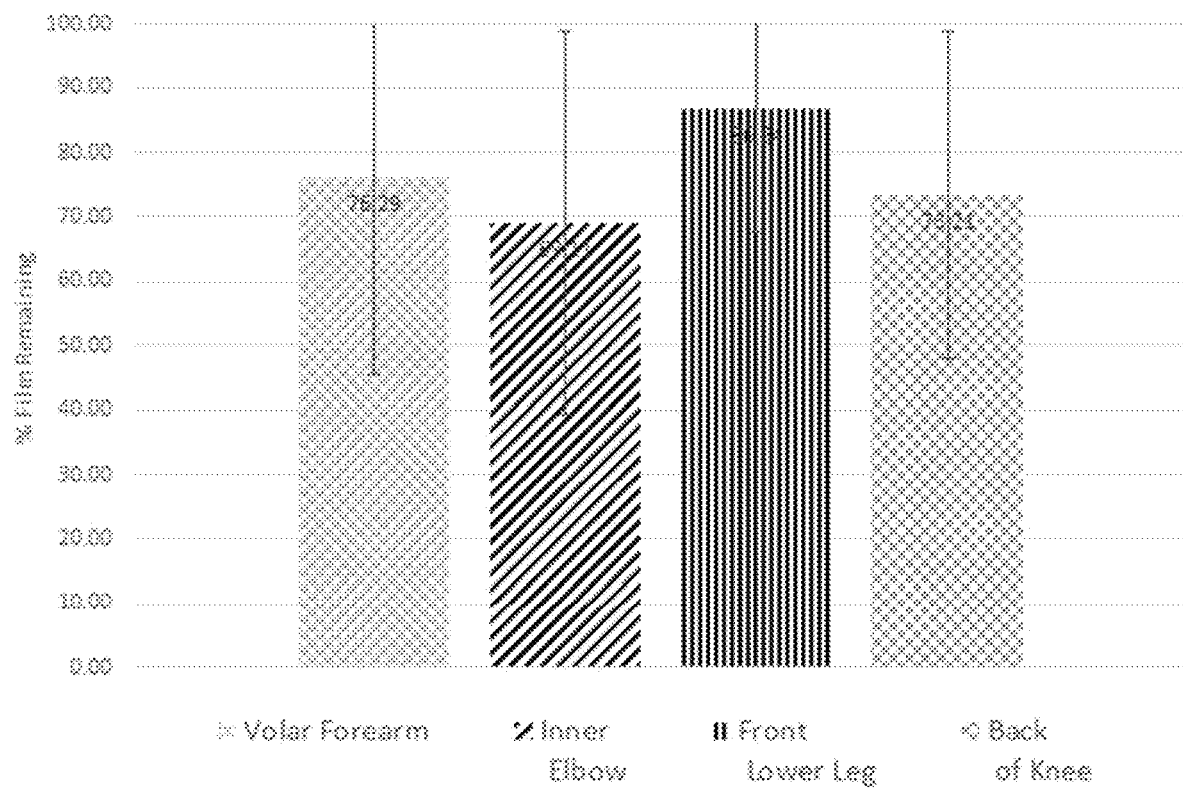
FIG. 6 is a chart illustrating clinical evaluation of in-vivo Durability after 6 hours and 24 hours of P1-016/P2-004 on skin.

Example 71: Clinical Evaluation of In-Vivo Durability after 6 Hours and 24 Hours Clinical Study (S16-01) was based on 25 healthy volunteers with normal skin. The test composition was self-applied under technician instructions on 4 test sites (forearm, inner elbow, leg, behind knee). Each test site covered the area of 4 cm×4 cm (—0.1% BSA). Durability was visually evaluated after 6 hours and 24 hours by percentage of test composition area remaining after 24 hours and self-taken photographs at 12 hours. In addition, durability was additionally evaluated with the dye exclusion on arm after 24 hours with photos, which also visually showed film barrier properties. Results are also shown in FIG. 6.

Example 72: Comparison of In-Vitro Mechanical Properties of Different Formulations In-vitro mechanical properties were conducted comparing P1-017/P2-004-P1023/P2-004 ranking based on relative hydride-to-vinyl mole ratio within the first part.

TABLE 70 in-vitro Tensile Fracture Test for Mechanical Properties of Different Formulations

| First Part | Hydride:Vinyl mole ratio within the First Part | Second Part | Low MW vinyl in Second part | Tensile Strength (MPa) | Tensile Modulus (MPa) | Fracture Strain (%) | Fracture Toughness (MJ/m³) |
|---|---|---|---|---|---|---|---|
| P1-017 | 6:1 | P2-004 | Yes | did not cure into a cohesive test specimen after 24 hours | | | |
| P1-018 | 11:1 | P2-004 | Yes | 0.54 ± 0.15 | 0.34 ± 0.02 | 327.77 ± 91.44% | 1.02 ± 0.53 |
| P1-019 | 23:1 | P2-004 | Yes | 0.82 ± 0.24 | 0.34 ± 0.02 | 436.15 ± 110.54% | 1.88 ± 0.87 |
| P1-020 | 37:1 | P2-004 | Yes | 0.78 ± 0.09 | 0.38 ± 0.02 | 478.34 ± 52.57% | 1.98 ± 0.39 |
| P1-021 | 45:1 | P2-004 | Yes | 0.88 ± 0.31 | 0.43 ± 0.02 | 406.32 ± 140.56% | 2.03 ± 1.37 |
| P1-022 | 52:1 | P2-004 | Yes | 0.78 ± 0.12 | 0.35 ± 0.03 | 530.30 ± 54.97% | 2.28 ± 0.60 |
| P1-023 | 90:1 | P2-004 | Yes | 0.88 ± 0.19 | 0.63 ± 0.06 | 270.80 ± 43.89% | 1.31 ± 0.44 |

TABLE 71 in-vitro Cyclic Tensile Test for Elasticity of Different Formulations

| First Part | Hydride:Vinyl mole ratio within the First Part | Second Part | Low MW vinyl in Second part | Cyclic Tensile Residual Strain (%) | Cyclic Tensile Residual Hysteresis-Hysteresis Loss Energy (kJ/m³) |
|---|---|---|---|---|---|
| P1-017 | 6:1 | P2-004 | Yes | did not cure into a cohesive test specimen after 24 hours | |
| P1-018 | 11:1 | P2-004 | Yes | 1.32 ± 0.26% | 0.383 ± 0.071 |
| P1-019 | 23:1 | P2-004 | Yes | 0.92 ± 0.01% | 0.280 ± 0.027 |
| P1-020 | 37:1 | P2-004 | Yes | 0.91 ± 0.01% | 0.327 ± 0.025 |
| P1-021 | 45:1 | P2-004 | Yes | 0.87 ± 0.03% | 0.353 ± 0.021 |
| P1-022 | 52:1 | P2-004 | Yes | 1.14 ± 0.01% | 0.370 ± 0.027 |
| P1-023 | 90:1 | P2-004 | Yes | 0.65 ± 0.12% | 0.397 ± 0.111 |

Example 73: Comparison of In-Vitro Curl Test of Different Formulations

In-vitro Curl Test were conducted comparing P1-017/P2-004-P1023/P2-004 ranking based on relative hydride-to-vinyl mole ratio within the first part.

TABLE 72 in-vitro Curl Test of Different Formulations

| First Part | Hydride:Vinyl mole ratio within the First Part | Second Part | Low MW vinyl in Second part | Chord Length/Curved Length (mm/mm) | Radius of curvature (mm) | Tensile stress on 500 microns skin thickness, 1 MPa skin modulus (kPa) |
|---|---|---|---|---|---|---|
| P1-017 | 6:1 | P2-004 | Yes | 0.93 ± 0.04 | 17.11 ± 0.01 | 14.61 ± 0.05 |
| P1-018 | 11:1 | P2-004 | Yes | 0.69 ± 0.03 | 8.78 ± 1.45 | 26.21 ± 19.27 |
| P1-019 | 23:1 | P2-004 | Yes | 0.99 ± 0.04 | 19.60 ± 0.00 | 12.76 ± 0.00 |
| P1-020 | 37:1 | P2-004 | Yes | 0.41 ± 0.02 | 5.16 ± 0.43 | 75.88 ± 16.24 |
| P1-021 | 45:1 | P2-004 | Yes | 0.74 ± 0.03 | 11.06 ± 0.09 | 22.60 ± 0.77 |
| P1-022 | 52:1 | P2-004 | Yes | 0.90 ± 0.04 | 16.21 ± 0.09 | 15.42 ± 0.35 |
| P1-023 | 90:1 | P2-004 | Yes | 0.29 ± 0.01 | 3.65 ± 0.06 | 151.66 ± 4.22 |

Example 74: In-Vivo Optical Evaluation of Test Formulation on Forearm Skin

TABLE 73 in-vivo optical evaluation of color L*a*b* scales on test formulation on forearm skin

| | Test Materials | L*(D65) | a*(D65) | b*(D65) |
|---|---|---|---|---|
| 1 | P1-016/P2-004 on skin#1 | 60.38 | 11.72 | 15.74 |
| 2 | P1-016/P2-004 on skin#2 | 59.56 | 11.09 | 15.35 |
| 3 | P1-016/P2-004 on skin#3 | 60.59 | 11.17 | 14.78 |
| 4 | forearm skin#1 | 61.15 | 10.55 | 13.83 |
| 5 | forearm skin#2 | 60.12 | 10.86 | 14.24 |
| 6 | forearm skin#3 | 60.56 | 11.56 | 14.35 |
| 7 | Tegaderm#1 | 65.96 | 7.23 | 14.83 |
| 8 | Tegaderm#2 | 65.24 | 8.69 | 14.97 |
| 9 | Tegarderm#3 | 66.37 | 6.96 | 15.03 |

Figure 7A:
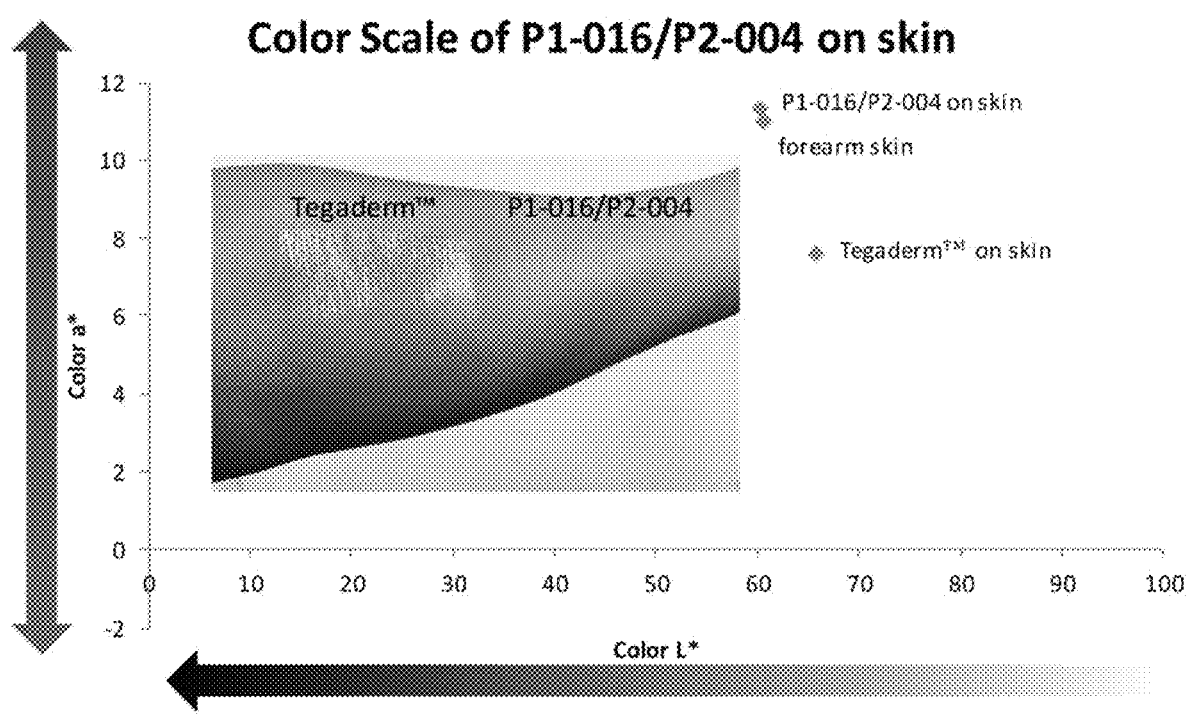
FIG. 7A is a chart illustrating in-vivo optical evaluation of color L*a*b* scales on test formulation on forearm skin, comparing invisibility of composition P1-016/P2-004 with the commercially Tegaderm™ product (3M).
Figure 7B:
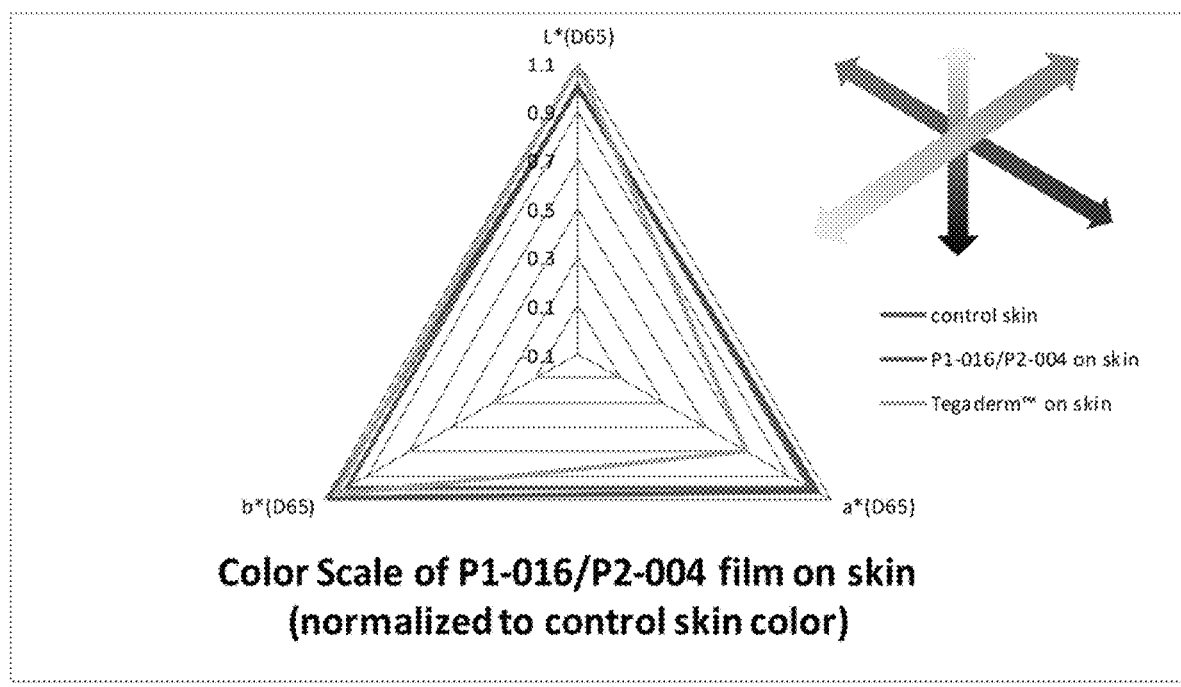
FIG. 7B is a chart illustrating in-vivo optical evaluation of normalized values of color L*a*b* scales on test formulation to the values on forearm skin, comparing invisibility of composition P1-016/P2-004 with the commercially Tegaderm™ product (3M).

The optics was quantified using Minolta Color Meter from the volar forearm location for (i) control skin, (ii) P1-016/P2-004 on skin, (iii) 3M Tegaderm™ wound dressing on skin. The evaluation of optical invisibility is based on grouping as of color L*a*b* scale distance from the control skin. Results are also shown in FIG. 7.

Figure 8:
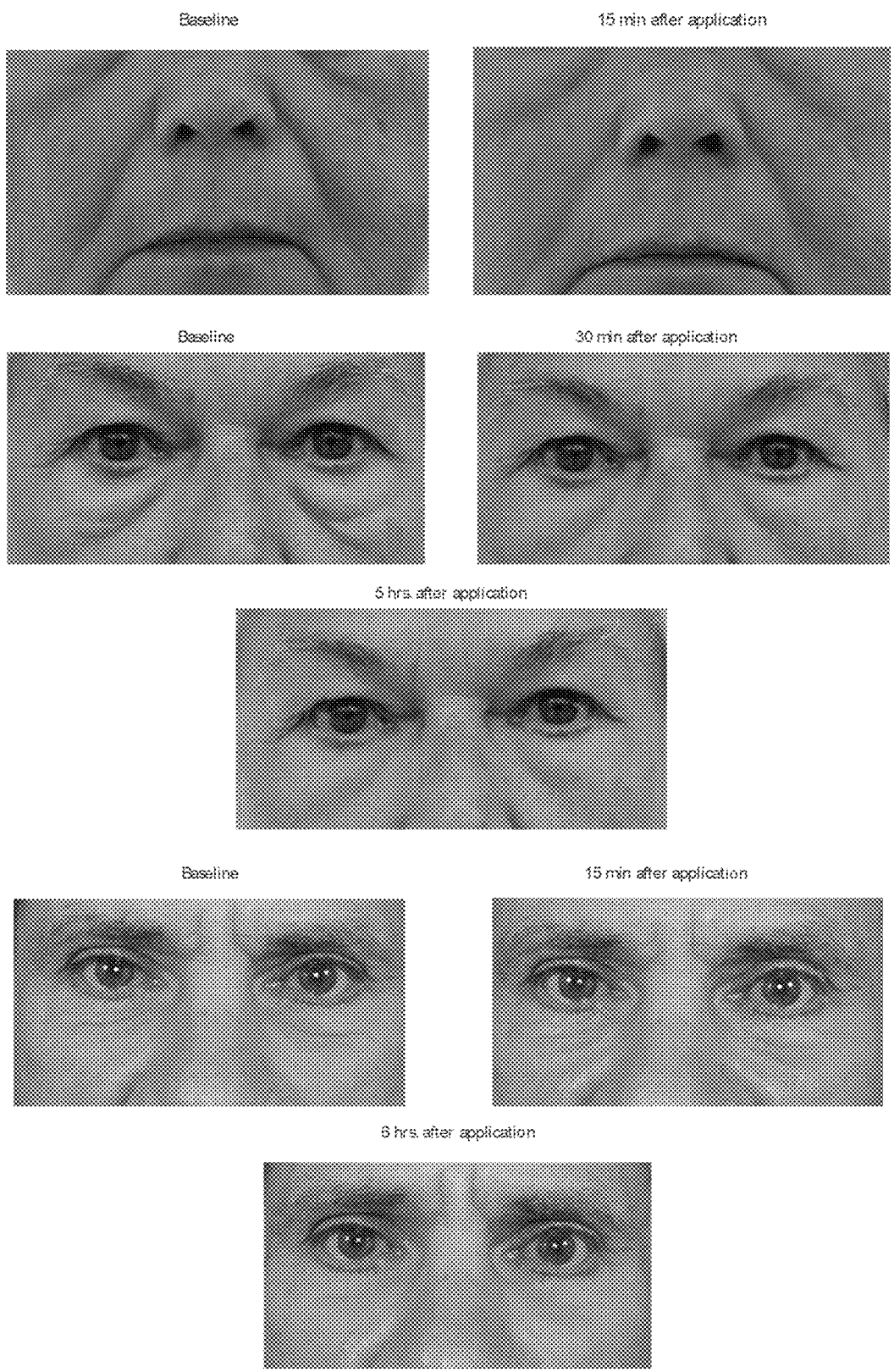
FIG. 8 is a photoset illustrating in-vivo evaluation of skin surface modulation achieved by P1-016/P2-004: (top) on both under eye areas of a male subject, (middle) on both under eye areas of a female subject, (bottom) on both laugh line areas of a female subject.

Example 75: In-Vitro Evaluation of Skin Surface Modulation in-vivo evaluation of skin surface modulation was evaluated visually and demonstrated in FIG. 8 on the modulation of facial contour near the under eye areas as well as near the laugh line areas. The photos were taken before, after 15 minutes and after 6 hours of the application of the test composition by P1-031/P2-022 (Right under eye & laugh line) and P1-032/P2-022 (Left under eye & laugh line) on female test subject (top) and by P1-033/P2-023 (Right under eye & laugh line) and P1-032/P2-023 (Left under eye & laugh line) on male test subjects. All the test composition displayed the flattening appearance of the facial contour.

Example 76: In-Vitro Evaluation of Optical Modification of Skin in-vivo evaluation of optical modification of skin was evaluated visually and demonstrated in FIG. 9 on the complete optical coverage of natural hyperpigmentation and on the complete coverage of tattoo. The photos were taken before and after the application of the test composition by P1-030/P2-021 on forearm skin of the subject.

Figure 10:
FIG. 10 is a photoset illustrating the incorporation of stimuli-responsive components into the test composition on skin. (Left) Composition P1-029/P2-004 includes graphene, and (Right) composition P1-028/P2-004 includes pH-sensitive dye.

Example 77: In-Vivo Demonstration of the Incorporation of Stimuli-Responsive Components into the Test Compositions for Enhancing the Skin Function Demonstration for enhancing the skin function via the incorporation of stimuli-responsive components into the test compositions was shown in FIG. 10, which illustrates the incorporation of two different stimuli-responsive components into the test composition on skin. (Left) P1-029/P2-004 with graphene, and (Right) P1-028/P2-004 with pH-sensitive dye.

Example 78: In-Vivo Barrier Evaluation Against Liquid Water Penetration

Figure 11:
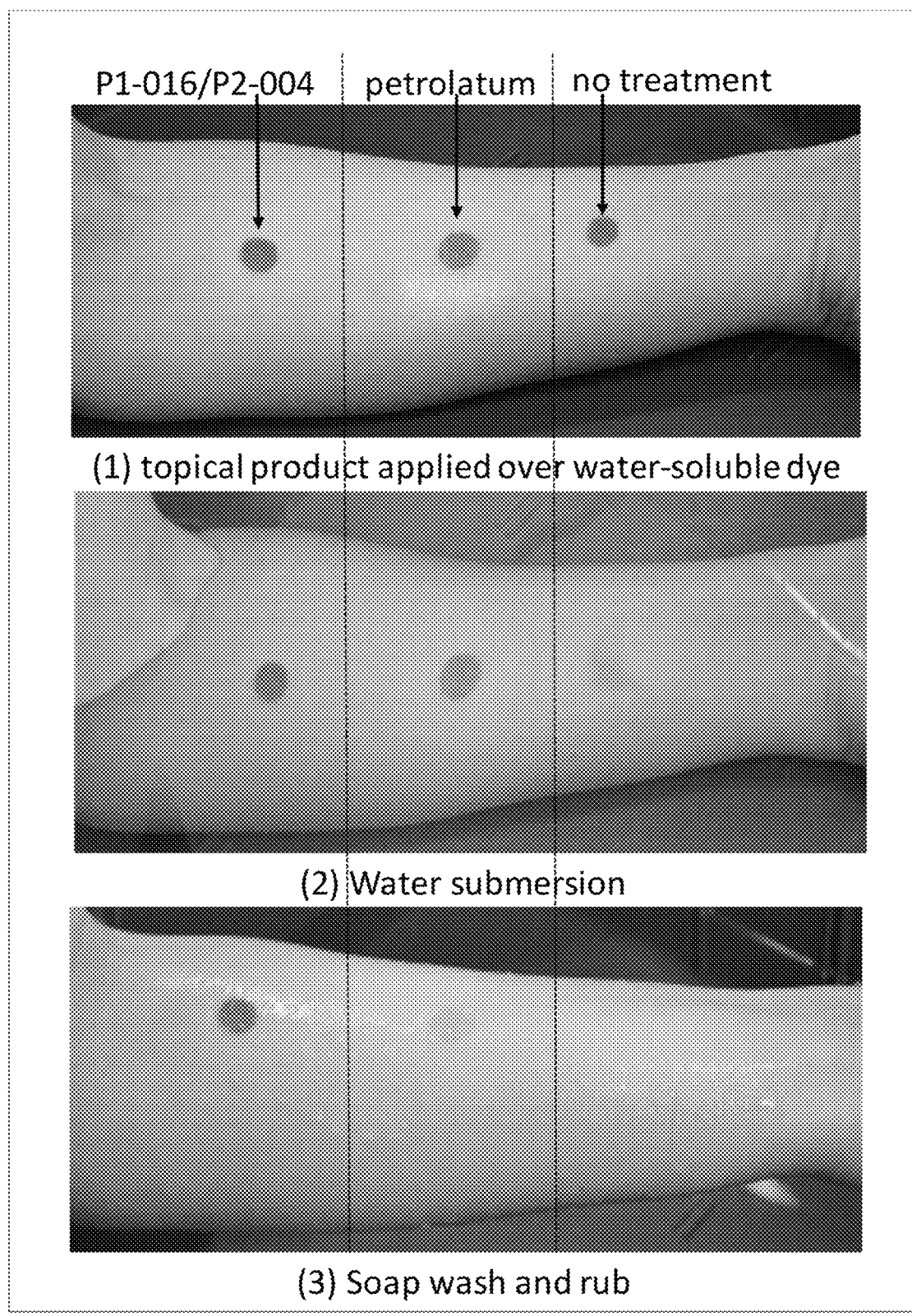
FIG. 11 is a photoset illustrating in-vivo barrier protection against water penetration to demonstrate the waterproof property of the test composition P1-016/P2-004 on skin.

In-vivo barrier evaluation against liquid water penetration were conducted through a demonstration of waterproof property of the test composition P1-016/P2-004, in comparison to petrolatum and control skin. First, a water-soluble dye was deposited on all three sites of the skin prior to the topical application of test compositions. After the topical application of the test compositions, each skin site was then submersed into a water bath, where the water-soluble dye at the control skin site was observed to wash away off the skin. Then, the remaining two sites were washed with soap and hand-rubbed thoroughly, where the water-soluble dye at the petrolatum site was also observed to wash away off the skin after rubbing. The only remaining site of the water-soluble dye on skin was the skin site protected by test composition P1-016/P2-004. The results were illustrated in FIG. 11.

Example 79: In-Vitro Barrier Evaluation Against Viral Penetration

TABLE 74

| | in-vitro barrier evaluation against viral penetration | | | | |
|---|---|---|---|---|---|
| Test article number | Pre-challenge concentration (PFU/mL) | Post-challenge concentration (PFU/mL) | Assay titer (PFU/mL) | Visual Penetration | Test result |
| P1-016/P2-004 | $4.2 \times 10^8$ | $4.9 \times 10^8$ | $<1^a$ | None seen | Pass |
| Negative control | $4.2 \times 10^8$ | $4.9 \times 10^8$ | $<1^a$ | None seen | Acceptable |
| Positive control | $4.2 \times 10^8$ | $4.9 \times 10^8$ | $9.3 \times 10^1$ | Yes | Acceptable |

$^a$ A value of <1 plaque forming units (PFU/mL) is reported for assay plates showing no plaques.

Example 80: In-Vitro Barrier Evaluation Against Nickel Contact

Figure 12:
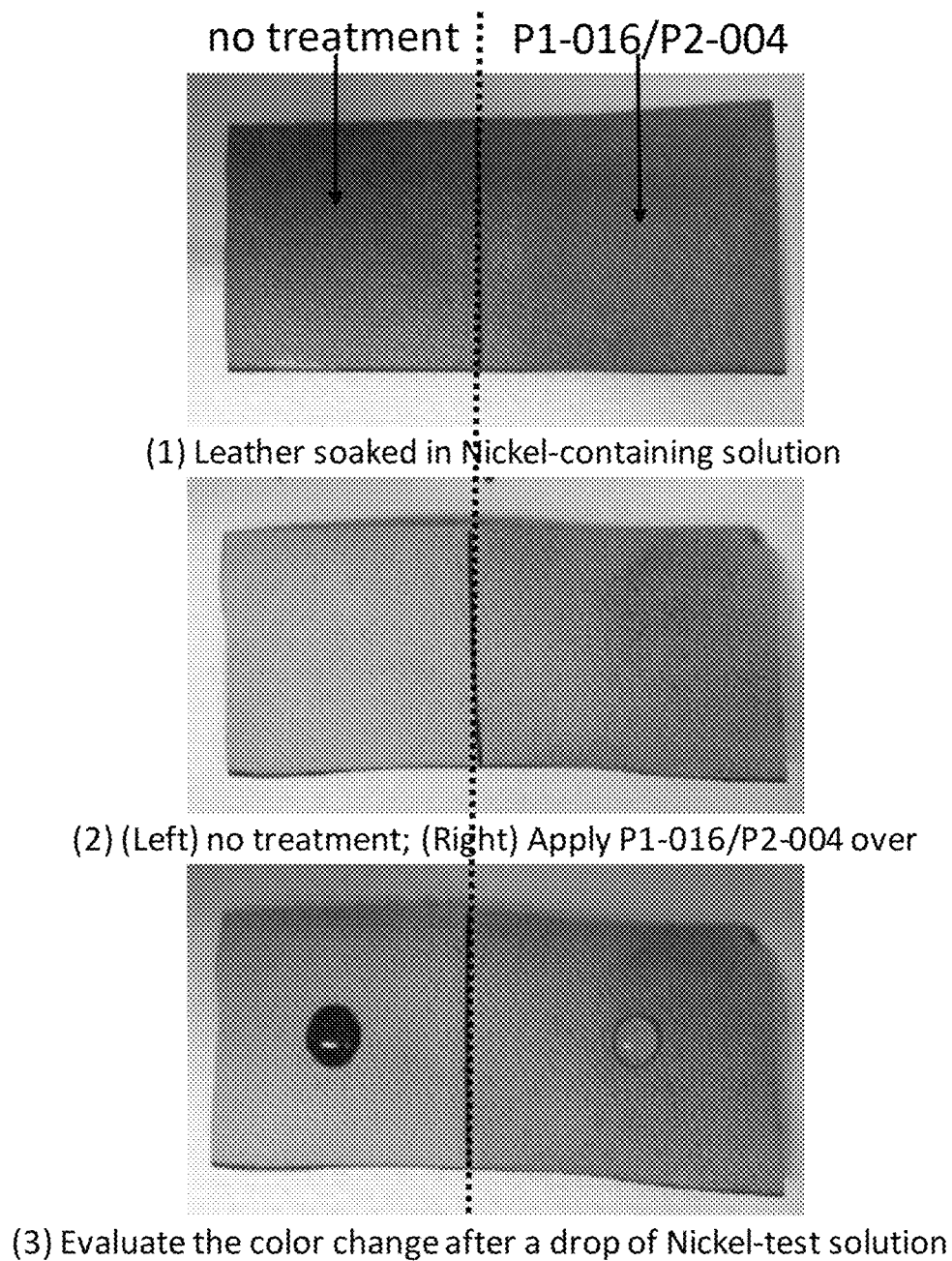
FIG. 12 is a chart illustrating in-vitro barrier evaluation against nickel contact comparing composition P1-016/P2-004 (right side) against control (left side with no test composition). The control (left) displayed color change to pink indicating a direct contact to nickel. In contrast, the right side with the test article P1-016/P2-004 displayed no color change, due to the barrier protection of the film against nickel contact.

In-vitro barrier evaluation against nickel contact were conducted comparing P1-016/P2-004 (right side) against control (left side with no test composition). The control (left) displayed color change to pink indicating a direct contact to nickel. The test composition containing P1-016/P2-004 (right) display no change in color indicating barrier protection of the test article against chemicals such as nickel contact. Results are also shown in FIG. 12.

Example 81: In-Vitro Barrier Evaluation Against UV Radiation

Figure 13:
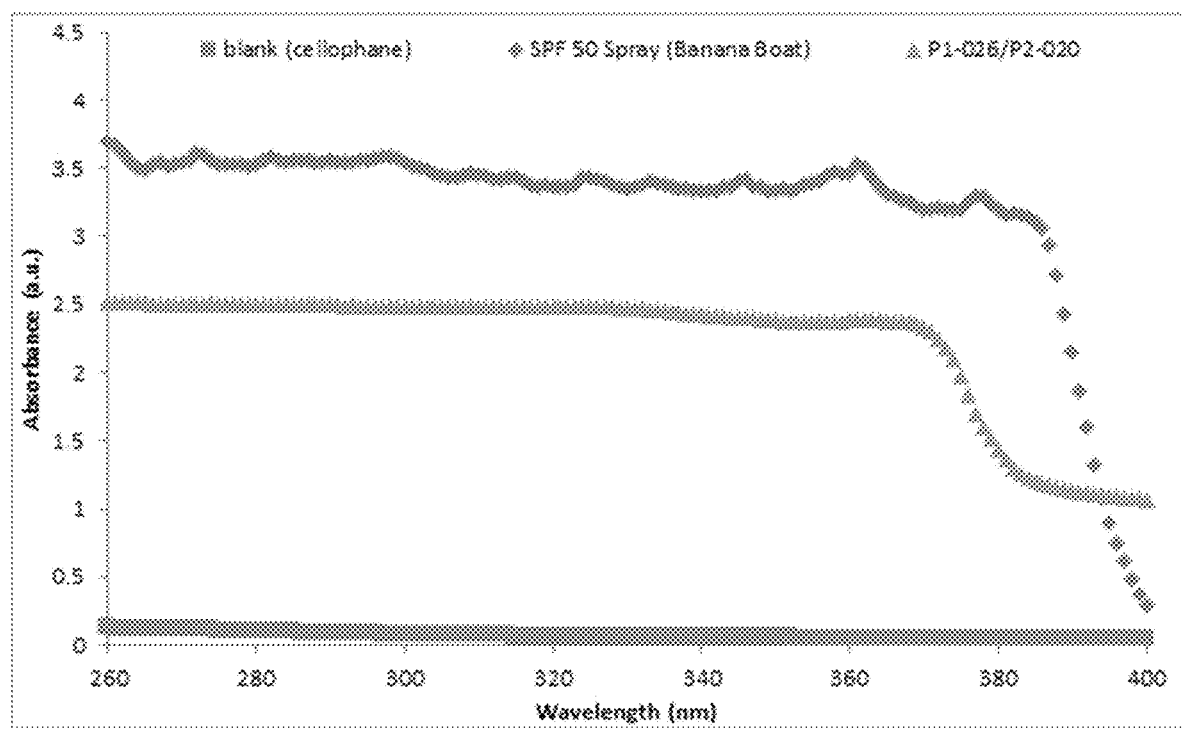
FIG. 13 is a chart illustrating in-vitro barrier evaluation against UV radiation comparing P1-026/P2-004 against control blank and against over-the-counter SPF 50 spray (Banana Boat).

In-vitro barrier evaluation against UV radiation were conducted comparing P1-026/P2-004 against control blank and against over-the-counter SPF 50 spray (Banana Boat). P1-026/P2-004 demonstrated barrier protection against UV radiation, though not as good as SPF 50 spray. Results are also shown in FIG. 13.

Example 82: In-Vitro Water Vapor Transmission Rate

Figure 14A:
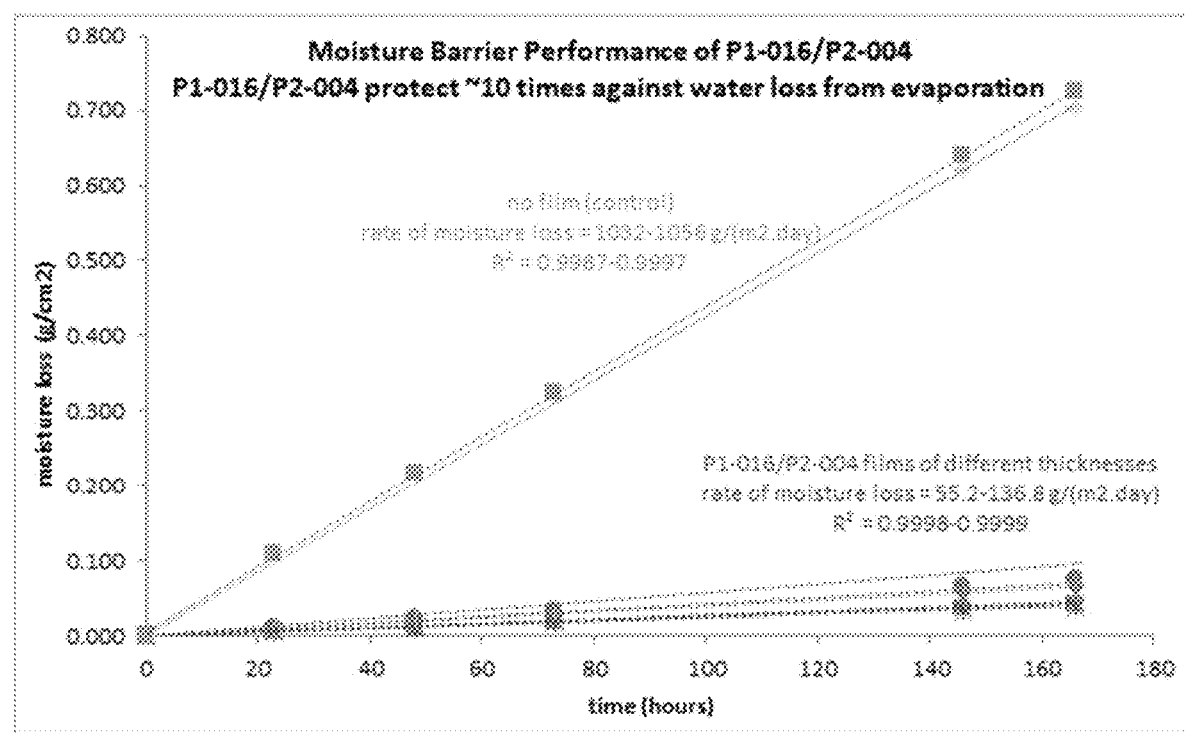
FIG. 14A is a chart illustrating water vapor transmission comparing P1-016/P2-004 (right side) at different thicknesses against control (left side with no test composition).
Figure 14B:
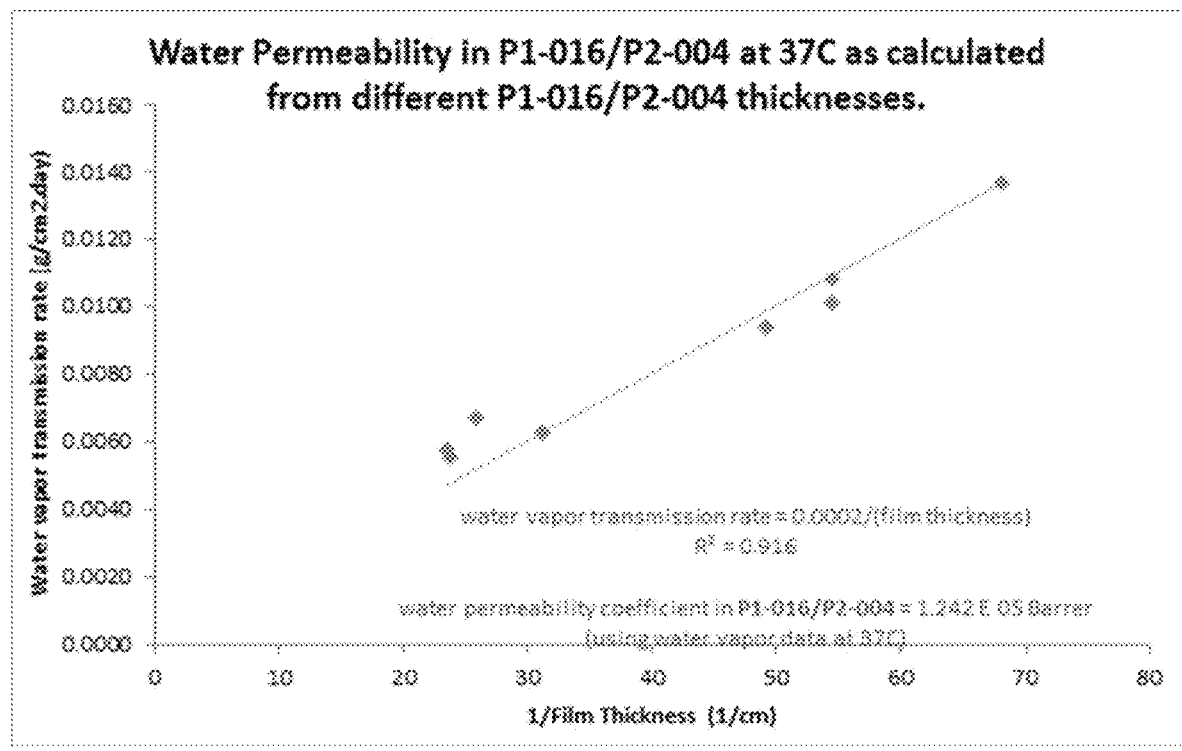
FIG. 14B is a chart illustrating the calculation of water vapor transmission rate based on P1-016/P2-004 (right side) at different thicknesses.

Water vapor transmission test was done following the guidelines of ASTM D1653 on Standard Test Methods for Water Vapor Transmission of Organic Coating Films, but under the condition of 10% RH at 37 C. The test is to compare the level of moisture occlusive barrier by measuring how water vapor can transport through the films a reflected in the water loss from the reservoir inside the cup under the set condition of 10% RH at 37 C. Results are also shown in FIG. 14.

Example 83: In-Vitro Water Vapor Transmission Rate

TABLE 75

| in-vitro water vapor transmission rate | | | | |
|---|---|---|---|---|
| | | 15° C., 50% RH | | |
| Sample Description | Thickness (microns) | Water Vapor Transmission Rate (g/m2.day) | Water Vapor Transmission Rate (g/m2.day) extrapolated to 50-micron film thickness | Comparative Ratio |
| Petrolatum (control) | 4,000 | 0.097 | 0.64 | 1x |

TABLE 75-continued in-vitro water vapor transmission rate

15° C., 50% RH

| Sample Description | Water Vapor Transmission Test Condition Thickness (microns) | Water Vapor Transmission Rate (g/m2.day) | Water Vapor Transmission Rate (g/m2.day) extrapolated to 50-micron film thickness | Comparative Ratio |
|---|---|---|---|---|
| P1-016/ P2-004 | 320 | 107 | 28.53 | 45x |

Example 84: In-Vitro Oxygen Transmission Rate

TABLE 76 in-vitro oxygen transmission rate

25 C., 0% RH, 760 mmHg, 100% O2 in carrier gas of 98% N2 and 2% H2

| Sample Description | Oxygen Transmission Test Condition Thickness (microns) | Oxygen Transmission Rate (cc/m2.day) | Oxygen Transmission Rate (L/m2.day) extrapolated to 50-micron film thickness | Comparative Ratio |
|---|---|---|---|---|
| Petrolatum (control) | 2,000 | 100 | 0.167 | 1x |
| P1-016/ P2-004 | 320 | 106,000 | 30.48 | 182.5x |

Figure 15:
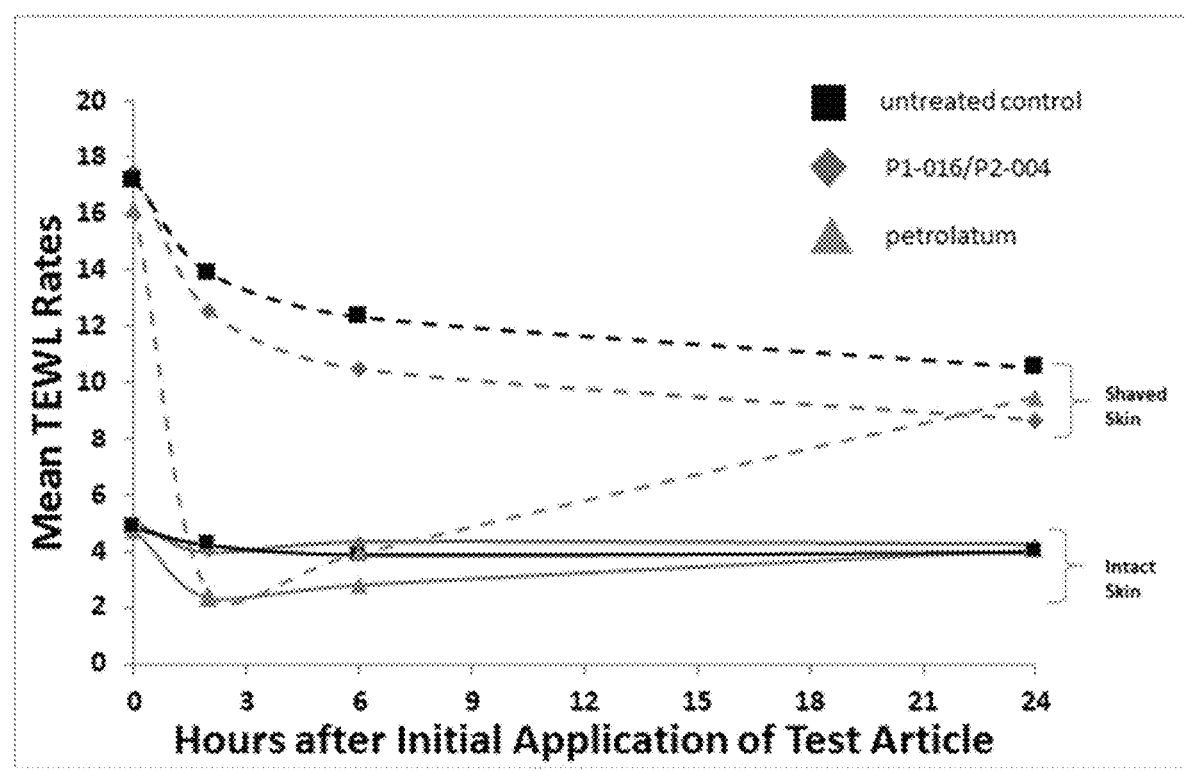
FIG. 15 is a chart illustrating clinical evaluation of in-vivo Transepidermal Water Loss (TEWL) of composition P1-016/P2-004 on skin after 2, 6, and 24 hours by Evaporimeter measurement.
Figure 16A:
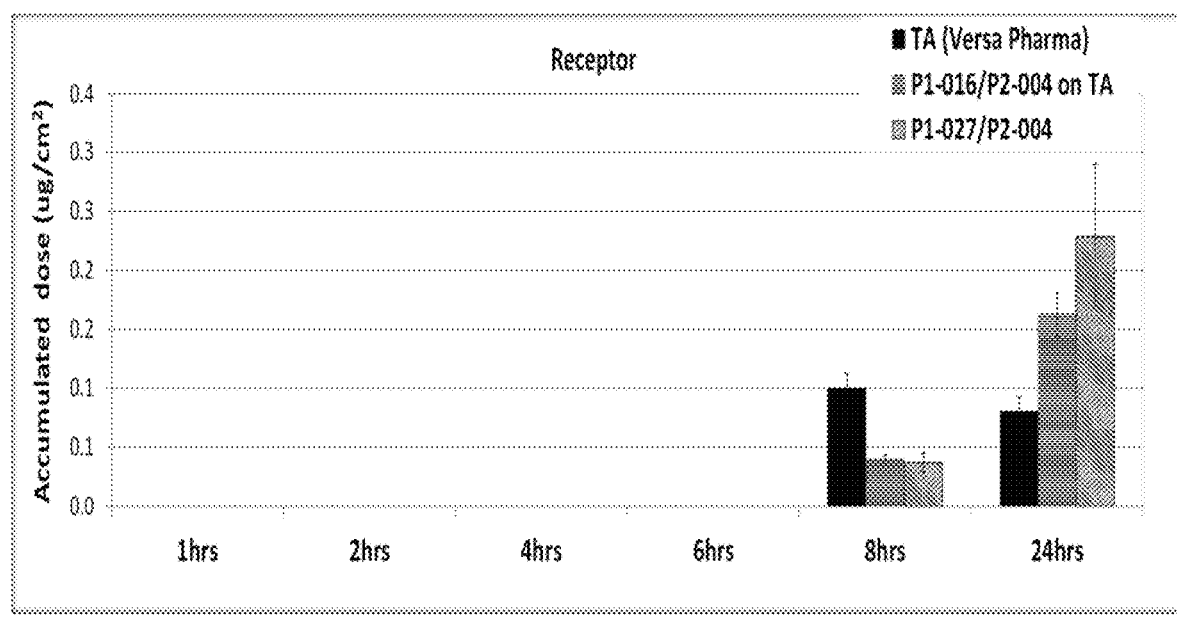
FIG. 16A is a chart illustrating accumulated transdermal delivered dose (from receptor fluid) of triamcinolone acetonide after 1, 2, 4, 6, 8, and 24 hours from the topical formulations comparing among 0.1% triamcinolone acetonide lotion (TA) (from Versa Pharma), P1-016/P2-004 layered on top of 0.1% TA, and P1-027/P2-004.
Figure 16B:
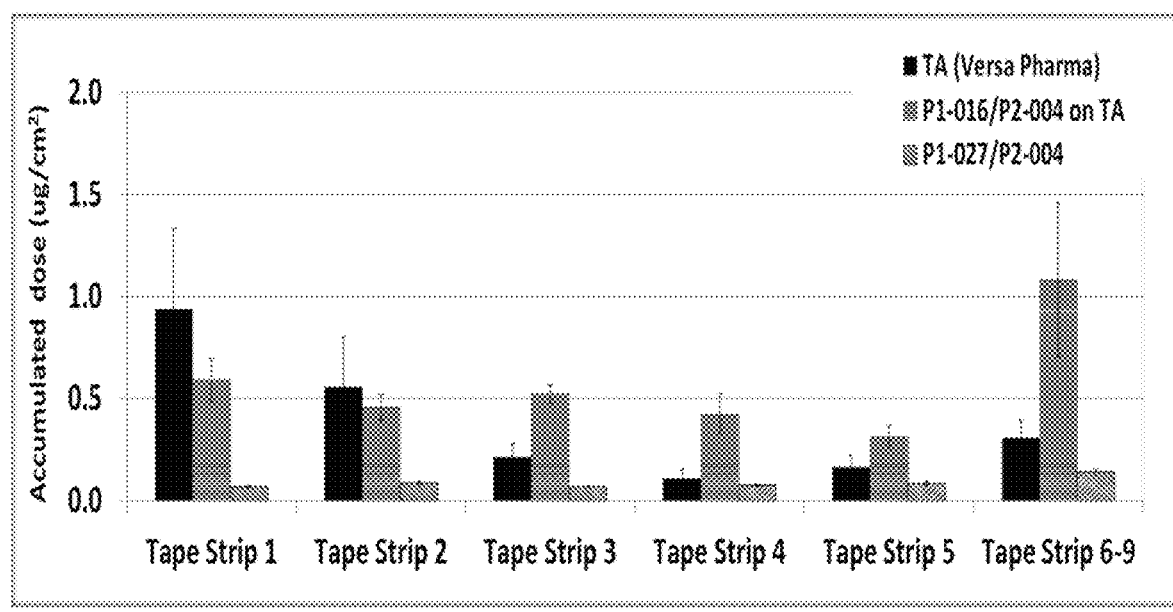
FIG. 16B is a chart illustrating accumulated delivered dose of triamcinolone acetonide in the tape strippings after 24 hours from the topical formulations comparing among 0.1% triamcinolone acetonide lotion (TA) (from Versa Pharma), P1-016/P2-004 layered on top of 0.1% TA, and P1-027/P2-004.
Figure 16C:
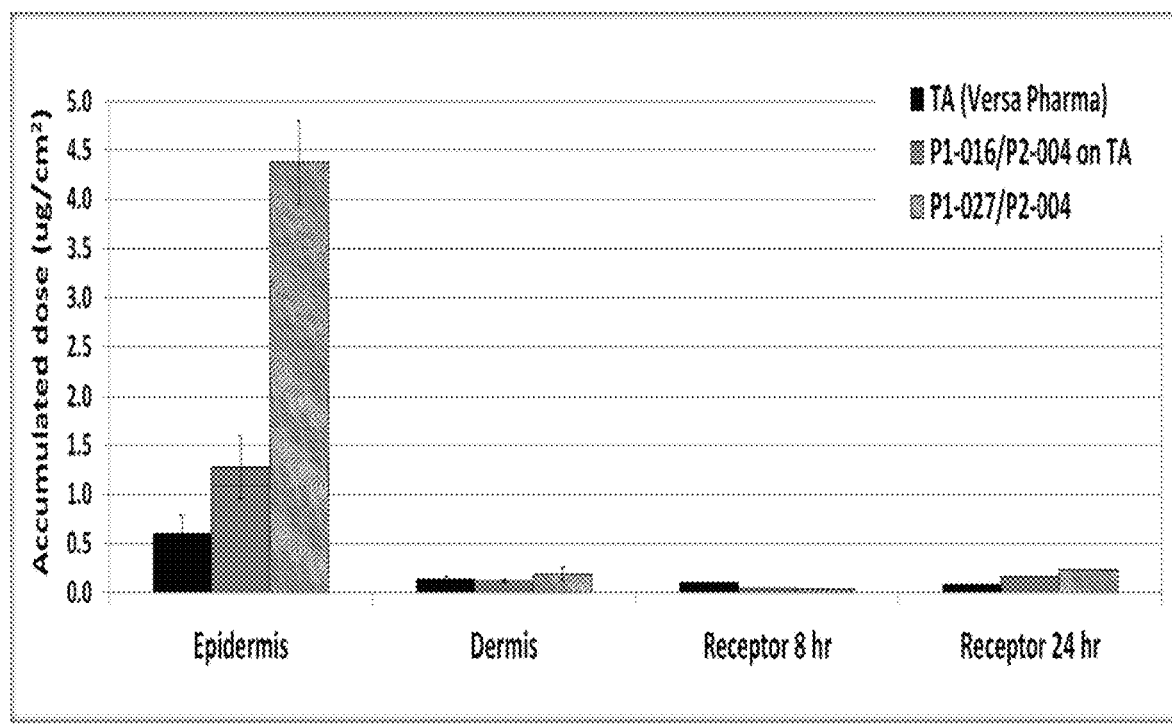
FIG. 16C is a chart illustrating accumulated delivered dose of triamcinolone acetonide in the epidermal, dermal, and receptor fluid after 24 hours from the topical formulations comparing among 0.1% triamcinolone acetonide lotion (TA) (from Versa Pharma), P1-016/P2-004 layered on top of 0.1% TA, and P1-027/P2-004.
Figure 18A:
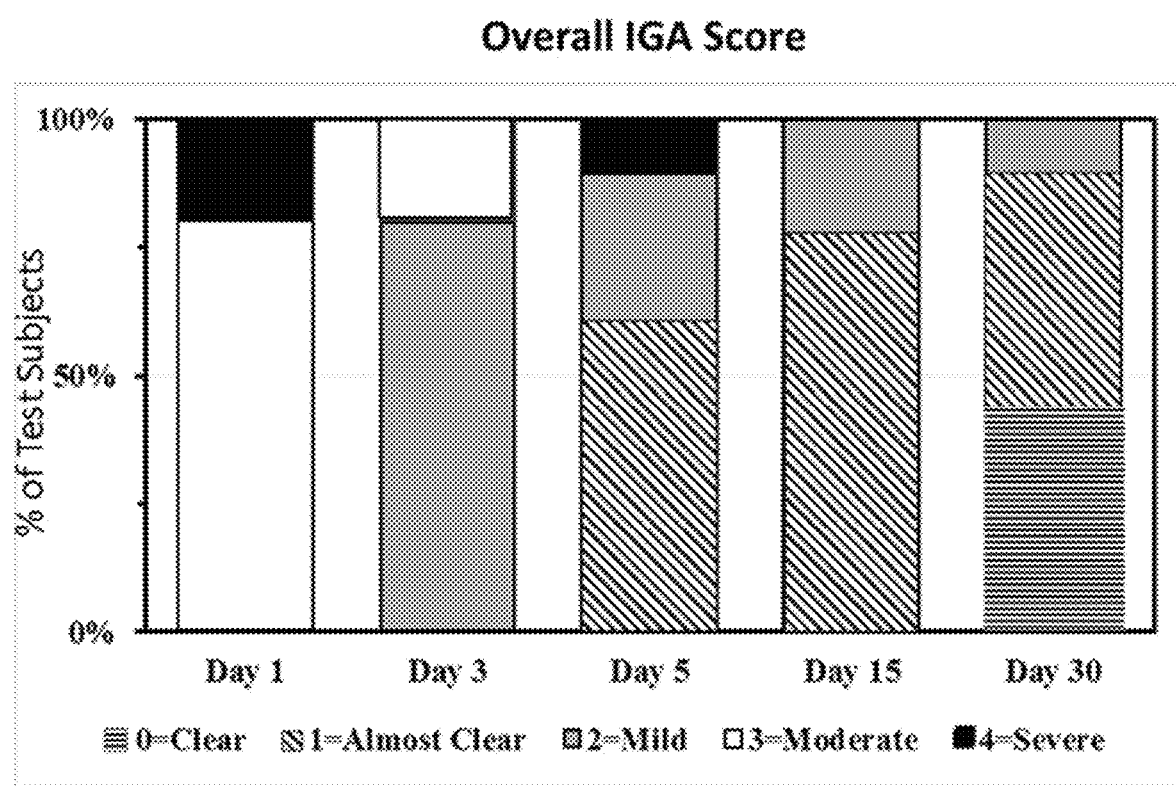
FIG. 18A is a chart illustrating clinical improvement in eczema severity by IGA after the application of composition P1-016/P2-004 over a period of 30 days.
Figure 18B:
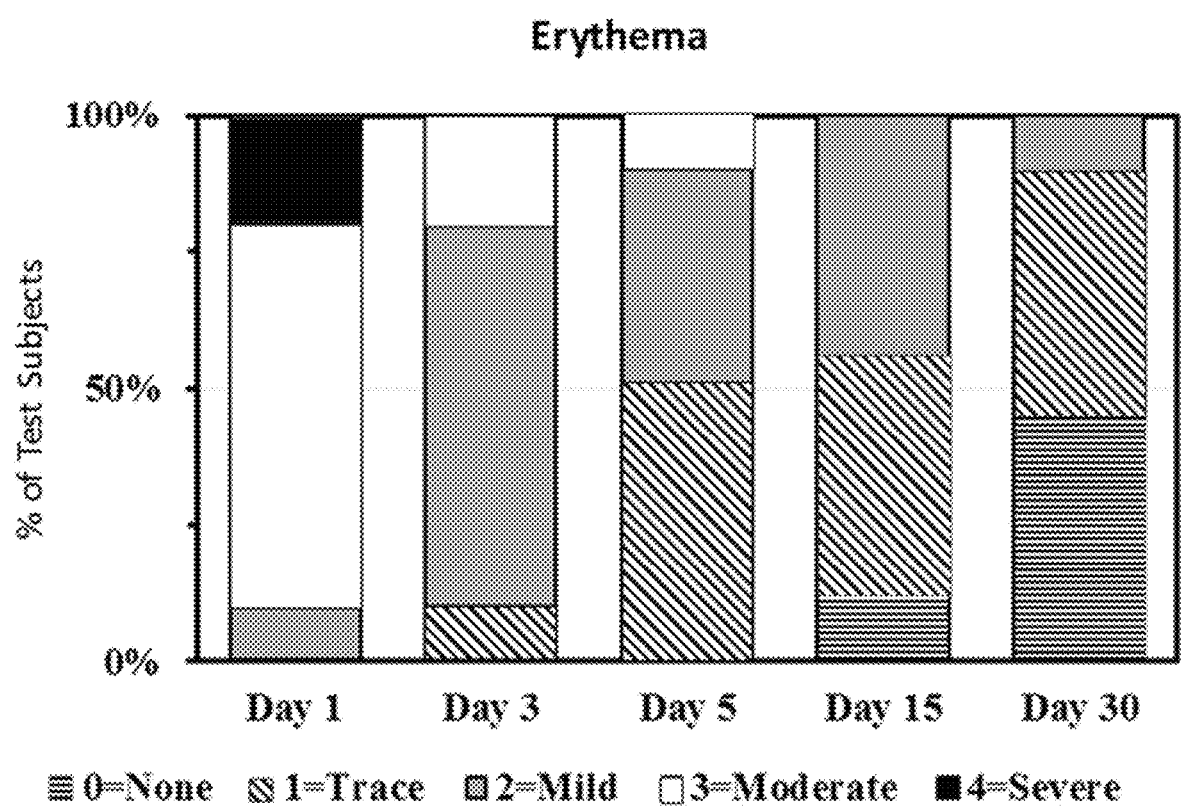
FIG. 18B is a chart illustrating improvement of clinical signs in erythema after the application of composition P1-016/P2-004 over a period of 30 days.
Figure 18C:
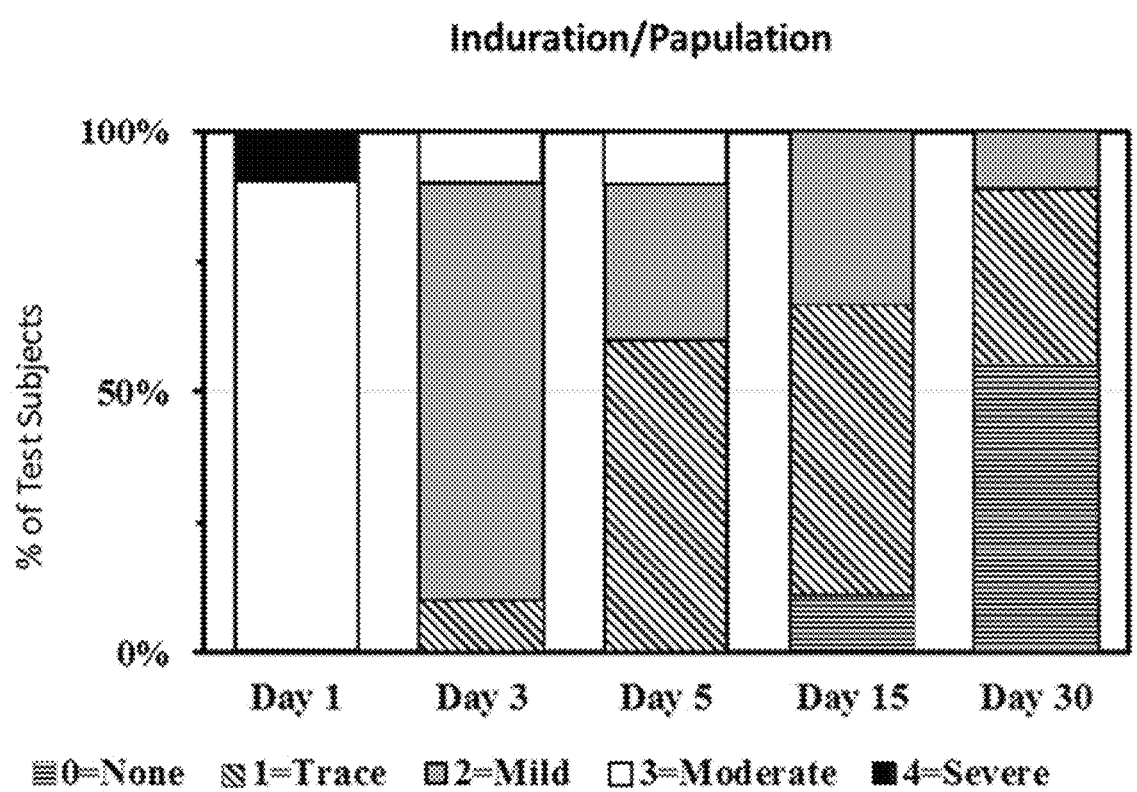
FIG. 18C is a chart illustrating improvement of clinical signs in papulation after the application of composition P1-016/P2-004 over a period of 30 days.
Figure 18D:
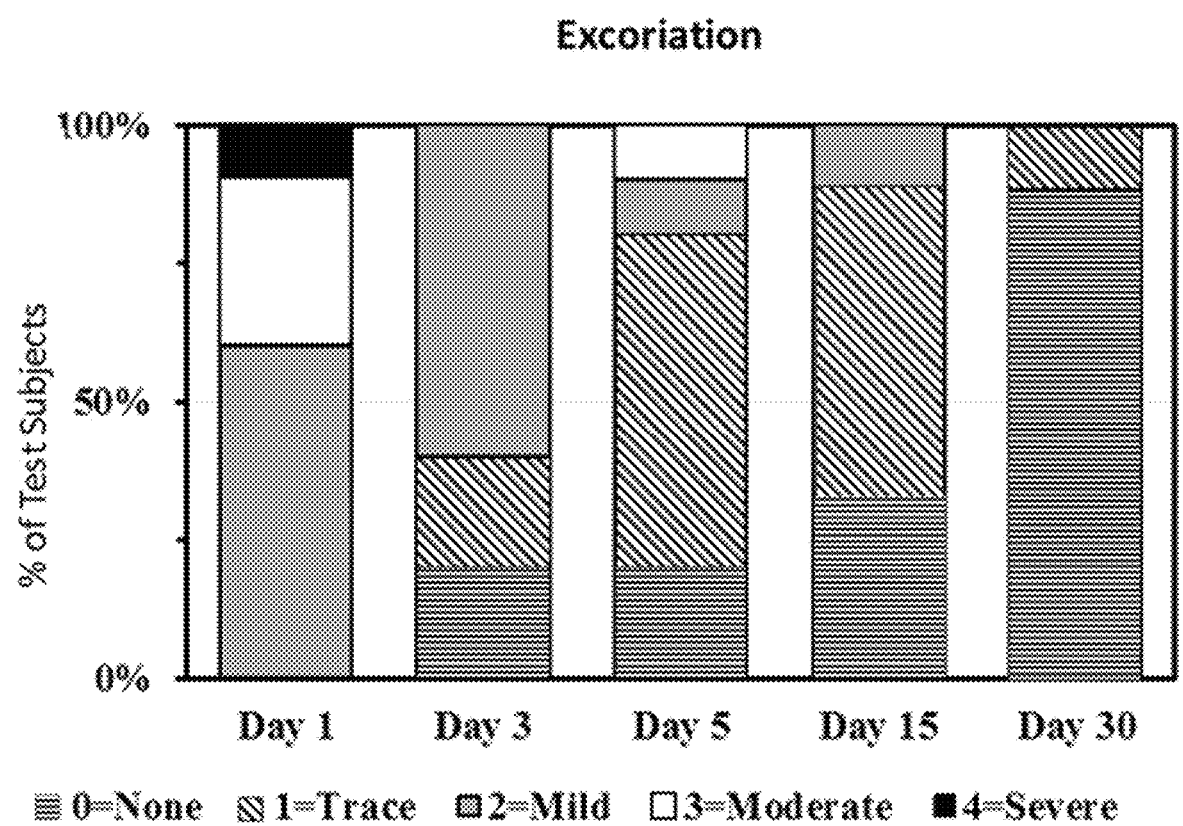
FIG. 18D is a chart illustrating improvement of clinical signs in excoriation after the application of composition P1-016/P2-004 over a period of 30 days.
Figure 18E:
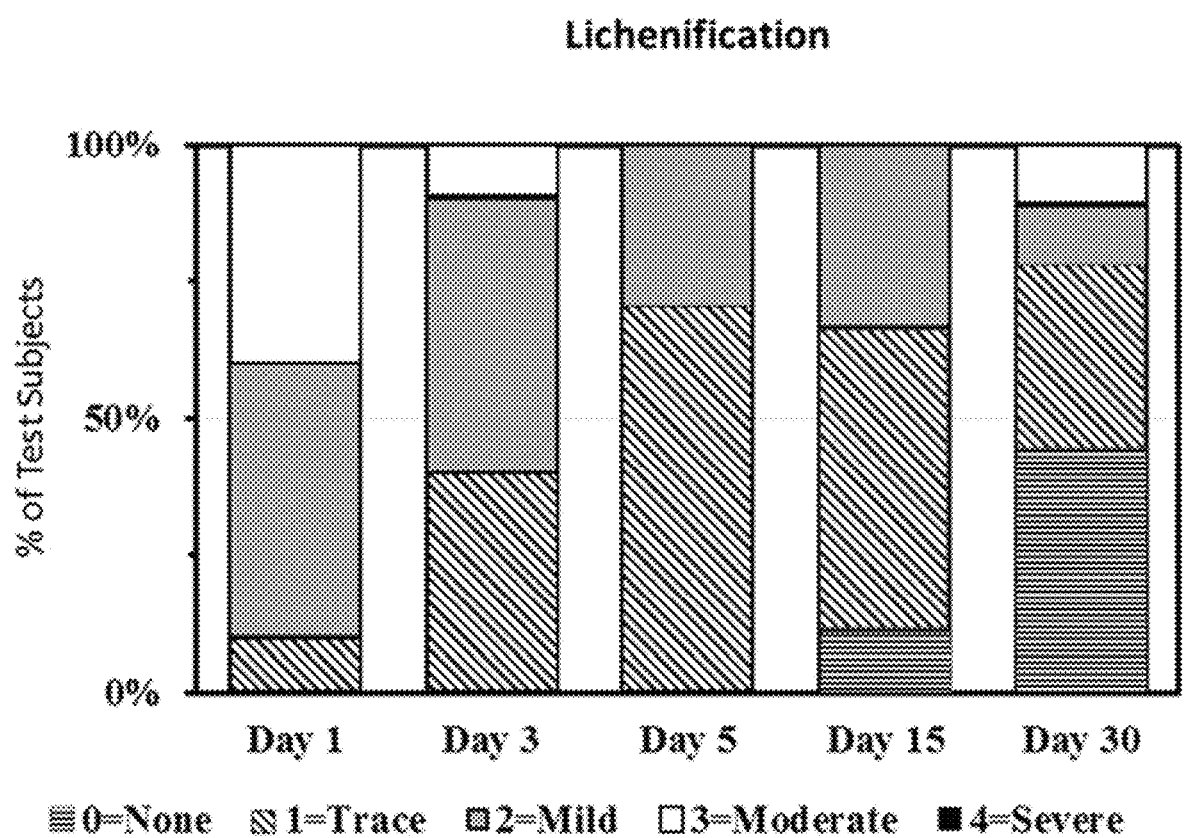
FIG. 18E is a chart illustrating improvement of clinical signs in lichenification after the application of composition P1-016/P2-004 over a period of 30 days.
Figure 18F:
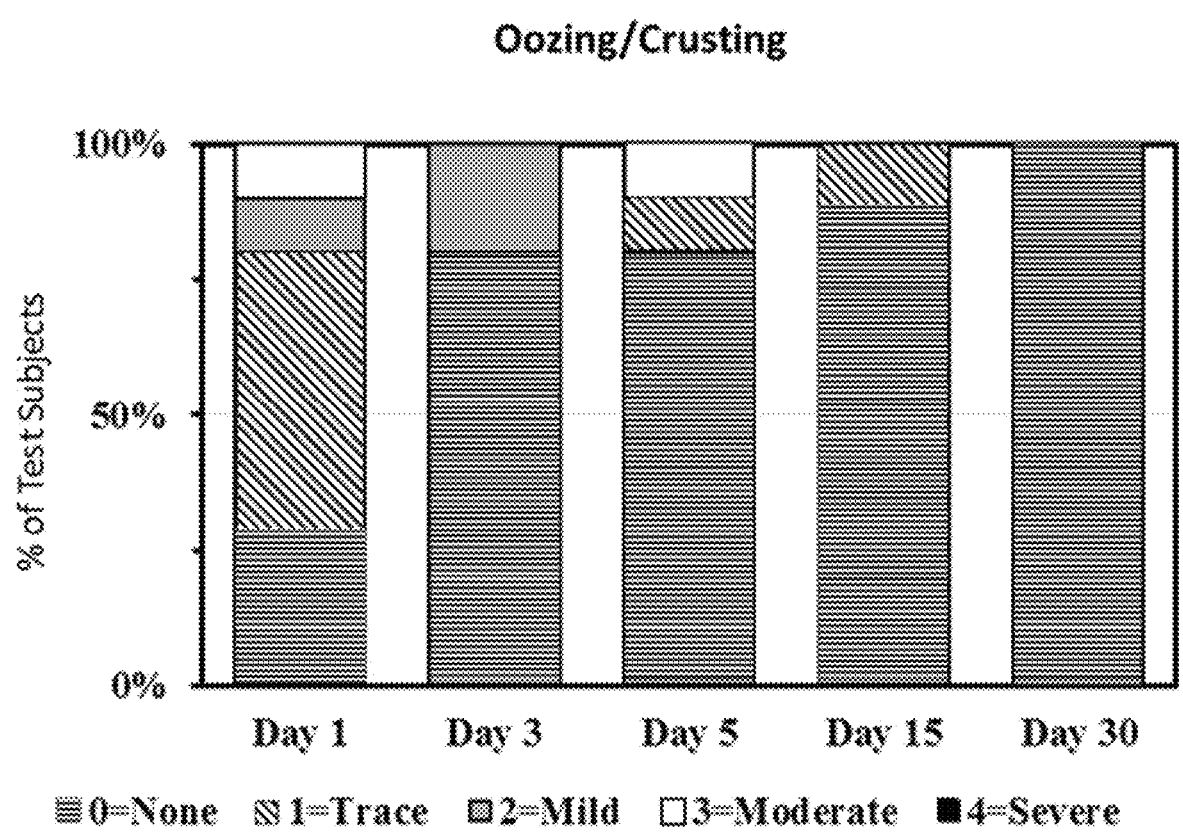
FIG. 18F is a chart illustrating improvement of clinical signs in oozing/crusting after the application of composition P1-016/P2-004 over a period of 30 days.
Figure 18G:
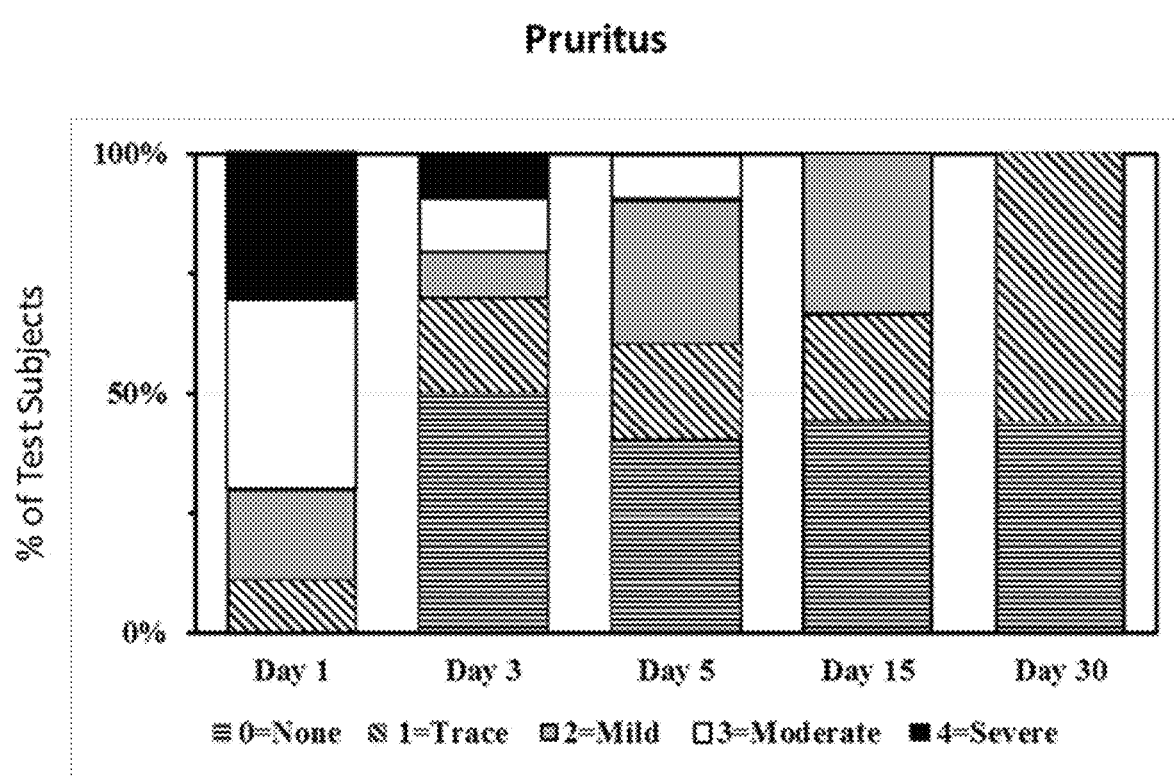
FIG. 18G is a chart illustrating improvement of clinical signs in pruritus after the application of composition P1-016/P2-004 over a period of 30 days.
Figure 18H:
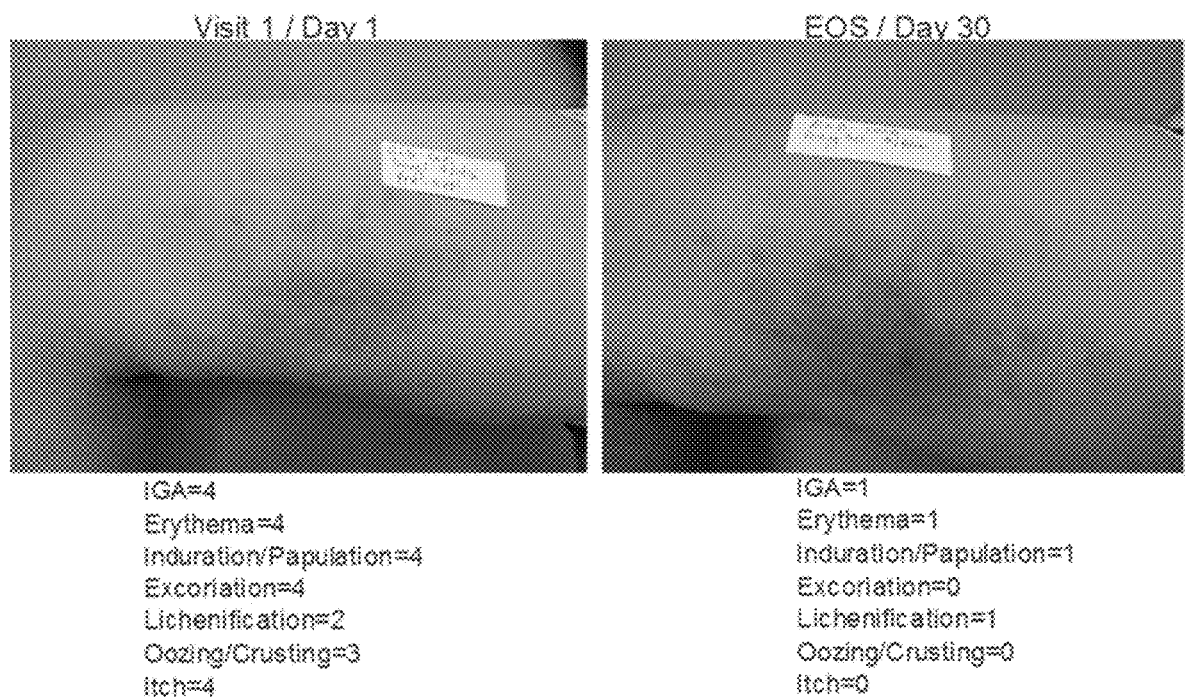
FIG. 18H is a chart illustrating improvement of several clinical signs of a subject's upper leg area after the application of composition P1-016/P2-004 over a period of 30 days.
Figure 18I:
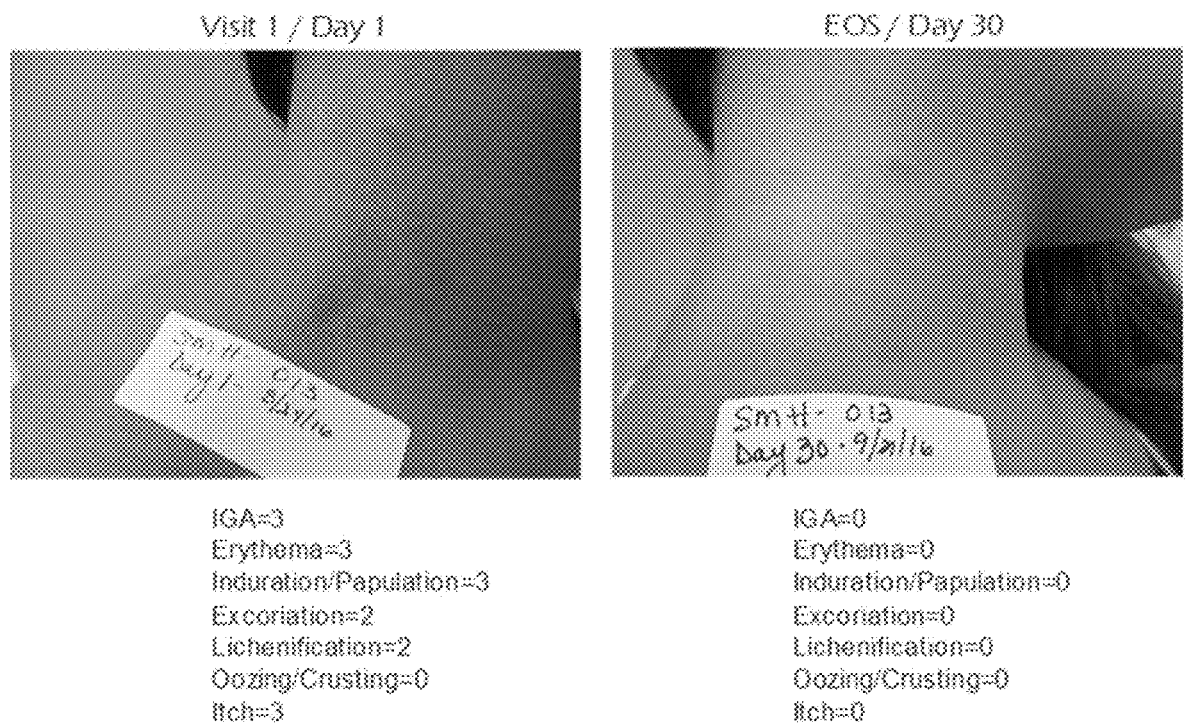
FIG. 18I is a chart illustrating improvement of several clinical signs of a subject's neck and shoulder area after the application of composition P1-016/P2-004 over a period of 30 days.

Example 85: Clinical Evaluation of In-Vivo Transepidermal Water Loss (TEWL) after 2, 6, and 24 Hours by Evaporimeter Measurement Clinical Study (S15-28) was based on 8 healthy volunteers with normal skin. The test composition was applied by technician on volar forearm site with an arm guard worn for 6 hours. P1-016/P2-024 was compared with petrolatum on two different test sites, normal skin versus damaged skin (dry shaved). Each test site covered the area of 4 cm×4 cm (~0.1% BSA). TEWL was measured by Evaporimeter before the application of test article and after 2, 6, and 24 hours. Prior to each TEWL measurement, subjects were equilibrated for 45 minutes. Initial TEWL reports for all intact skin sites averaged at 4.85 g/m²/hr, as opposed to for all dry shaved skin sites averaged at 16.92 g/m²/hr. Results are shown in FIG. 15.

Example 86: Ex-Vivo Dermal Drug Delivery Via Franz Diffusion Cell

The ex-vivo study via Franz diffusion cell on cadaver skin was to determine the rate and extent of skin permeation of a steroid drug "Triamcinolone Acetonide" from three different formulation combinations into and through intact human cadaver skin using a Franz diffusion cell system.

Test articles comprised of (1) commercial over-the-counter 0.1% Triamcinolone Acetonide lotion (TA) from Versa Pharma, (2) P1-016/P2-004 layered on top of TA from Versa Pharma, and (3) P1-027/P2-004. Each of them contained 0.1% Triamcinolone Acetonide. Concentrations of the Active were measured in the receptor chamber of the diffusion cell at varying time points. Upon conclusion of the diffusion study, the skin was sequentially tape-stripped and split into epidermal and dermal layers. Triamcinolone acetonide concentration in each of the binned tapestrips and epidermal and dermal tissues was extracted using an extraction solvent and was also analyzed with an Agilent G6120 HPLC system with a LC-MS detector.

Skin Preparation: Dermatomed intact human cadaver skin was purchased from the New York Fire Fighter's Tissue Bank (NYFFTB). The donor ID # from the tissue bank was: AV011816 #5. The donor information supplied by NYFFTB was: race: Caucasian, sex: male, age: 47, donor site: posterior leg. Upon receipt of the skin from the tissue banks, the skin was stored frozen at −20° C. until the morning of the experiment. Prior to use, the skin was removed from the freezer and allowed to fully thaw at room temperature. Only areas of the skin that were visually intact were used during the experiment.

Receptor fluid preparation: Based on the results of solubility studies, a receptor fluid of phosphate buffered saline (PBS) at pH 7.4 with 2 wt % hydroxypropyl-beta-cyclodextrin (HPBCD) was chosen. The solubility of triamcinolone acetonide in this receptor fluid was measured to be ~282 μg/ml—which is sufficient to maintain sink conditions in the receptor fluid throughout the course of the flux study. The preparation and degassing of the receptor fluid was was prepared at an appropriate pH and degassing was carried out by filtering the receptor fluid through a ZapCap CR 0.2 μm membrane while pulling vacuum.

Diffusion cell assembly: Custom made Franz diffusion cells (FDCs) with a receptor volume of 3.3 ml were used for the experiment. The available diffusional surface area of the skin for each cell is 0.55 cm². The receptor fluid was maintained at 32° C.±0.5° C. during the experiment using a stirring dry block heater and the fluid was continuously agitated with a stir bar. The steps for assembling the diffusion cells are outlined below:

The cadaver skin was removed from the freezer and allowed to defrost in a bio-safety hood for 30 minutes. The skin was thoroughly defrosted prior to opening the package.

The cadaver skin was removed from the package and placed on the bio-safety hood countertop with the stratum corneum side up. The skin was patted dry with a Kimwipe, then sprayed with fresh PBS and patted dry again. This process was repeated 3 more times to remove any residues present on the skin.

The receptor wells were then filled with the degassed receptor fluid. A Teflon coated stir bar was added to each receptor well.

The defrosted cadaver skin was examined and only areas with even thickness and no visible damage to the surface were used.

The skin was cut into 2 cm×2 cm squares.

The skin piece was centered on the donor cells, stratum corneum (SC) side up.

The skin was centered again and the edges flattened out. The donor and receptor wells were then aligned and clamped together with a pinch clamp.

Additional receptor fluid was added where necessary. Any air bubbles present were removed by tilting the cell, allowing air to escape along the sample port.

Diffusion cells were then placed in the stirring dry block heaters and allowed to rehydrate for 20 minutes from the receptor fluid. The block heaters were maintained at 32° C.±0.5° C. throughout the experiment with continuous stirring.

After 20 minutes, the surface of the skin was examined. If the skin was wet or showed signs of "sweating", the SC was considered compromised and discarded.

Membrane Integrity Check: Once the cells had been assembled and the skin allowed to hydrate for 20 minutes, the barrier integrity of each skin section was tested using a tritiated water test prior to the dosing of the formulation to the skin. The specific method for measuring skin barrier integrity is outlined as follows and detailed in Tioga Research SOP Lab.011.

- An aliquot of 150 µl of tritiated water (spiked with 25 µCi water/10 ml water) was added to each FDC donor well.
- After 5 minutes, the tritiated water from the donor wells was removed and the skin tapped dry using a Kimwipe.
- The receptor wells were agitated for an additional 1 hour after the tritiated donor fluid was removed.
- After 1 hour of agitation, a 300 µl aliquot sample was taken from each receptor well. The remaining receptor fluid was discarded and replaced with fresh PBS (membrane integrity study uses only PBS in receptor fluid)
- 600 µl of scintillation cocktail (Ultima Gold XR) was added to each sample aliquot.
- The tritium content of the receptor-well aliquot was then measured using a liquid scintillation counter (LSC).
- After LSC analysis was complete, results were analyzed. Any FDCs showing anomalously high water flux were discarded.
- The FDCs were then ranked according to ³H water flux. The FDCs were then distributed such that each formulation was assigned to FDCs with nearly equivalent average tritiated water flux values.
- Once the membrane integrity check study was complete, the entire receptor chamber volume was replaced with the receptor fluid.

Formulation application procedure: After the membrane integrity test was complete, and the cells appropriately sorted, the formulations were ready to be applied to the stratum corneum of the skin. The donor cell was first removed from the FDC—this step was necessary to allow for proper dosing of the formulations across the exposed surface area. Next, a plastic washer with a ~0.55 cm² opening was placed on top of the cadaver skin such that the opening aligned with the receptor chamber. A one-time dosing regimen was then used for this study. For dosing protocol #1, 5 µl of the TA was applied to the skin and spread across the skin surface using a glass rod (care was taken to ensure the formulation stayed within the confines of the plastic gasket). For dosing protocol #2, 5 µl of the TA was applied to the skin, then spread using a glass rod. 5 µl of formulation P1-016 was then applied on top of the TA and spread, followed lastly by 5 µl of formulation P2-004 being applied on top of both formulations and spread across the 0.55 cm² surface area. For dosing protocol #3, 5 µl of the formulation P1-027 was applied to the skin, and spread using a glass rod, followed by 5 µl of formulation P2-004 being applied on top of P1-027. In all dosing protocols, the weight of the FDC was measured before and after each dosing step to ascertain the amount of formulation that remained after spreading. The dose of the Active per cell and corresponding dosing protocol is shown.

TABLE 77

Triamcinolone dose per cell for each formulation combination. The triamcinolone dose assumes a specific gravity of 1.0 for the formulation and that 100% of the 5 µl dose remains on the skin after spreading the formulation.

| Dosing Protocol | Formulations | wt/wt % Triamcinolone Acetonide | Nominal formulation dose per cell | Triamcinolone Acetonide dose per cell |
|---|---|---|---|---|
| Protocol 1 | TA | 0.1 wt % (in TA) | 5 µl | 9.09 µg/cm² |
| Protocol 2 | TA + P1-016 + P2-004 | 0.1 wt % (in TA) | 5 µl + 5 µl + 5 µl | 9.09 µg/cm² |
| Protocol 3 | P1-027 + P2-004 | 0.1 wt % (in P1-027) | 5 µl + 5 µl | 9.09 µg/cm² |

Sampling of the Receptor Fluid: At 1, 2, 4, 6, 8 and 24 hours, a 300 µl sample aliquot was drawn from the receptor wells using a graduated Hamilton type injector syringe. Fresh receptor medium was added to replace the 300 µl sample aliquot. The samples were then filtered with a 0.2 µm GRP membrane filter plate.

Tape Stripping and Heat Splitting: At 24 hrs, the skin was tapped dry using a PBS/EtOH soaked KimWipe. Next, a piece of Mepitac tape was applied to the skin, allowed to sit for ten minutes, then removed. This Mepitac step was done a second time to ensure the formulation film is entirely removed. After the second Mepitac tape is removed, the skin was successively tape stripped. This involved applying a piece of cellophane tape to the skin with light pressure, then peeling the tape off and collecting the tape. With each tape strip, a layer of the stratum corneum is removed. Nine tape strips were taken per cell. The tape strippings were binned together in the following sections: Tape strip 1, tape strip 2, tape strip 3, tape strip 4, tape strip 5, and tapes strips 6-9.

After the skin was tape stripped, the epidermis of each piece of skin was then separated from the underlying dermal tissue using tweezers. The epidermal and dermal tissues were collected and separately placed in to 4 ml borosilicate glass vials.

After all the tape strips and skin pieces were collected, the Active was then extracted from the tape strips or skin. For the tape strips, this consisted of adding 4 ml of methanol to the vial, and agitating the vial for 24 hours at room temperature, after which a sample was collected. For the skin pieces, extraction was carried out by adding 2 ml of dimethyl sulfoxide (DMSO) to the vials containing the skin pieces, then incubating the vials at 40° C. for 24 hours with gentle agitation. After 24 hours, sample aliquots were taken and filtered with the 0.20 µm GRP membrane filter plate.

Analysis of Sample: Sample aliquots were analyzed with an Agilent G6120 HPLC system with a LC-MS detector. Samples were stored refrigerated at 4–8° C. prior to analysis to help prevent any unwanted degradation of triamcinolone acetonide.

Comparative delivered doses of triamcinolone for the different formulations for transdermal, stratum corneum (i.e. tapestrips) and epidermal and dermal delivery were reported. It appears that the addition of P1-016 and P2-004 on top of the TA (Versa Pharma formulation) increased the flux of the triamcinolone into the deeper tissue versus applying the TA from Versa Pharma formulation by itself. Dosing the skin with P1-027 and with P2-004 layered on top, led to the highest epidermal uptake. Results are shown in FIG. 16.

Example 87: Clinical Evaluation of In-Vivo Occlusion Benefit in Enhancing Steroid Potency Via Vasoconstriction Assay Clinical Study to evaluate in-vivo occlusion benefit in enhancing steroid potency was adapted from traditional vasoconstriction single point assay due to the presence of the film layer. The study was based on 37 healthy volunteers (23 females and 14 males) with normal skin. The test articles were applied by technician on volar forearm site at 6 test sites per subject in order to test three steroids of increasing potency, comparing the vasoconstriction outcome of the steroids with the presence versus the absence of P1-016/P2-024 film occlusion: Triamcinolone Acetonide (TA) lotion, 0.1%—Class 5, Fluticasone Propionate (FP) lotion, 0.05%—Class 5, Hydrocortisone (HC) 2.5% solution—Class 7. The vasoconstriction readouts were reported at 18 hours without wash-off at 16 hours.

Methodology: Single center, evaluator-blinded, randomized within subject, vehicle and reference controlled visual assessment.

Subjects: 36 planned, 37 enrolled, 37 analyzed (ITT population), 36 analyzed (PP population).

Diagnosis and main criteria for inclusion: Healthy male or female subjects 18-65 years of age with skin on the forearms that allowed vasoconstriction to be readily assessed and have a history or documentation of a positive skin-blanching response to topical corticosteroids.

Duration of Treatment: Single application for 16 (±1) hours of the following steroids, administered with and without occlusion using P1-016/P2-004 film:
1. Triamcinolone Acetonide lotion, 0.1% (Class 5)
2. Fluticasone Propionate lotion, 0.05%, (Class 5)
3. Hydrocortisone solution, 2.5% (Class 7)

Criteria for Evaluation:
Efficacy: Degree of skin blanching assessed visually on a four-point ordinal scale ranging from 0 (none) to 3 (marked blanching).
Safety: All adverse events (AEs) reported during the study were to be listed, documenting course, severity, and outcome.

Statistical Methods: Data was entered using double entry method using Excel. All statistical processing was performed using SAS®, version 9.4. Since this was a within-subject design, demographic characteristics such as gender and race were summarized as frequency distributions, while age was summarized as a mean and standard deviation.

Study Populations: All subjects enrolled in the study who were randomized and had at least one test article applied were included in the analysis of safety and efficacy. This was the intent-to-treat (ITT) population. Subjects were included in the per-protocol (PP) population efficacy analyses if they completed the study without significant protocol deviations.

Efficacy Analyses: The sums and means of the skin blanching scores for each test article, with or without occlusion, were calculated. All statistical tests were performed at a significance level of 5% (two-tailed). The primary analysis tests the null hypothesis that the visually assessed treatment blanching score means were equal to each other. Since this was a within-subject design, the visual skin blanching data was analyzed for mean differences among treatments using a randomized blocks analysis of variance (ANOVA) with subject as the blocking variable.

Within this analysis, pairwise comparisons of the mean visual assessment scores was performed using the Ryan-Einot-Gabriel-Welsch Multiple Range Test (REGWQ) which controls the experiment wise Type I error rate at 5% under the complete null hypothesis. The null hypothesis states that the treatment blanching score means are equal to each other.

Safety Analyses: All AEs reported during the study were to be listed, documenting course, severity, and relationship to test articles and outcome. All reported AEs were to be summarized by the number of subjects reporting AEs, system organ class (SOC), preferred term (PT), severity and relationship to test article by treatment, if possible.

Clinical Results

Summary of Results: Thirty-seven subjects were enrolled and treated in the study. All but one enrolled subject (Subject 01-106) completed the study (N=36). There were 24 (64.9%) females and 13 (35.1%) males enrolled into the study. Approximately 86% (32/37) of subjects were White, 8.1% (3/37) were Asian and the remaining two subjects were American Indian/Alaskan Native (1/37, 2.7%) and White and Black/African American (1/37, 2.7%). About two-thirds of subjects were not of Hispanic or Latino origin (25/37, 67.6%). The average age was 34.2 years with subject ages ranging from 19 to 62 years. All but one of the subjects (Subject 01-106) cleansed the test sites within the specified time windows, had the film removed, and had the vasoconstriction assessments performed within the specified time windows. Subject 01-106 was included in the ITT population but excluded from the PP population. This subject did not have the vasoconstriction assessments; thus, was not included in the vasoconstriction assessments summary.

Efficacy Results: Fluticasone propionate lotion, 0.05% (Class 5) with occlusion and triamcinolone acetonide 0.1% lotion (Class 5) with occlusion were not statistically significantly different from each other but were statistically significantly different from triamcinolone and fluticasone without occlusion, hydrocortisone (Class 7) with and without occlusion. Triamcinolone without occlusion was statistically significantly different from all other products as was hydrocortisone without occlusion. Hydrocortisone with occlusion and fluticasone without occlusion were not statistically significantly different from each other.

Safety Results: No subject experienced an AE and no subject discontinued the study due to safety reasons.

TABLE 78

Clinical evaluation of in-vivo occlusion benefit in enhancing steroid potency via

| TREATMENT | MEAN | GROUPING (REGWQ) |
|---|---|---|
| FP lotion, 0.05% (Class 5) with P1-016/P2-024 | 2.44 | A |
| TA lotion, 0.1% (Class 5) with P1-016/P2-024 | 2.28 | A |
| TA lotion, 0.1% (Class 5) without Occlusion | 1.56 | B |
| HC 2.5% solution (Class 7) with P1-016/P2-024 | 1.11 | C |
| FP lotion, 0.05% (Class 5) without Occlusion | 0.94 | C |
| HC 2.5% solution (Class 7) without Occlusion | 0.31 | D |

Vasoconstriction Assay

Clinical Conclusion

The vasoconstriction assessment results for the ITT and PP populations were essentially the same because one subject in the ITT population did not have the assessment. The Class 5 fluticasone and triamcinolone reference lotion products with occlusion from P1-016/P2-004 were not statistically different from each other and were statistically significantly different (more potent) than all the other reference products (with occlusion from P1-016/P2-004 or without occlusion). The Class 5 triamcinolone reference product without occlusion was statistically significantly different (more potent) than the Class 7 (hydrocortisone) reference product (with occlusion from P1-016/P2-004 or without occlusion) and the Class 5 reference product fluticasone without occlusion. This result is somewhat different that the published potency rating of fluticasone and triamcinolone lotion products which are identical (i.e. Class 5 potency). Such variability however is not unanticipated in VCA from time to time. The Class 7 hydrocortisone reference product with occlusion from P1-016/P2-004 and the Class 5 fluticasone reference product without occlusion were not statistically different from each other and statistically significantly different (more potent) than the Class 7 reference product without occlusion. The Class 7 hydrocortisone reference product was statistically significantly different (less potent) than all other reference products.

These results consistently demonstrated an increase in potency based upon occlusion from P1-016/P2-004 film for all three tested RLDs. With respect to P1-016/P2-004 film occluded hydrocortisone 2.5% test product, the equivalency to the fluticasone lotion RLD implies an increase to a Class 5 potency from Class 7 due to occlusion with the P1-016/P2-004 film. Similarly, both the Class 5 fluticasone lotion 0.05% and triamcinolone lotion 0.1% occluded reference products were more potent than their un-occluded counterpart. This implies an increase from Class 5 potency to at least Class 4 to Class 3 potency.

Example 88. Evaluation of Clinical Efficiency for Management of Conditions of Compromised Skin Barrier Function Evaluation of clinical efficiency for management of specific conditions of compromised skin barrier function by application of the compositions disclosed herein are described below.

Subjects:

A number of subjects suitable for statistical analysis (e.g., 24 to 64) with a specific condition of compromised skin barrier function (e.g., atopic dermatitis, psoriasis, eczema, ichthyosis vulgaris, xeroderma, rosacea) are selected for the study. For example, subjects with atopic dermatitis or eczema are selected based upon the widely accepted criteria proposed by Hanifin and Rajka, Diagnostic features of atopic dermatitis, *Acta. Derm Venereol Suppl* (Stockh) 1980; 92: 44-47. Subjects with ichthyosis vulgaris are selected based upon the widely accepted criteria described in Williams et al., The U.K. Working Party's Diagnostic Criteria for Atopic Dermatitis. III. Independent hospital validation, *Br J Dermatol* 1994; 131(3):406-416. Anyone with marks, scars, scratches or any skin condition are NOT excluded.

Subjects are evaluated for the severity of their specific skin condition following their arrival at the test site by a dermatologist and are followed up during their 2 week test period, preferably by the same dermatologist. Subjects are interviewed about the duration of the skin condition, other atopic disorders including asthma or allergic rhinitis, and other seasonal difference in the specific skin condition severity and their treatment history such as steroids, moisturizer or oral anti-histamines. Subject questionnaires are also given to subjects for self-evaluations on severity of conditions and life quality such as sleep pattern. Subjects may be further classified into mild, moderate and severe conditions.

Inclusion criteria:
1. Male and female at any age (e.g., for atopic dermatitis), between 6 and 70 years of age (e.g., for eczema, ichthyosis vulgaris), or between 18 and 70 years of age (e.g., for psoriasis);
2. Agrees to refrain from exercising and/or drinking hot or caffeinated beverages during the 2 hours prior to their appointment on the day of testing (this may affect the measurements);
3. Is willing and able to follow all study requirements and restrictions; and
4. Is able to read, understand, and sign the consent form.

Exclusion criteria:
1. Is pregnant, nursing or planning a pregnancy as determined by interview;
2. Is currently going through menopause (i.e., experiencing hot flashes);
3. Is a smoker;
4. Any other condition or factor the Investigator or his duly assigned representative believes may affect the skin response or the interpretation of the test results.

Subjects are NOT instructed to stop the use of all moisturizing products (soaps, lotions, sunscreens, insect repellent, etc.) during a 3 day pre-conditioning period prior to testing which is usually instructed to follow for regular hydration studies. However, subjects are instructed not to exercise or drink hot or caffeinated beverages within 2 hours prior to their day of testing visit as this may affect the measurements. Subjects are instructed not to apply ointment or oil prior to the examination.

Treatments and Procedures:

Two to six 5 cm by 5 cm test sites are outlined, using a standard template as guide, on the subject's skin including two or more areas with the specific skin condition ("skin lesion") and one or more areas with normal looking skin using a standard template.

Test products are applied over one to four identified skin lesions and over two to three normal looking skin area. At least one, and preferably two, identified skin lesions are left untreated as control. The test products are applied once a day throughout 2 weeks daily.

An aliquot of about 0.08-0.1 mL of the test composition is dispensed to a finger wearing finger cot and then directly applied to the test area. In case of a two-part test composition, the two compositions are applied to the same test area, with the first test composition (about 0.08 mL per 25 cm$^2$ area) applied to skin first and the second test composition (about 0.1 mL per 5 cm$^2$) dispensed with a new finger cot and applied over the same area treated with the first test composition by gliding motion to coat the treated area, but not by rubbing in, to minimize the mixing of the two test materials.

Product Removal Before Clinical Measurements:

All the test areas are cleansed to remove the test compositions before clinical measurements. The remover is shaken well to be homogeneous prior to use. The remover (1.5 mL per 25 cm$^2$) is poured onto a cotton round pad and then the wet pad is placed on the test area to remove the test compositions.

Clinical Measurements

Clinical measurements are conducted in one or more of the following aspects.

Disease severity
- SCORAD or OSCORAD (Objective Score of Atopic Dermatitis, European Task Force on Atopic Dermatitis, Severity scoring of atopic dermatitis: the SCORAD index, *Dermatology* 1993, 186:23-31) utilizes the rule of nines with six clinical features of atopic dermatitis disease intensity (eythema/darkening, edema/population, oozing/crust, excoriations, lichenification/prurigo/pruritus, and dryness), score ranges 0-103.
- PASI (Psoriasis Area and Severity Index, Fredriksson and Pettersson, Severe psoriasis—oral therapy with a new retinoid, *Dermatologica* 1978; 157:238-44) is based on the quantitative assessment of three typical signs of psoriatic lesions: erythema (redness), infiltration (thickness), and desquamation (scaling), on a scale of 0±4, combined with the skin surface area involved. The basis for the PASI score is the evaluation of four separate body areas: head, trunk, and upper and lower extremities. Scoring them separately for erythema, infiltration, and desquamation, after establishing the extent of skin surface involved, is time-consuming, and may take 10±15 min even for experienced personnel. An example scoring form is provided in FIG. 17. The PASI score is calculated as follows:

$$PASI=0.1(Eh+Ih+Dh)Ah+0.3(Et+It+Dt)At+0.2(Eu+Iu+Du)Au+0.4(El+Il+Dl)Al$$

where E=erythema; I=infiltration; D=desquamation; A=area; h=head; t=trunk; u=upper extremities; and l=lower extremities
- CRTT (Cutaneous Resonance Running Time, Song et al., Decreased cutaneous resonance running time in cured leprosy subjects, *Skin Pharmacol Physiol* 2009, 22:218-224 and Xin et al., Cutaneous resonance running time varies with age, body site and gender in a normal Chinese population, *Skin Res Technol* 2010, 16: 413-421) on psoriatic lesions by Revicometer RVM 600: A Courage-Khazaka Reviscometer RVM600 (CKelectronic GmbH, Koln, Germany) is used to measure the CRRTs in psoriatic lesions on the extensor of forearm and the contralateral uninvolved sites served as control. The measurement area with this probe is 8 mm. And the acoustical shockwave running distance is 2 mm with energy of 1.77 IJ. Measurements are begun in the 12 o'clock position, which is determined with the right forearms laid on the table as described previously. Measurements are then taken clockwise at every 1 h interval or at every 30°. These measurements provide the CRRTs in the directions of 0-6 o'clock, 1-7, 2-8, and so on. Readings in 1-7, 2-8, 3-9, 4-10, and 5-11 o'clock direction on the left forearm are compared with those in 5-11, 4-10, 3-9, 2-8, 1-7 o'clock direction, respectively, on the right forearm. All subjects rested at 20-24° C., at a relative humidity of about 50-55% for 30 min before measurements are taken.
- HECSI (Hand Eczema Severity Index, Held et al., The Hand Eczema Severity Index (HECSI): a scoring system for clinical assessment of hand eczema, *Contact Dermatitis* 2005, 152:302-307) is a clinical grading system of dermatitis of the hands used to assess product tolerability. HECSI assesses erythema, induration/papulation, vesicles and fissuring of dermatitis of the hands and the subject's perception of stinging, burning and itching.
- NESS (Nottingham Eczema Severity Score, Emerson et al., The Nottingham Eczema Severity Score: preliminary refinement of the Rajka and Langeland grading, *Br J Dermatol* 2000, 142: 288-297 and Hon et al., Validation of a self-administered questionnaire in Chinese in the assessment of eczema severity, Pediatr Dermatol 2003, 20:465-469) is used to assess clinical severity.
- Visual analogue scale (VAS), the Investigator's Global Assessment (IGA) and the Ichthyosis Vulgaris Area and Severity Index (EAST), Skin Dryness (Pruritus Severity Index Score) are also used to assess clinical severity, as described in Lee et al., Effectiveness of acupressure on pruritus and lichenification associated with atopic dermatitis: a pilot trial, *Acupunct Med.* 2012 March; 30(1):8-11.
- Quality of Life: DLQI for adults (Finlay and Khan, Dermatology Life Quality Index (DLQI)—a simple practical measure for routine clinical use, *Clin Exp Dermatol.* 1994 May; 19(3):210-6) and CDLQI for Children (Lewis-Jones and Finlay, The Children's Dermatology Life Quality Index (CDLQI): initial validation and practical use, *Br J Dermatol.* 1995 June; 132(6):942-9) questionnaires are used to measure how much a subject's disease had affected their lives over the last weeks. The response to each questionnaire was defined as 0-3 (0=not at all affected; 3=very much affected). DLQI was summarized under six subscales: "Symptoms and feelings;" "Leisure;" "Personal relationships;" "Treatment;" "Work and school;" and "Daily activities." The CDLQI was summarized under six subscales: "Symptoms and feelings;" "Leisure;" "Personal relationships;" "Treatment;" "School or holidays;" and "Sleep." Total quality of life (QOL) score was calculated by summing the score of each question. Total QOL score and the six subscales were expressed as a percentage of the respective maximum scores. The reliability and validity of DLQI were assured in the review by Basra et al., Dermatology Life Quality Index 1994-2007: a comprehensive review of validation data and clinical results, *Br J Dermatol.* 2008 November; 159(5):997-1035.
- Transepidermal Water Loss: TEWL and Skin Conductance or Capacitance (Yamamoto Y, Measurement and analysis of skin electrical impedance, *Acta Derm Venereol Suppl* (Stockh), 1994; 185:34-8)
- Stratum Corneum Integrity and Cohesion: Tape stripping is used as the quantification of the number of sequential D-squame tape stripping required to increase TEWL by 20 $g/m^2$ per hour
- Stratum Corneum Thickness: Stratum corneum thickness is calculated from low-frequency susceptance and high-frequency admittance by the corneometer as (square root of low-frequency susceptance)/(high-frequency $admittance^2$). Stratum corneum thickness is also visualized by conventional inmmunohistostaining. Stratum corneum thickness is also measured using light microscopy, such as Confocal Tandem Scanning Microscope (TSM), to measure the in depth (200 uM) measurement of the thickness of the different skin layers.
- Skin Biopsy/Immunohistochemical Staining: Immunoperoxidase staining of paraffin-embedded sections is performed using the ChemMate Peroxidase/DAB system (Dako Cytomation, Hamburg, Germany) to visualize the stratum corneum and epidermal structure, epidermal thickness and extracellular lamellar membranes.

Epidermis cell proliferation and hyperplasia can be examined using immunohistochemical staining of PCNA, Ki67, Ki-S3, or other proliferation markers.

Epidermal differentiation can be examined using immunohistochemical staining of Involucrin, Keratins CK 5, 6, 17, 1, 5, 10, 14 or other differentiation markers Laboratory Tests: Peripheral blood EOS count (number 100 per ml; normal 40-440), serum LDH (IU $l^{-1}$; normal 119-229), total serum IgE (IU $ml^{-1}$; normal 0.0-400.0), and allergen-specific IgE (SRL Inc., Tokyo, Japan) are measured. Allergen-specific IgE were estimated by fluoroenzyme immunoassays for house dust, mite allergen, grass pollen (Tancy), cedar pollen, fungal allergen (Candida), animal dander, and foods. Concerning to the sensitivity for detection of specific IgE, 100 lumicount and values greater than or equal to 100 lumicount are considered positive (+).

In addition, serum cathelicidins (LL-37) concentration is measured using enzyme immunoassay (Bachem, San Carlos, Calif., USA, as described in Leung et al., Circulating LL-37 is a biomarker for eczema severity in children, *J Eur Acad Dermatol Venereol.* 2012; 26:518-522). Samples are diluted 90-fold prior to measurement. The sensitivity of this assay was 1 ng/mL.

Statistical Analysis: Simple regression analyses are also used to identify significant associations of stratum corneum hydration, thickness, or TEWL to SCORAD or PASI. Data with P-values less than 0.05 are evaluated as significant and P-values less than 0.005 as highly significant. Wilcoxon rank sum test and simple regression analyses are performed to assess the association or correlation between different biological markers including IgE, LDH, EOS, and the SCORAD or PASI.

TABLE 79

Clinical Endpoints and Biomarkers

| DERMATOSIS TYPE | CLINICAL ENDPOINT | BIOMARKER |
|---|---|---|
| Atopic Dermatitis | Cutaneous Barrier Function, Homeostasis and Inflammation: SCORAD/OSCORAD DLQI/CDLQI TEWL/Conductance/Capacitance Stratum Corneum Integrity and Cohesion: Tape Stripping | Skin Biopsy/Immunohisto-chemical staining: Epidermis cell proliferation and hyperplasia Epidermal differentiation Lamellar bodies quantity in Stratum Corneum (SC) and Stratum Granulosum (SG) Epidermal Thickness: Light microscopy or Corneometer Cellular Structure: Optical coherence tomography (OCT)- Arrangement of the collagen fibres SC and epidermal lipid: Lipid content Ceramide quantity: mRNA levels of the epidermal glucosylceramide transport protein (ATP-binding cassette A12) SC and epidermal protein Filaggrin (FLG) Aquaporin (AQP3) Protease activated receptor-2 (PAR-2) Caveolin-1 (cav-1) Skin Surface pH SC Integrity and Cohesion: Skin Biopsy Serine proteases (in situ zymography) Desmoglein (Western Blot) Corneodesmosome (Western Blot) B-glucocerebroside activity (Western Blot) Lipid processing (SEM) Inflammation (Blood samples): Immunoglobulin E (IgE) Mast cell hyperactivity Dendritic cell signalling |
| Psoriasis | Cutaneous Barrier Function and Homeostasis: PASI TEWL/Conductance/Capacitance Self-reported Questionnaires CRTT on psoriatic lesions by Revicometer RVM 600 Stratum Corneum Integrity and Cohesion: Tape Stripping | Same as Atopic Dermatitis, but does not include: SC and epidermal protein: Filaggrin (FLG) Aquaporin (AQP3) Protease activated receptor-2 (PAR-2) Caveolin-1 (cav-1) |

TABLE 79-continued

Clinical Endpoints and Biomarkers

| DERMATOSIS TYPE | CLINICAL ENDPOINT | BIOMARKER |
|---|---|---|
| Eczema | Cutaneous Barrier Function and Homeostasis: SCORAD/OSCORAD TEWL/Conductance/Capacitance HECSI NESS | Same as Atopic Dermatitis, and further includes: Expression of antimicrobial peptides Serum cathelicidin immunoassay |
| Ichthyosis Vulgaris | Cutaneous Barrier Function and Homeostasis: Pruritus Severity Index Score TEWL/Conductance/Capacitance Stratum Corneum Integrity and Cohesion: Tape Stripping | Same as Atopic Dermatitis, but does not include: SC and epidermal protein: Filaggrin (FLG) Aquaporin (AQP3) Protease activated receptor-2 (PAR-2) Caveolin-1 (cav-1) |
| Xeroderma | Cutaneous Barrier Function and Homeostasis: Pruritus Severity Index Score TEWL/Conductance/Capacitance Stratum Corneum Integrity and Cohesion: Tape Stripping | Same as Atopic Dermatitis, but does not include: SC and epidermal protein: Filaggrin (FLG) Aquaporin (AQP3) Protease activated receptor-2 (PAR-2) Caveolin-1 (cav-1) |

Example 89. Evaluation of Clinical Efficiency for Adult with Eczema

Evaluation of clinical efficiency for management of eczema by application of the compositions disclosed herein are described below. The study was a single center, open label study.

Subjects:

10 subjects (7 females and 3 males) aged 18 years and older with mild to severe eczema including atopic dermatitis (Investigator's Global Assessment [IGA] Disease Severity of Grade 2 to 4)

Subjects are evaluated for the severity of their specific skin condition following their arrival at the test site by a dermatologist and participate in the study for five (5) days followed by an open label use period of up to a total of 30 days. Subjects are interviewed about the duration of the skin condition.

Inclusion criteria:
1. Subject is a male or non-pregnant female, aged 18 years of age or older at the time of consent.
2. Women of of childbearing potential (WOCBP) must have a negative urine pregnancy test (UPT) at Visit 1/Baseline to qualify; female subjects who are post-menopausal,[1] unable to conceive due to previous obstetric surgery or are using an effective method of contraception.
3. Subject is willing and able to give written informed consent.
4. Subject has the clinical diagnosis of "Eczema" which shall include Atopic Dermatitis (AD) based upon the criteria of Hanifin and Rajka or other forms of eczematous dermatitis in the opinion of the investigator (e.g. nummular eczema etc.).
5. Subject has a clinical diagnosis of stable [within three (3) months] mild to severe (Grade 2 to 5) Eczema as determined by the Investigator's Global Assessment (IGA) within the designated Treatment Area, which includes a minimum of 0.5% BSA of active disease.
6. Subject is willing and able to apply the test articles(s) as directed, comply with study instructions, and commit to all follow-up visits for the duration of the study.
7. In the investigator's opinion, subject is in good general health and is free of any disease state or physical condition that exposes the subject to an unacceptable risk by study participation or impairs the evaluation of the subject or test article by participating in the study.

Exclusion criteria:
1. Subject is pregnant, lactating, or is planning to become pregnant during the study.
2. In the opinion of the investigator, the subject has skin pathology or condition that could interfere with the evaluation of the test products or requires the use of interfering topical or systemic therapy during the study.
3. Subject has used any of the following topical preparations on the Treatment Area:
    a. Topical (including OTC products) treatments including, but not limited to, corticosteroids, immunomodulators (tacrolimus, pimecrolimus, etc.), tar, calcipotriene or other vitamin D preparations, antihistamines (doxepin, diphenhydramine, etc.), or antibiotics within one (1) week of Visit 1/Baseline. Note: Stable (>30 days) doses of oral or intranasal antihistamines for treatment of allergic rhinitis, inhaled or intranasal corticosteroids for treatment of bronchial asthma, or antibiotics for treatment of acne will be allowed, but must be documented.
    b. Retinoids (including tazarotene, adapalene, and tretinoin) within four (4) weeks of Visit 1/Baseline.
    c. Light treatments (PUVA, UVB, excimer laser, etc.), microdermabrasion, or chemical peels within four (4) weeks of Visit 1/Baseline.
    d. Other topical therapy, which may materially affect the subject's atopic dermatitis in the opinion of the investigator.
4. Subject has used any of the following systemic medications:
    a. Corticosteroids (including intramuscular and intralesional injections) within one (1) week of Visit 1/Baseline.
    b. Immunomodulators (including leukotriene) or anti-metabolites within one (1) weeks of Visit 1/Baseline.
    c. Oral or topical Antibiotics (OTC or prescription) within one (1) week, unless on a stable dose for acne (more than 3 months of use), of Visit 1/Baseline.

d. Other systemic therapy, which may materially affect the subject's atopic dermatitis in the opinion of the investigator.

5. Subject is currently using or has used an investigational drug or investigational device treatment within 30 days of Visit 1/Baseline.
6. Subject is currently enrolled in an investigational study.
7. Subject has a history of sensitivity to any of the ingredients in the test articles (see Section 5.1 in the protocol).
8. Subject is known to be noncompliant or is unlikely to comply with the requirements of the study protocol (e.g., due to alcoholism, drug dependency, mental incapacity) in the opinion of the investigator.
9. Subject currently has a skin infection.

Treatments and Procedures:

The study will consist of three (3) clinic visits over five (5) days and two follow-up visits on Day 15 (visit 4) and Day 30 (visit 5).

Visit 1 (Screening/Baseline): Day 1. Subjects can be screened for the study up to 30 days before Visit 1. During screening, the study requirements will be reviewed, written informed consent obtained, and eligibility confirmed. If applicable, the washout from prohibited medications or treatments will be determined and implemented. These procedures may be performed as a separate screening visit prior to the Baseline Visit, as/if required.

Demographics, inclusion/exclusion criteria, medical/dermatological history, and concomitant medications and therapies will be reviewed to determine subject eligibility. A brief dermatologic exam and UPT (if applicable) will be performed. Clinical evaluations (IGA and Clinical Signs of Eczema) and itch assessment will be performed prior to test article application. The Treatment Area will be defined as a discrete contiguous anatomic unit of up to 3% BSA (e.g., an arm, leg, abdomen, etc.), which must include a minimum of 0.5% BSA of active disease. The percent BSA to be treated and the location of the Eczema affected skin will be documented. The percent BSA will be estimated based on the assumption that 1% BSA is equivalent to the area of the subject's hand with fingers held together.

The test article will be applied to the Treatment Area using the following instructions:

1. Wash with an antimicrobial soap and completely dry the affected area.
2. Use a clean and dry fingertip to dispense and apply a thin layer of P1-016 formulation to the Treatment Area. Ensure the product is in a uniform layer with no thick areas. Approximately a quarter-sized amount of P1-016 should cover 1% BSA.
3. Clean your fingertip.
4. Use a fingertip to dispense and apply a thin layer of P2-004 formulation. Gently spread the P2-004, completely covering the P1-016 area. Do not rub into the P1-016 layer; simply glide until it is evenly sitting on top. 1-1.5× amount of P2-004 can be used compared to P1-016. Approximately a quarter-sized amount of P2-004 should cover 1% BSA.
5. Do not touch or move for at least 2 minutes while film sets.

Photographs may be taken to document the baseline Treatment Area. The subject will be asked about his/her impression of the product and its ease of use; responses will be documented in a subject questionnaire. Any AEs will be documented.

Use of topical Eczema care of affected skin areas outside of the Treatment area is allowed during the study period. Systemic Eczema treatments or other topical treatments of any kind in the Treatment Area are prohibited.

Test article and a diary will be provided to the subject prior to discharge from the clinic. These materials will be returned by the subject to the site at the next clinic visit. The subject will be instructed to apply the film each day, as needed, until the next clinic visit; if the film remains intact throughout the day no further application is needed until the film starts to peel off or break down. As required, the subject may apply the film up to twice daily as designated by the investigator to maintain an intact film on the Treatment Area. In most cases, it is anticipated that the subject will be applying the film every 1 to 3 days, depending on how well it wears. Prior to each application of the film, the old film will be removed as directed per protocol. At the request of the investigator, as an option, during any clinic visit the film may be removed and reapplied by the subject under supervision rather than at home. In all cases, during the study, the subject will document apply applications of the film in the subject diary provided. The subject will be scheduled for their next return visit and discharged from the clinic.

Visit 2 (Follow-Up): Day 3±1 day. Subjects will return to the clinic for follow-up and queried for any changes in health status. Concomitant medications will be reviewed. Clinical evaluations (IGA and Clinical Signs of Eczema) and P1-016/P2-004 Film durability and itch assessments will be performed. Photographs may be taken to document the durability of the treatment. Any AEs will be documented.

Test article and a diary will be reviewed and, as required, new test article and/or a new diary will be provided by the subject prior to discharge from the clinic. These materials will be returned by the subject to the site at the next clinic visit. The subject will be instructed to apply the film each day, as needed, until the next clinic visit; if the film remains intact throughout the day no further application is needed until the film starts to peel off or break down. As required, the subject may apply the film up to twice daily as designated by the investigator to maintain an intact film on the Treatment Area. In most cases, it is anticipated that the subject will be applying the film every 1 to 3 days, depending on how well it wears. Prior to each application of the film, the old film will be removed as directed per protocol. At the request of the investigator, as an option, during any clinic visit the film may be removed and reapplied by the subject under supervision rather than at home. In all cases, during the study, the subject will document apply applications of the film in the subject diary provided. The subject will be scheduled for their next return visit and discharged from the clinic.

Visit 3 (End of Film Durability Assessment): Day 5±1 day. Subjects will return to the clinic for follow-up and queried for any changes in health status. Concomitant medications will be reviewed. Clinical evaluations (IGA and Clinical Signs of Eczema) and P1-016/P2-004 Film durability and itch assessments will be performed. Photographs may be taken to document the durability of the treatment. The subject will be instructed on how to remove the film and removal will occur in the clinic under supervision from the study staff. The ease of film removal and any related irritation of the skin will be noted. The subject will be asked about his/her impression of the product and its ease of use; responses will be documented in a subject questionnaire. Any AEs will be documented.

Test article and a diary will be reviewed and, as required, new test article and/or a new diary will be provided by the subject prior to discharge from the clinic. These materials will be returned by the subject to the site at the next clinic visit. The subject will be instructed to apply the film each day, as needed, until the next clinic visit; if the film remains intact throughout the day no further application is needed until the film starts to peel off or break down. As required, the subject may apply the film up to twice daily as designated by the investigator to maintain an intact film on the Treatment Area. In most cases, it is anticipated that the subject will be applying the film every 1 to 3 days, depending on how well it wears. Prior to each application of the film, the old film will be removed as directed per protocol. At the request of the investigator, as an option, during any clinic visit the film may be removed and reapplied by the subject under supervision rather than at home. In all cases, during the study, the subject will document apply applications of the film in the subject diary provided. The subject will be scheduled for their next return visit and discharged from the clinic.

Visits 4 (Follow-Up): Day 15±2 days. Subjects will return to the clinic for follow-up and queried for any changes in health status. Concomitant medications will be reviewed. Clinical evaluations (IGA and Clinical Signs of Eczema) and P1-016/P2-004 Film durability and itch assessments will be performed. Photographs may be taken to document the durability of the treatment. Any AEs will be documented.

Test article and a diary will be reviewed and, as required, new test article and/or a new diary will be provided by the subject prior to discharge from the clinic. These materials will be returned by the subject to the site at the next clinic visit. The subject will be instructed to apply the film each day, as needed, until the next clinic visit; if the film remains intact throughout the day no further application is needed until the film starts to peel off or break down. As required, the subject may apply the film up to twice daily as designated by the investigator to maintain an intact film on the Treatment Area. In most cases, it is anticipated that the subject will be applying the film every 1 to 3 days, depending on how well it wears. Prior to each application of the film, the old film will be removed as directed per protocol. At the request of the investigator, as an option, during any clinic visit the film may be removed and reapplied by the subject under supervision rather than at home. In all cases, during the study, the subject will document apply applications of the film in the subject diary provided. The subject will be scheduled for their next return visit and discharged from the clinic.

Visits 5 (End of Study, or Early Termination): Day 30±3 days. Subjects will return to the clinic for follow-up and queried for any changes in health status. Concomitant medications will be reviewed. A UPT (if applicable) will be performed. Clinical evaluations (IGA and Clinical Signs of Eczema) and P1-016/P2-004 Film durability and itch assessments will be performed. Photographs may be taken to document the durability of the treatment. The film will be removed. Test article and diary will be collected. Any AEs will be documented. The subject will be discharged from the study.

Two to six 5 cm by 5 cm test sites are outlined, using a standard template as guide, on the subject's skin including two or more areas with the specific skin condition ("skin lesion") and one or more areas with normal looking skin using a standard template.

Test products are applied over one to four identified skin lesions and over two to three normal looking skin area. At least one, and preferably two, identified skin lesions are left untreated as control. The test products are applied once a day throughout 2 weeks daily.

An aliquot of about 0.08-0.1 mL of the test composition is dispensed to a finger wearing finger cot and then directly applied to the test area. In case of a two-part test composition, the two compositions are applied to the same test area, with the first test composition (about 0.08 mL per 25 $cm^2$ area) applied to skin first and the second test composition (about 0.1 mL per 5 $cm^2$) dispensed with a new finger cot and applied over the same area treated with the first test composition by gliding motion to coat the treated area, but not by rubbing in, to minimize the mixing of the two test materials.

Clinical Measurements

Efficacy: Efficacy will be assessed in the Treatment Area at every visit.

Investigator's Global Assessment (IGA): Overall severity of atopic dermatitis or Eczema using a 6-point ordinal scale from 0=clear to 5=very severe. This is a static morphological scale that refers to a point in time and not a comparison to Baseline.

Clinical Signs of Atopic Dermatitis/Eczema: The severity of the individual signs of AD or Eczema (erythema, induration/papulation, excoriation, lichenification, and oozing/crusting) using a 5-point ordinal scale from 0=none to 4=severe.

Safety: All AEs and concomitant medications will be recorded at each visit.

P1-016/P2-004 Film durability (Visits 2-5) and itch (Visits 1-5) will be assessed (i) as the percent BSA remaining of the test article film, (ii) by questionnaire and (iii) by photographs (optional) to document focal areas of integrity of the film at the discretion of the investigator.

The Durability Questionnaire will contain the following questions:

(1) the test article peeled from the Treatment Area: (a) not at all, (b) a slight amount, (c) a moderate amount, or (d) a large amount (at Visits 2-5, prior to film removal);

(2) the test article flaked from the Treatment Area: (a) not at all, (b) a slight amount, (c) a moderate amount, or (d) a large amount (at Visits 2-5, prior to film removal);

(3) the test article now covers (a) 0-25%, (b) 25.1-50%, (c) 50.1-75%, (d) 75.1-85%, or (e) 85.1-100% of the original Treatment Area covered with the film at the Baseline visit (at Visits 2-5, prior to film removal);

(4) the film removal process resulted in skin irritation in the Treatment Area: (a) not at all, (b) a slight amount, (c) a moderate amount, or (d) a large amount (at Visits 2-5);

(5) the test article lasted between treatment days, on average, for: (a) 12 hours or less or (b) 12-24 hours (at Visits 2-5); NOTE: this question to be answered by subject.

(6) How would you rate the degree of itch in the Treatment Area over the past 24 hours: 0=none, 1=a trace, 2=mild; 3=moderate; 4=severe? (at Visits 1-5 m, prior to Visit 1 application or film removal) NOTE: this question to be answered by subject.

Other Assessments: Subjects will complete a Subject Questionnaire to document his/her impression of the product and its ease of use at Visit 3 and Visit 5/End of Study.

The Subject Questionnaire will contain the following questions:

(1) overall satisfaction with the study product: (a) excellent [very satisfied], (b) good [moderately satisfied], (c) fair [slightly satisfied], and (d) poor [not satisfied at all].

(2) was the application of the study product easy to perform: (a) very easy, (b) moderately easy, (c) slightly easy, and (d) not easy at all.

(3) was the removal of the study product easy to perform: (a) very easy, (b) moderately easy, (c) slightly easy, and (d) not easy at all.

(4) overall the study product: (a) very significantly improved, (b) improved, (c) did not improve or worsen (no real change) or (d) worsened the treated areas of my skin disease.

(5) based on your experience would you consider using this product to treat your condition rather than other topical medications like steroids: Yes/No, (free text explanation is optional) [Visit 5, EOS only].

Study Endpoints:

Efficacy Endpoints: Atopic dermatitis severity variables (IGA and Clinical Signs of Eczema) will be summarized descriptively by visit. Itch ratings from subject's questionnaire will be analyzed.

Safety Endpoint(s): Endpoints will be summarized descriptively by visit.

Incidence (severity and causality) of any local and systemic treatment emergent AEs (TEAEs).

Percent BSA of test article remaining.

Number of subjects by response for each question of the Durability Questionnaire.

Other Endpoints(s): Number of subjects by response for each question of the Subject Questionnaire.

Statistical Methods:

All statistical processing will be performed using SAS® unless otherwise stated. Summary tables (descriptive statistics and/or frequency tables) will be provided for all variables. Continuous variables will be described by descriptive statistics (n, mean, median, standard deviation, minimum, and maximum). Frequency counts and percentage of subjects within each category will be provided for categorical data.

Study Populations: All randomized subjects who received and applied the test article will be included in the analysis of safety and will be considered the Safety population. Subjects that completed the study without significant protocol deviations will be included in the Evaluable Population.

Efficacy Analyses: The efficacy analyses will be conducted on the Evaluable population.

Investigator's Global Assessment: Frequency distributions of IGA scores will be summarized by severity at each visit.

Clinical Signs of Eczema: Frequency distributions of each clinical sign of Eczema will be summarized by severity at each visit. Reduction of Itch ratings self-reported on a scale of 0=none, 1=a trace, 2=mild, 3=moderate, 4=severe in subject's questionnaires will be analyzed.

Safety Analyses: The analysis of safety will be conducted on the Safety population.

Adverse Events: All AEs reported during the study will be listed, documenting course, severity, investigator assessment of the relationship to the test articles, and outcome. All reported AEs will be summarized by the number of subjects reporting AEs, SOC, PT, severity, and relationship to test article.

Percent BSA of Test Article Remaining in Treatment Area: Descriptive statistics will be used to summarize the percent BSA of the test article remaining in the Treatment Area at each visit.

Durability Questionnaire: Each question from the durability questionnaire will be summarized by frequency and response at each visit.

Urine Pregnancy Tests: UPT results (if applicable) at Baseline will be provided in a listing.

Concomitant Medications and Therapies: Concomitant medications and therapies will be provided in a listing.

Other Analyses: The other analyses will be conducted on the Evaluable population.

Subject Questionnaire: Each question from the subject questionnaire will be summarized by frequency and response at each visit.

Clinical Results:

10 subjects applied P1-016/P2-004 test composition up to 2× daily to a discrete area (0.5-3% BSA) of active disease. Female: 70%, Male: 30%. Age mean: 31.6 years Durability on skin (% remaining): P1-016/P2-004 film was durable on average 24-48 hours and caused little to no irritation when removed Safety: No material safety issues Efficacy (via Investigator's Global Assessment and clinical signs of atopic dermatitis): Marked improvement in overall disease and signs/symptoms over the 30-day treatment. Improvement of clinical signs parallels IGA improvements. Results are also shown in FIG. 18(A-I).

Overall satisfaction: Majority of subjects were satisfied with treatment and rated the study product as easy to use and remove. 88.9% of subjects were moderately or very satisfied with product (Day 30). 88.9% of subjects found product moderately or very easy to apply (Day 30). 88.9% of subjects would consider using the product rather than other medications (Day 30)

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

We claim:

1. A composition for the in-situ formation of a layer over the skin of a subject,
wherein
the composition is a two-part composition comprising a first part and a second part;
the first part comprises Polymer A and Polymer B;
the second part comprises a catalyst;
Polymer A comprises one or more organopolysiloxane(s) having on average at least two alkenyl-functional groups and having a viscosity of about 10,000 to about 2,000,000 cSt at about 25° C.;
Polymer B comprises one or more organopolysiloxane(s) having on average at least two Si—H units and having a viscosity of about 2 to about 500,000 cSt at about 25° C.;
the catalyst facilitates crosslinking of Polymer A and Polymer B; and
wherein the first part or the second part further comprises a reinforcing component selected from the group consisting of surface-treated carbon or graphene.

2. The composition of claim 1,
wherein the first part or the second part further comprises about 0.001% to about 25% by weight of graphene.

3. The composition of claim 1, wherein the second part further comprises Polymer C; and Polymer C comprises one or more organopolysiloxane(s) having on average at least one alkenyl-functional groups and having a viscosity of about 0.7 cSt to about 10,000 cSt at about 25° C.

4. The composition of claim 1,
wherein the first part comprises about 5% to about 90% by weight of Polymer A; about 5% to about 75% by weight of Polymer B.

5. The composition of claim 1, wherein the first part comprises about 5% to about 90% by weight of Polymer A; about 5% to about 30% by weight of Polymer B; and about 0.001% to about 25% by weight of the reinforcing component.

6. The composition of claim 1, wherein the second part comprises as ingredients about 0.001% to about 1% by weight one or more catalyst(s).

7. The composition of claim 1, wherein the second part comprises as ingredients about 0.005% to about 0.05% by weight one or more catalyst(s).

8. A kit comprising the composition of claim 1, further comprising instructions for use, a cleanser suitable for removing said layer from the skin or one or more brush(es), swab(s), and/or mirror(s).

9. A method for modifying skin function, wherein the method comprises applying the composition of claim 1 to the subject in need thereof.

\* \* \* \* \*